(12) United States Patent
Ellis et al.

(10) Patent No.: US 7,780,964 B2
(45) Date of Patent: Aug. 24, 2010

(54) IMMUNOGLOBULINS WHICH BIND NOGO

(75) Inventors: Jonathan Henry Ellis, Stevenage (GB); Paul Andrew Hamblin, Stevenage (GB); Alan Peter Lewis, Stevenage (GB); Paul Alexander Wilson, Stevenage (GB)

(73) Assignee: Glaxo Group Limited (GB)

( * ) Notice: Subject to any disclaimer, the term of this patent is extended or adjusted under 35 U.S.C. 154(b) by 1202 days.

(21) Appl. No.: 11/177,648

(22) Filed: Jul. 6, 2005

(65) Prior Publication Data

US 2006/0029603 A1 Feb. 9, 2006

(51) Int. Cl.
*A61K 39/395* (2006.01)
*C07K 21/08* (2006.01)

(52) U.S. Cl. .............. 424/141.1; 530/387.1; 530/387.3; 530/387.9; 530/388.1; 530/388.23

(58) Field of Classification Search .................. None
See application file for complete search history.

(56) References Cited

U.S. PATENT DOCUMENTS 3,935,074 A * 1/1976 Rubenstein et al. .......... 435/7.9

\* cited by examiner

*Primary Examiner*—Gary Nickol
*Assistant Examiner*—Sandra Wegert
(74) *Attorney, Agent, or Firm*—Jonathan M. Dermott; William T. Han

(57) ABSTRACT

The present invention relates to antibodies to NOGO, pharmaceutical formulations containing them and to the use of such antibodies in the treatment and/or prophylaxis of neurological diseases/disorders.

18 Claims, 9 Drawing Sheets

Figure 1 – Binding ELISA
A.
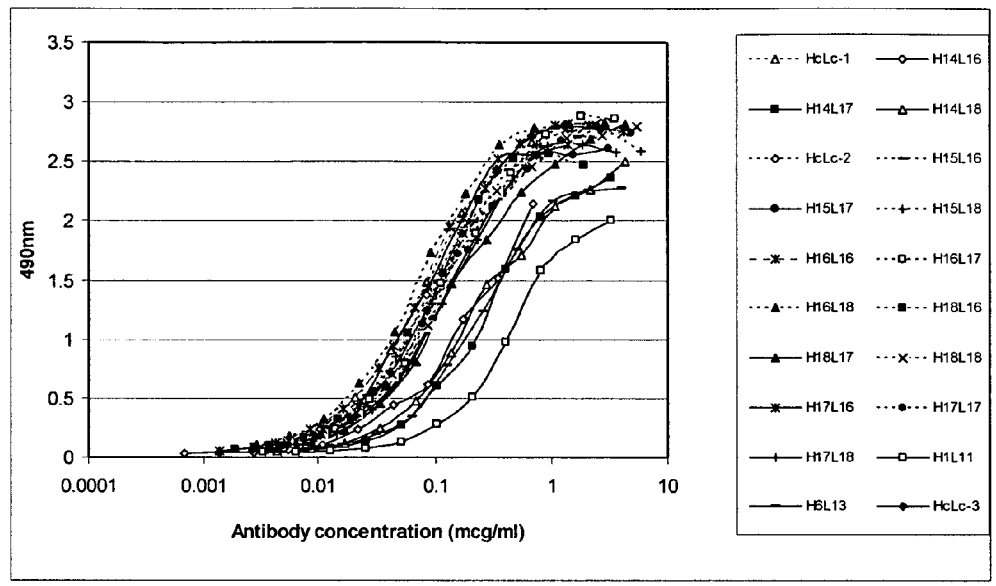
B.
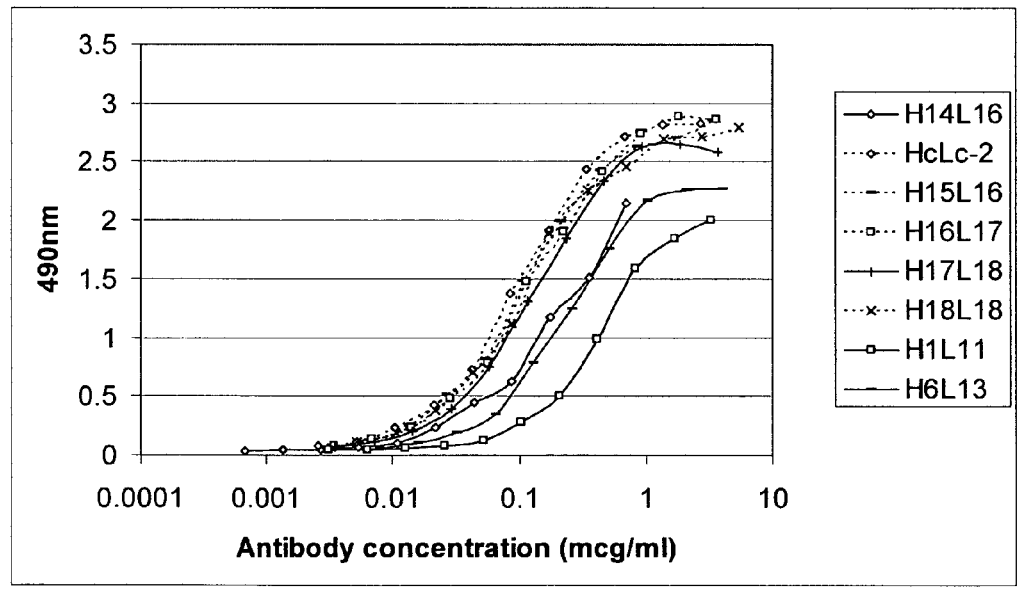

Figure 2
A
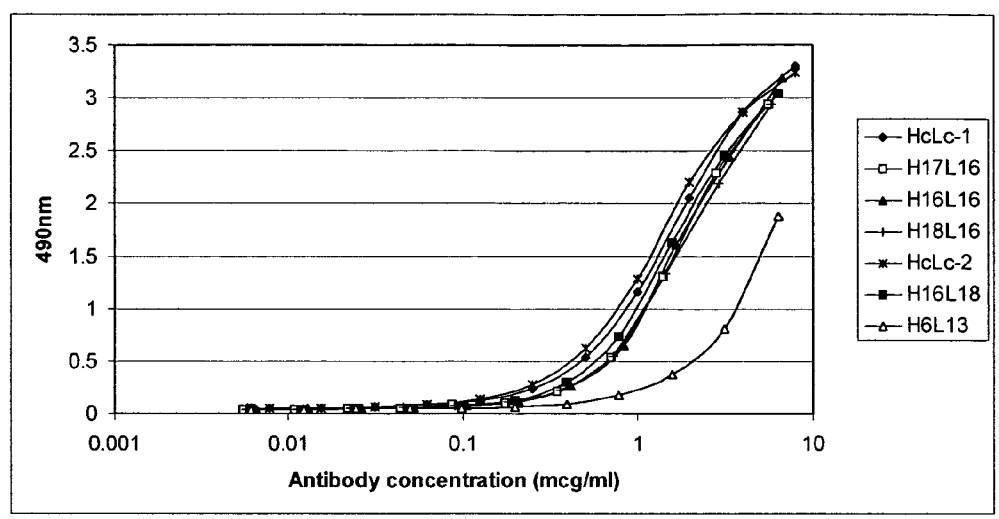
B
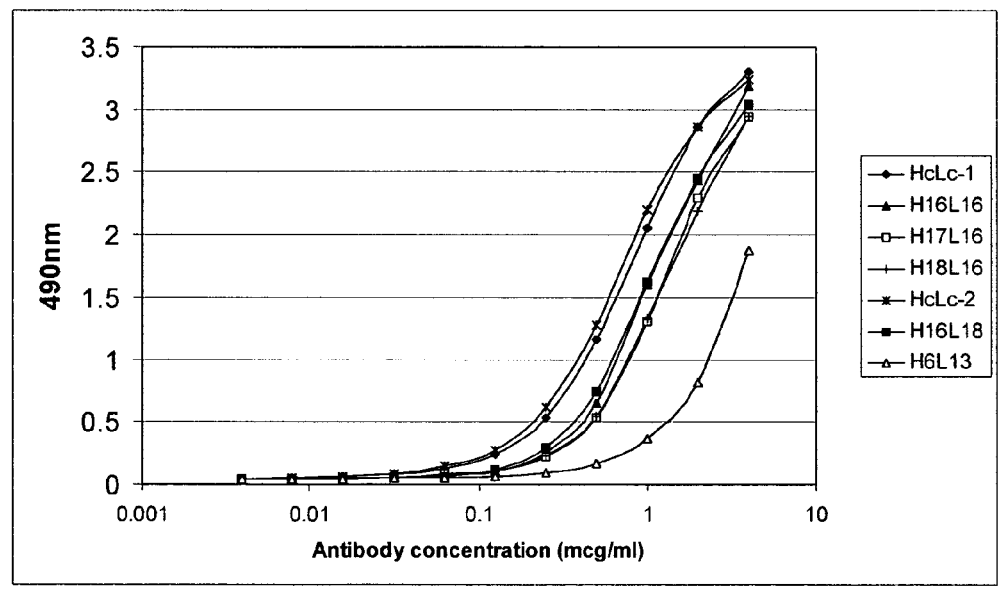

Figure 3 – Examples of NOGO binding ELISAs (Supernatant material)
A. Sample set 1
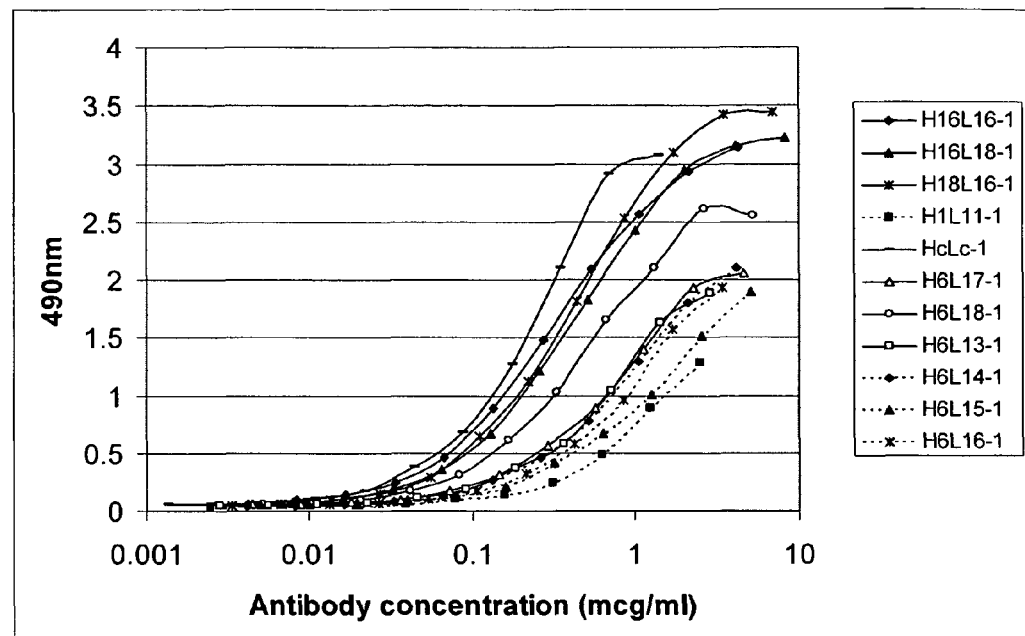
B. Sample set 2
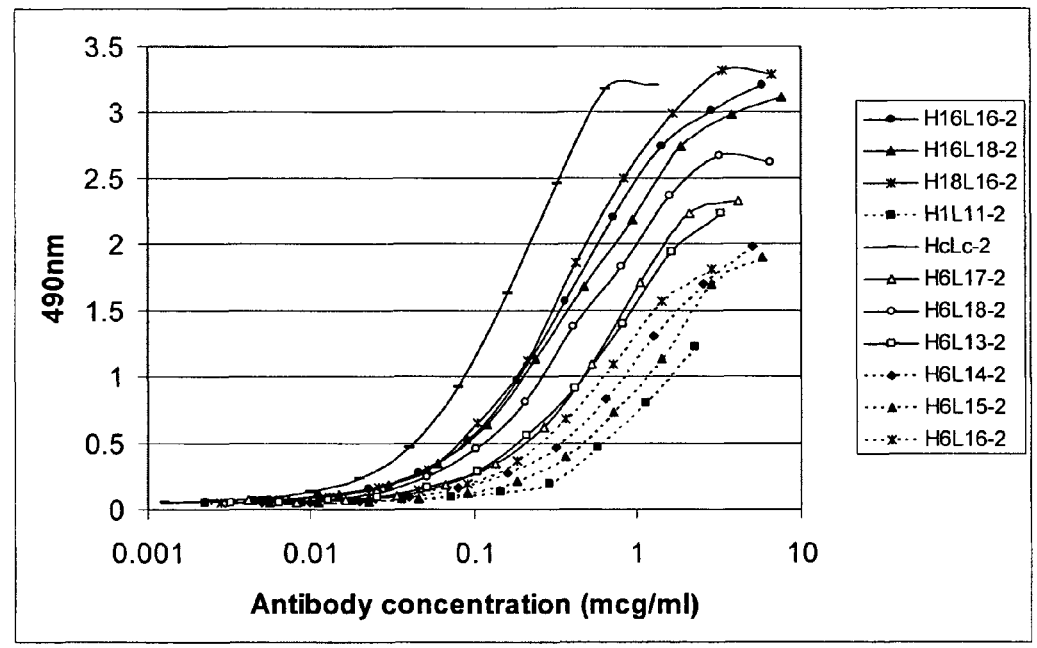

Figure 4 – Examples of NOGO binding ELISAs. Supernatant material
A. Sample set A
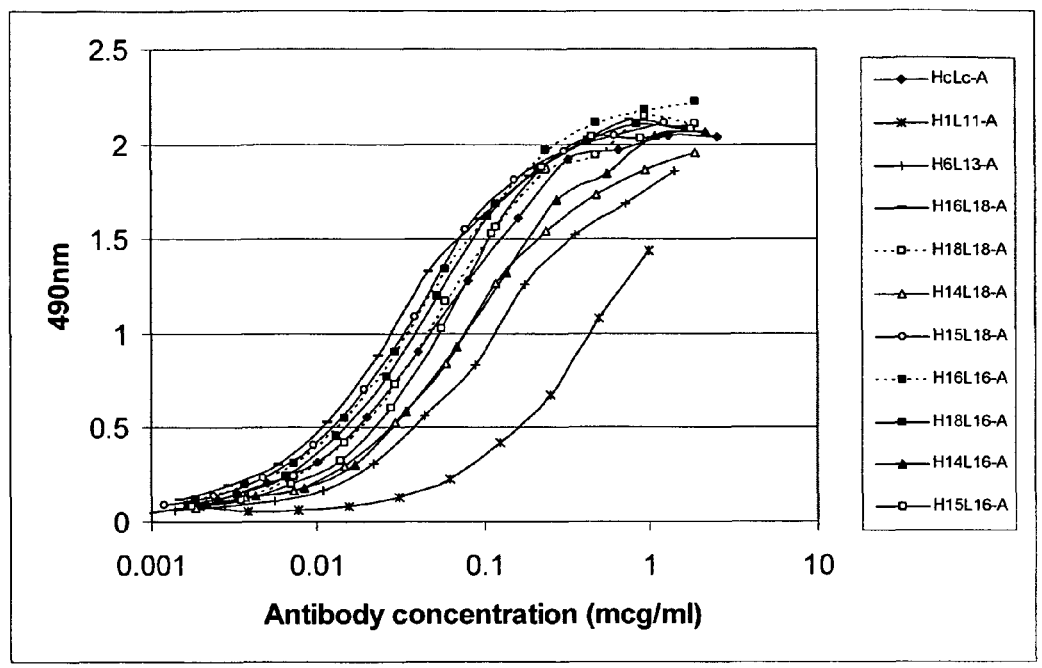
B. Sample set B
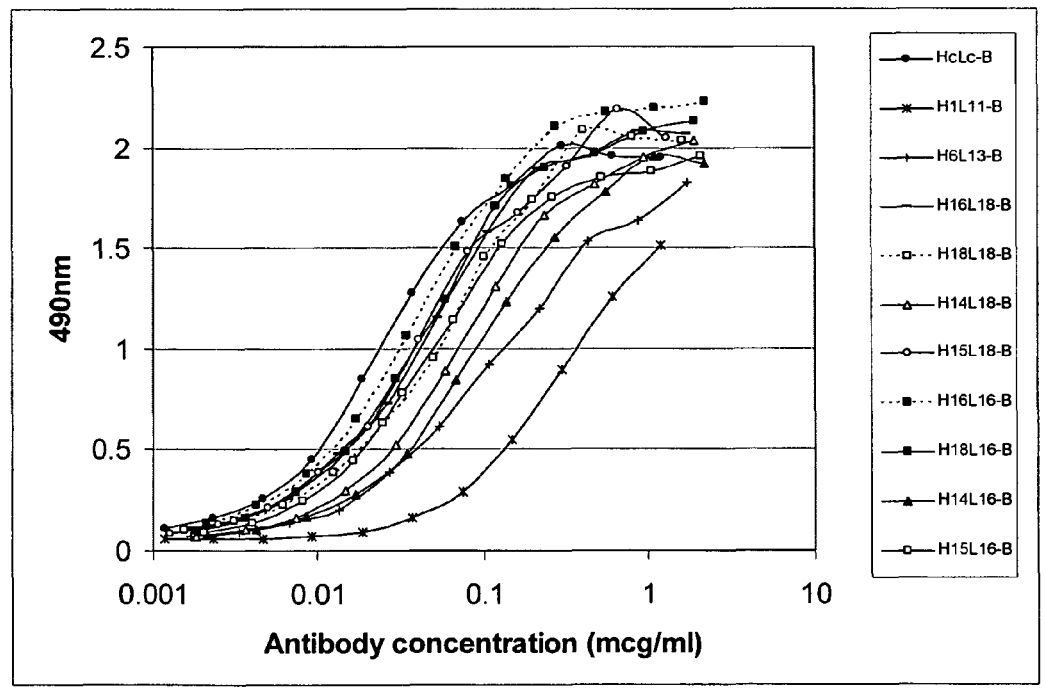

Figure 5 – Examples of NOGO binding ELISAs. Supernatant material
A. Sample set 1
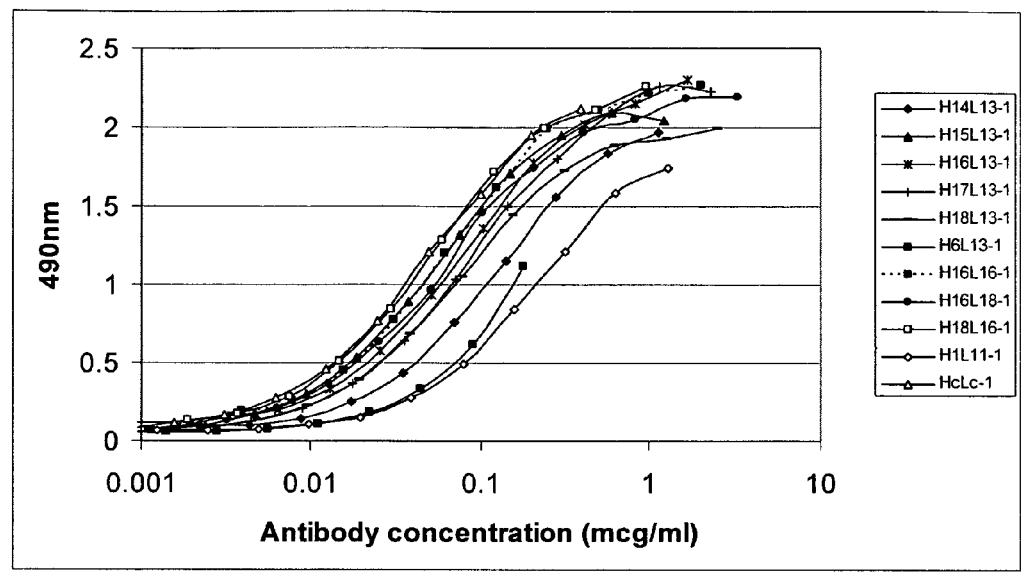
B. Sample set 2
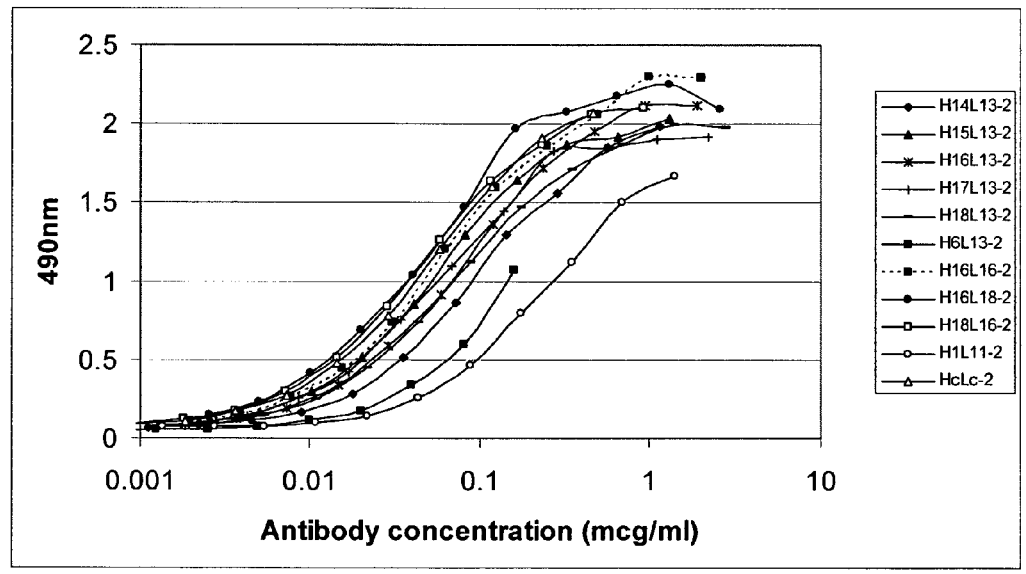

Figure 6 – Examples of FACS data for humanised anti-NOGO antibodies
A.
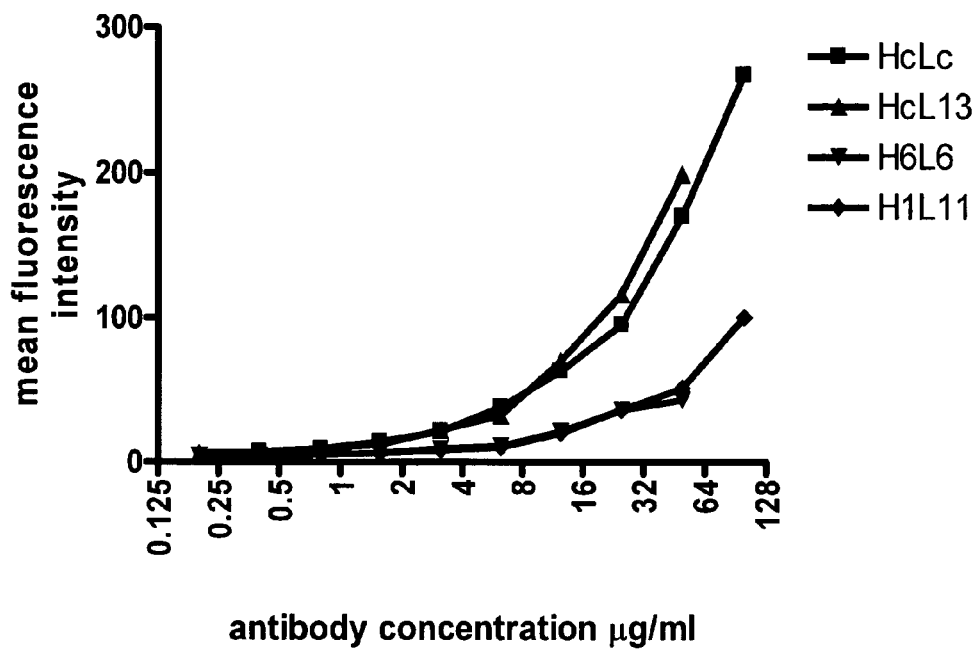
B.
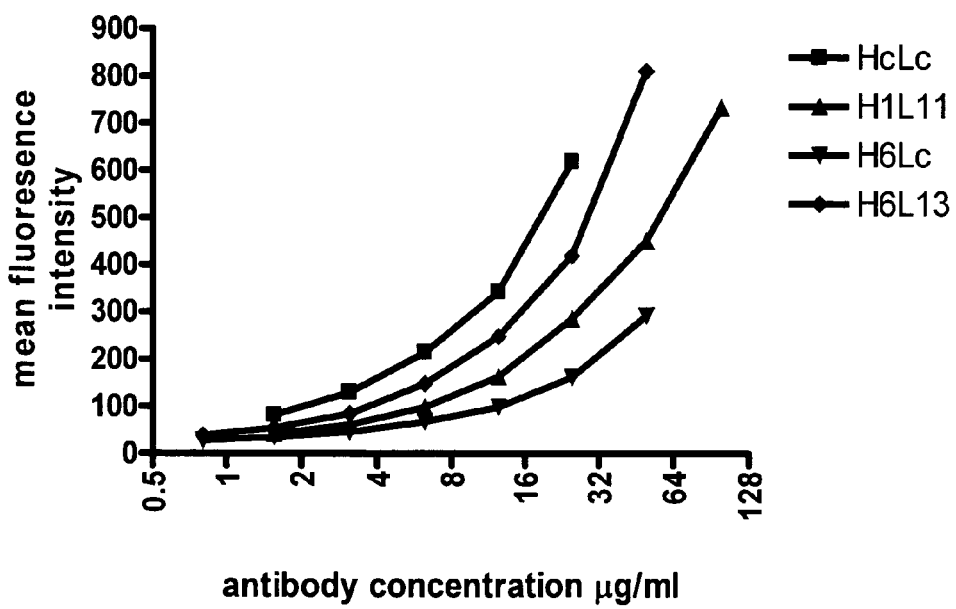

Figure 6 C.
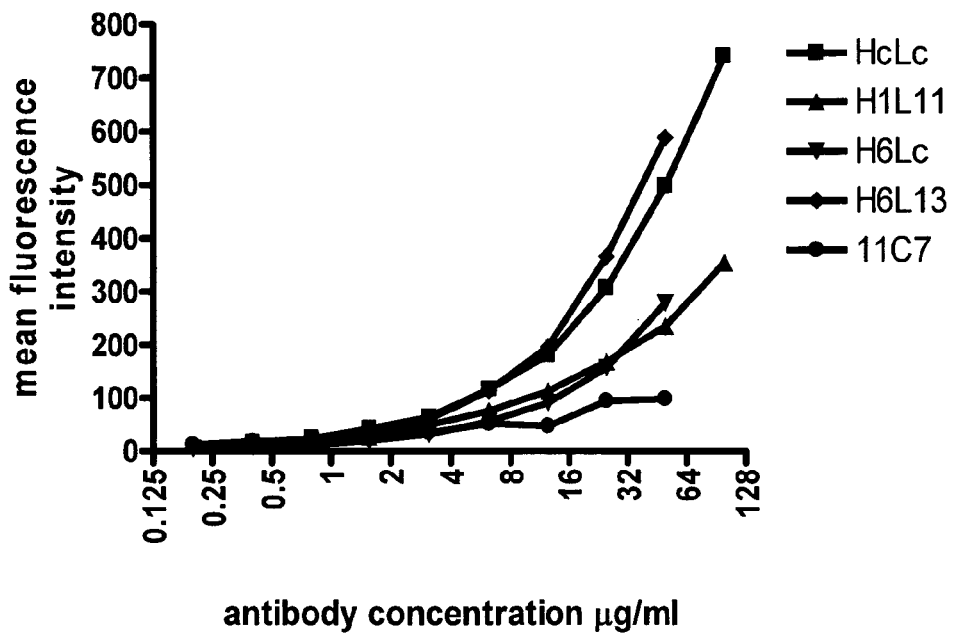
D.
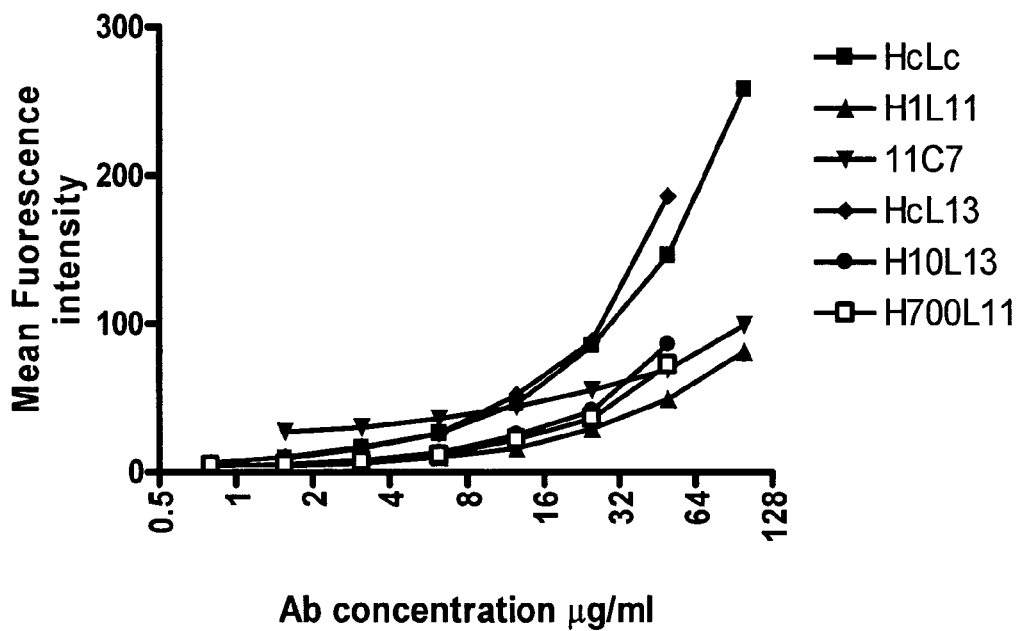

Figure 6 E.
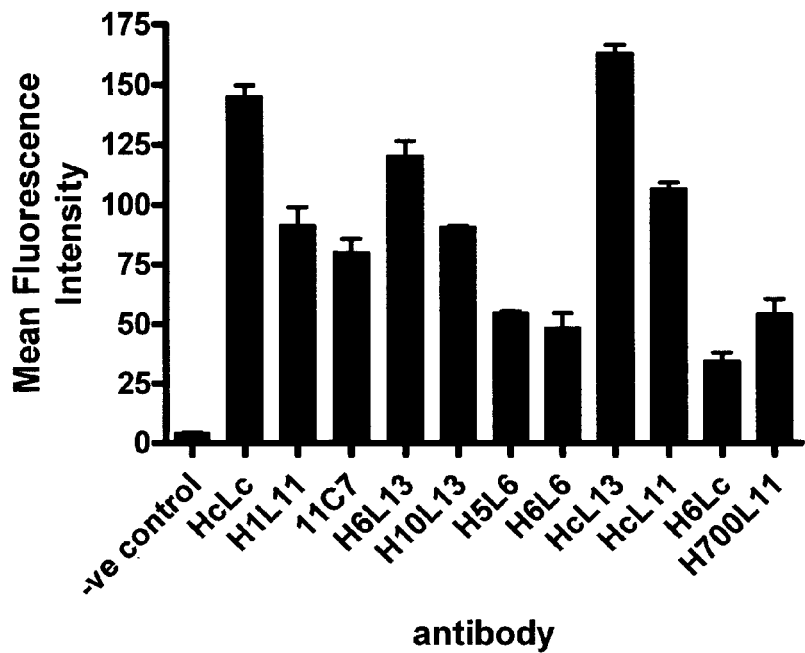
F.
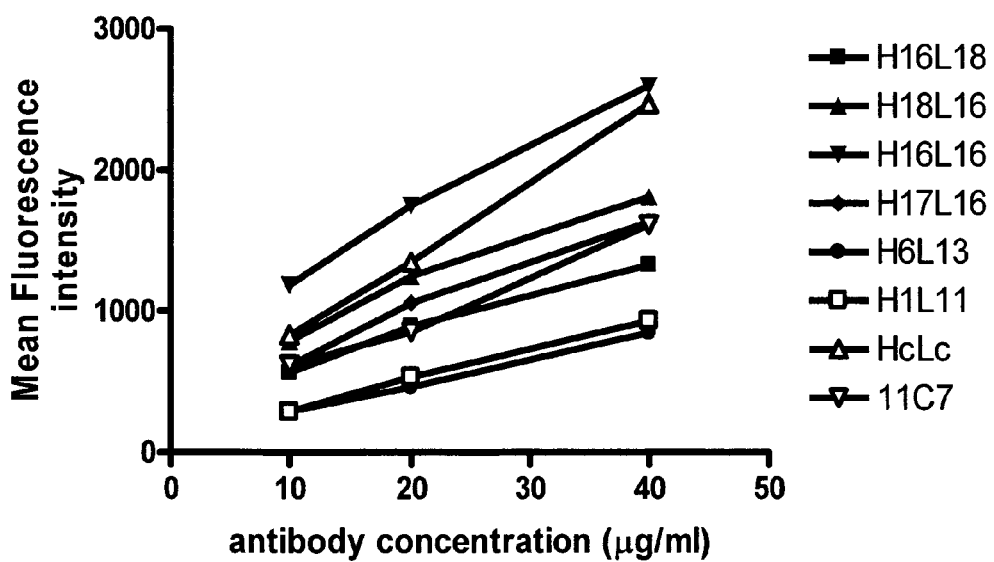

Figure 7 – Competition ELISA
A.
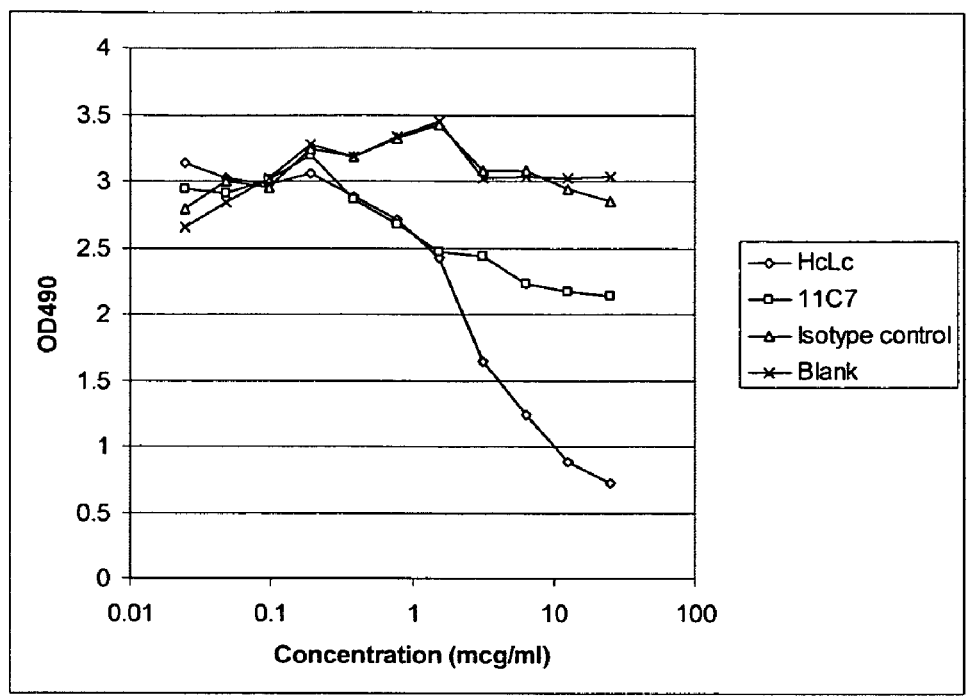
B.
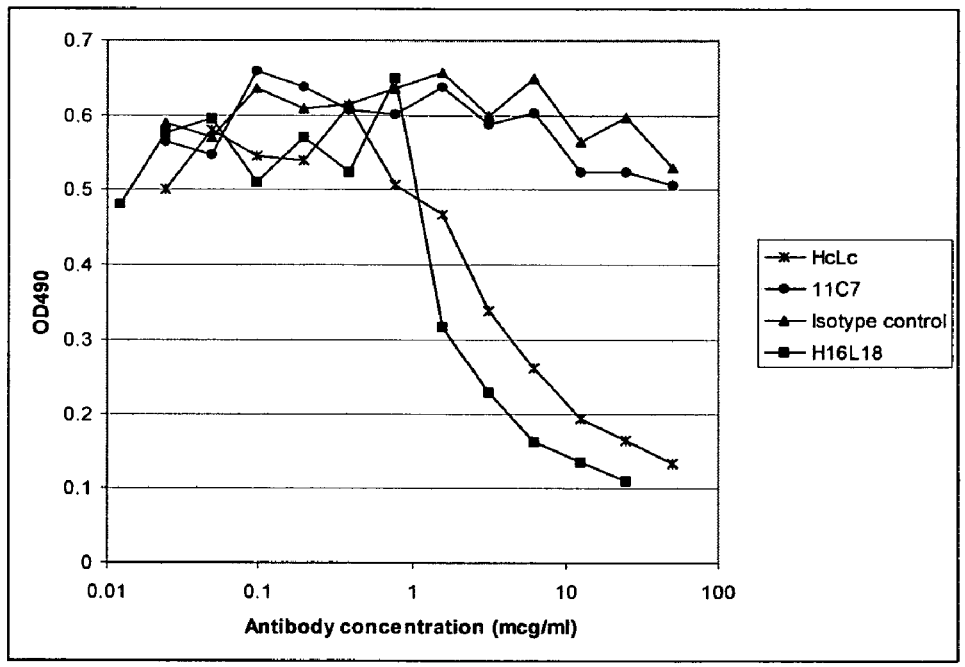

IMMUNOGLOBULINS WHICH BIND NOGO

FIELD OF THE INVENTION

The present invention relates to immunoglobulins, particularly antibodies that bind to NOGO and neutralise the activity thereof, polynucleotides encoding such antibodies, pharmaceutical formulations containing said antibodies and to the use of such antibodies in the treatment and/or prophylaxis of neurological diseases.

BACKGROUND OF THE INVENTION

Stroke is a major cause of death and disability in the Western World. There is no approved therapy for the treatment of stroke other than tissue plasminogen (t-PA) which has to be administered within 3 hours of onset following a computer tomography (CT) scan to exclude haemorrhage. To date most therapeutic agents directed towards the treatment of acute stroke (i.e. neuroprotection), have predominantly involved targeting glutamate receptors and their down stream signalling pathways known to be involved in acute cell death. However to date these strategies have proved unsuccessful in clinical trials and are often associated with dose-limiting side effects (Hill & Hachinski, The Lancet, 352: (suppl III) 10-14 (1998)). Therefore there is a need for novel approaches directed towards the amelioration of cell death following the cessation of blood flow. Neuroprotection is the ability of a treatment to prevent or ameliorate neuronal cell loss in response to an insult or disease process. This maybe achieved by targeting the neurons directly or indirectly by preventing glial (including oligodendrocyte) cell loss.

Following the onset of stroke, some degree of spontaneous functional recovery is observed in many patients, suggesting that the brain has the (albeit limited) ability to repair and/or remodel following injury. Agents that have the potential to enhance this recovery may therefore allow intervention to be made much later (potentially days) following the onset of cerebral ischaemia. Agents which are able to offer both acute neuroprotection and enhance functional recovery may provide significant advantages over current potential neuroprotective strategies.

Alzheimer's disease (AD) is characterised by the presence of two diagnostic features of pathology. These are amyloid plaques and neurofibrillary tangles composed of aggregated beta-amyloid peptide (Aβ40 and Aβ42) and hyperphosphorylated tau respectively (Dawbarn & Allen 2001 Neurobiology of Alzheimer's Disease OUP).

A comprehensive study has shown a strong link in patients between beta-amyloid accumulation and cognitive decline (Naslund et al, JAMA, Mar. 22/29, 2000, Vol. 283, No; 12, page 1571-1577). This is consistent with genetic and epidemiological studies that suggest that some mutations in APP and presenilin genes can predispose to early onset AD, which mutations also enhance the levels of Aβ40 and Aβ42 peptide, including the ratio thereof.

Cleavage of the type I transmembrane amyloid precursor protein (APP) by two distinct proteases designated beta- and gamma-secretase is necessary for the formation of beta-amyloid peptide. The molecular identity of beta-secretase as the aspartyl-protease Asp2/BACE1 has been confirmed (Hussain et al Mol. Cell. NeuroSci. 16, 609-619 (2000); Vassar et al, Science (1999), Oct. 22; 286 (5440):735-741). The nature of gamma-secretase remains the source of some debate and is likely to consist of a high molecular weight complex consisting of at least the following proteins: presenilins, Aph1, Pen2 and nicastrin (reviewed in Medina & Dotti Cell Signalling 2003 15(9):829-41).

The processing of APP within the CNS is likely to occur within a number of cell-types including neurons, oligodendrocytes, astrocytes and microglia. While the overall rate of APP processing in these cells will be influenced by the relative level of expression of APP, BACE1/Asp2, presenilin-1 and -2, Aph1, Pen2 and nicastrin.

Furthermore, additional factors regulating the subcellular location of APP can also influence its processing as shown by the finding that mutation of the YENP motif in the APP cytoplasmic domain which blocks its endocytosis reduces beta-amyloid production (Perez et al 1999 J Biol Chem 274 (27) 18851-6). Retention of the APP-beta-CTF in the ER by the addition of the KKQN retention motif is sufficient to reduce amyloid production in transfected cells (Maltese et al 2001 J Biol Chem 276 (23) 20267-20279). Conversely, elevation of endocytosis, by overexpression of Rab5 is sufficient to elevate amyloid secretion from transfected cells (Grbovic et al 2003 J Biol Chem 278 (33) 31261-31268).

Consistent with these findings further studies have shown that reduction of cellular cholesterol levels (a well known risk factor for AD) reduced beta-amyloid formation. This change was dependent on altered endocytosis as demonstrated by the use of the dominant negative dynamin mutants (K44A) and overexpression of the Rab5 GTPase activating protein RN-Tre (Ehehalt et al 2003 J Cell Biol 160 (1) 113-123).

Cholesterol rich microdomains or rafts are also an important cellular site of beta-amyloid production and APP, BACE1 and components of the gamma-secretase complex have all been shown to transiently reside within rafts. Antibody cross-linking of APP and BACE1 towards cholesterol rich rafts was able to elevate beta-amyloid production (Ehehalt et al 2003 J Cell Biol 160 (1) 113-123). Expression of GPI-anchored BACE1, which is exclusively targeted to lipid rafts, is similarly able to elevate APP cleavage and beta-amyloid production (Cordy et al 2003 PNAS 100(20) 11735-11740).

The mechanisms underlying functional recovery are currently unknown. The sprouting of injured or non-injured axons has been proposed as one possible mechanism. However, although in vivo studies have shown that treatment of spinal cord injury or stroke with neurotrophic factors results in enhanced functional recovery and a degree of axonal sprouting, these do not prove a direct link between the degree of axonal sprouting and extent of functional recovery (Jakeman, et al. 1998, Exp. Neurol. 154: 170-184, Kawamata et al. 1997, Proc Natl Acad. Sci. USA., 94:8179-8184, Ribotta, et al. 2000, J. Neurosci. 20: 5144-5152). Furthermore, axonal sprouting requires a viable neuron. In diseases such as stroke which is associated with extensive cell death, enhancement of functional recovery offered by a given agent post stroke may therefore be through mechanisms other than axonal sprouting such as differentiation of endogenous stem cells, activation of redundant pathways, changes in receptor distribution or excitability of neurons or glia (Fawcett & Asher, 1999, Brain Res. Bulletin, 49: 377-391, Horner & Gage, 2000, Nature 407 963-970).

The limited ability of the central nervous system (CNS) to repair following injury is thought in part to be due to molecules within the CNS environment that have an inhibitory effect on axonal sprouting (neurite outgrowth). CNS myelin is thought to contain inhibitory molecules (Schwab M E and Caroni P (1988) J. Neurosci. 8, 2381-2193). Two myelin proteins, myelin-associated glycoprotein (MAG) and NOGO have been cloned and identified as putative inhibitors of neurite outgrowth (Sato S. et al (1989) Biochem. Biophys. Res.

Comm. 163, 1473-1480; McKerracher L et al (1994) Neuron 13, 805-811; Mukhopadhyay G et al (1994) Neuron 13, 757-767; Torigoe K and Lundborg G (1997) Exp. Neurology 150, 254-262; Schafer et al (1996) Neuron 16, 1107-1113; WO9522344; WO9701352; Prinjha R et al (2000) Nature 403, 383-384; Chen M S et al (2000) Nature 403, 434-439; GrandPre T et al (2000) Nature 403, 439-444; US005250414A; WO200005364A1; WO0031235).

Three forms of human NOGO have been identified: NOGO-A having 1192 amino acid residues (GenBank accession no. AJ251383); NOGO-B, a splice variant which lacks residues 186 to 1004 in the putative extracellular domain (GenBank accession no. AJ251384) and a shorter splice variant, NOGO-C, which also lacks residues 186 to 1004 and also has smaller, alternative amino terminal domain (GenBank accession no. AJ251385) (Prinjha et al (2000) supra).

Inhibition of the CNS inhibitory proteins such as NOGO may provide a therapeutic means to ameliorate neuronal damage and promote neuronal repair and growth thereby potentially assisting recovery from neuronal injury such as that sustained in stroke. Examples of such NOGO inhibitors may include small molecules, peptides and antibodies.

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The variable domains on the light and heavy chains have the same general structure and each domain comprises a framework of four regions, whose sequences are relatively conserved, connected by three complementarity determining regions (CDRs) often referred to as hypervariable regions. The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" US Dept. of Health and Human Services, US Government Printing Office, 1987).

It has been reported that a murine monoclonal antibody, IN-1, that was raised against NI-220/250, a myelin protein which is a potent inhibitor of neurite growth (and subsequently shown to be fragment of NOGO-A), promotes axonal regeneration (Caroni, P and Schwab, M E (1988) Neuron 1 85-96; Schnell, L and Schwab, M E (1990) Nature 343 269-272; Bregman, B S et al (1995) Nature 378 498-501 and Thallmair, M et al (1998) Nature Neuroscience 1 124-131). It has also been reported that NOGO-A is the antigen for IN-1 (Chen et al (2000) Nature 403 434-439). Administration of IN-1 Fab fragment or humanised IN-1 to rats that have undergone spinal cord transection, enhanced recovery (Fiedler, M et al (2002) Protein Eng 15 931-941; Brosamle, C et al (2000) J. Neuroscience 20 8061-8068). However to date there is no evidence in the literature to suggest that IN-1, or its humanised form, can bind and inhibit human NOGO-A, a necessary requirement for a monoclonal antibody to be useful in the therapeutic treatment of NOGO-mediated diseases and disorders such as stroke and neurodegenerative diseases in humans.

Monoclonal antibodies which bind to NOGO are described in WO 04/052932 and WO2005028508. WO 04/052932 discloses a murine antibody 11C7 which binds to certain forms of human NOGO with high affinity.

It is desirable to isolate and develop further therapeutically useful monoclonal antibodies that bind to, and inhibit the activity of, human NOGO. The process of neurodegeneration underlies many neurological diseases/disorders including, but not limited to, acute diseases such as stroke (ischemic or haemorrhagic), traumatic brain injury and spinal cord injury as well as chronic diseases including Alzheimer's disease, fronto-temporal dementias (tauopathies), peripheral neuropathy, Parkinson's disease, Creutzfeldt-Jakob disease (CJD), Schizophrenia, amyotrophic lateral sclerosis (ALS), multiple sclerosis, Huntington's disease, multiple sclerosis and inclusion body myositis. Consequently an anti-NOGO monoclonal antibody may be useful in the treatment of these diseases/disorders. Such antibodies for the treatment of the above mentioned disease/disorders are provided by the present invention and described in detail below.

The unpublished patent application, with the International Patent Application number PCT/GB2004/005325, also discloses high affinity monoclonal antibodies, including a murine monoclonal antibody 2A10, and a humanised variant thereof H1L11.

SUMMARY OF THE INVENTION

The present invention provides a number of monoclonal antibodies that bind to human NOGO. The present application gives reference to many SEQ ID numbers, which are summarised in Table 12, with the actual sequences following that table towards the end of this document.

The murine antibody 2A10 binds to human NOGO with high affinity, and binds to the form of NOGO which is expressed by human cell lines with high affinity. 2A10 has been humanised successfully in the past (H1L11 which comprises the heavy chain variable region H1 (SEQ ID NO. 77) and the light chain variable region L11 (SEQ ID NO. 78)). The present invention provides additional humanised monoclonal antibodies which retain a high proportion of the affinity of the donor antibody (2A10) to human NOGO. In particular the antibodies of the present invention have a high affinity to human NOGO both in recombinant form as expressed in bacterial cells (such as E. Coli), and also in the form that it is expressed by a human neuroblastoma cell line (for example the human neuroblastoma cell line IMR32).

For the purposes of providing humanised variants of 2A10, the present inventors have identified a number of key amino acid residues in the framework sequence of the 2A10 variable regions which are believed to be important in optimal retention of binding affinity to human NOGO. The 2A10 heavy chain variable region (VH) is provided in SEQ ID NO.7; the 2A10 light chain variable region (VL) is provided in SEQ ID NO. 8. Chimeric heavy and light chains comprising the murine variable regions and human constant regions are provided in SEQ ID NOs 9 and 10 respectively (the combination of the two chimeric chains is termed HcLc). The skilled reader will understand that SEQ ID NOs 9 and 10 represent the heavy chain or light chains prior to any processing (e.g. host cell mediated processing) for removal of a signal sequence. Typically the processed forms of the antibody chains will begin at position 20 (after the removal of the signal sequence (residues 1-19) which corresponds to SEQ ID NO. 75).

TABLE 1

CDRs of the 2A10 heavy chain are:

| CDR | According to Kabat | |
|---|---|---|
| H1 | SYWMH | (SEQ ID NO:1) |
| H2 | NINPSNGGTNYNEKFKS | (SEQ ID NO:2) |
| H3 | GQGY | (SEQ ID NO:3) |

TABLE 2

CDRs of 2A10 light chain:

| CDR | According to Kabat | |
|---|---|---|
| L1 | RSSKSLLYKDGKTYLN | (SEQ ID NO:4) |
| L2 | LMSTRAS | (SEQ ID NO:5) |
| L3 | QQLVEYPLT | (SEQ ID NO:6) |

The CDRs were identified according to Kabat (Kabat et al. (1991) "Sequences of proteins of immunological interest"; Fifth Edition; US Department of Health and Human Services; NIH publication No 91-3242). CDRs preferably are as defined by Kabat but following the principles of protein structure and folding as defined by Chothia and Lesk, (Chothia et al., (1989) "Conformations of immunoglobulin hypervariable regions"; Nature 342, p 877-883) it will be appreciated that additional residues may also be considered to be part of the antigen binding region and are thus encompassed by the present invention.

The VH and VL domains H1 and L11 have been previously described in PCT/GB2004/005325, and are a result of the CDRs mentioned in tables 1 and 2 being grafted into human variable regions with high homology to the 2A10 donor antibody, each grafted construct further comprising back mutations in kabat positions 93 and 94 (for the H1 VH) or 4, 45 and 46 (for L11 VL).

The 2A10 antibody is capable of binding to human NOGO, and also binds to Marmoset and Rat NOGO, and it is believed that the new humanised antibodies of the present invention will retain that property. The sequence of Marmoset NOGO-A fragment is given in SEQ ID NO. 113.

Heavy Chain Variable Region (VH)

In one aspect of the present invention the antibodies comprise a heavy chain variable region having the amino acid sequence of SEQ ID NO. 77 (H1 variable region) further comprising a number of substitutions at one or more of positions 12, 20, 38, 40, 48, 67, 68, 70, 72, 74, 76, 79 and 91; wherein each substituted amino acid residue is replaced with the amino acid residue at the equivalent position in SEQ ID NO 7 (the heavy chain variable region of the donor antibody 2A10) and the number of substitutions is between 1 and 13. In other embodiments the number of substitutions is 1, or 2, or 3, or 4, or 5, or 6, or 7, or 8, or 9, or 10, or 11, or 12, or 13. In other embodiments the number of substitutions is between 2 and 13, or 3 and 13, or 4 and 13, or 5 and 13, or 6 and 13, or 7 and 13, or 8 and 13, or 9 and 13, or 10 and 13 or 11 and 13, or 12 and 13.

In this context the substitutions that are described are equivalent in concept to "back-mutations" where the human framework amino acid residues in specific positions within the H1 sequence are back-mutated to the amino acid residues in the equivalent position within the 2A10 donor antibody sequence.

Unless specifically stated otherwise, when a numerical position of an amino acid residue found within a specific sequence is mentioned in this document, for example "position 12", it is intended that the skilled reader assigns the first amino acid in the sequence the position "1" and counts from position one and identifies the amino acid which is in the desired position, in this example the twelfth amino acid residue in the sequence. The skilled reader will notice that this numbering system does not correspond with the Kabat numbering system which is often used for amino acid positions within antibody sequences. The following table (Table 3) illustrates the substitutions/back-mutations of the present invention and gives their numerical positions and the Kabat number for that numerical position:

TABLE 3

| Human framework residue of H1 (SEQ ID NO 77) | Numerical Position | Kabat number of that numerical position | Corresponding residue in murine 2A10 (SEQ ID NO 7) |
|---|---|---|---|
| K | 12 | 12 | V |
| V | 20 | 20 | L |
| R | 38 | 38 | K |
| A | 40 | 40 | R |
| M | 48 | 48 | I |
| R | 67 | 66 | K |
| V | 68 | 67 | A |
| M | 70 | 69 | L |
| R | 72 | 71 | V |
| T | 74 | 73 | K |
| T | 76 | 75 | S |
| V | 79 | 78 | A |
| T | 91 | 87 | S |

With reference to Table 3, in one embodiment the monoclonal antibodies of the present invention comprise the substitution/backmutation at position 79 to form antibodies of "Class A".

For optimal binding affinity, it has been found that the pair of amino acid residues in positions 48 and 68, should be I and A respectively (as they exist in 2A10) or M and V respectively (as they exist in H1). Accordingly, again with reference to Table 3, in another embodiment, "Class B", the monoclonal antibody comprises the substitution at positions 79, 48 and 68.

In another embodiment ("Class C") the monoclonal antibodies of "Class A" or "Class B" further comprise a substitution at positions 40 and/or 67.

In another embodiment the "Class C" monoclonal antibodies of the present invention further comprise a substitution at positions 38, 72 or 70 to form "Class D" antibodies.

In another embodiment the "Class D" monoclonal antibodies further comprise substitutions at one or more of positions 12, 20, 74, 76 or 91 ("Class E").

The following table includes details of 20 different heavy chain variable (VH) regions which may form part of the antibodies of the present invention. Each of the disclosed VH is based on the H1 VH (SEQ ID NO. 77) further comprising the substitutions mentioned in the table (Table 4) where the H1 residue at the relevant position is substituted with the 2A10 residue at that position (in the table, "-" means that there is no substitution in that position, and so the residue remains as in the sequence of H1):

TABLE 4

|  | Numerical Residue No. | | | | | | | | | | | | |
|---|---|---|---|---|---|---|---|---|---|---|---|---|---|
|  | 12 | 20 | 38 | 40 | 48 | 67 | 68 | 70 | 72 | 74 | 76 | 79 | 91 |
|  | | | | | | Kabat No. | | | | | | | |
|  | 12 | 20 | 38 | 40 | 48 | 66 | 67 | 69 | 71 | 73 | 75 | 78 | 87 |
|  | | | | | | | 2A10 | | | | | | |
| New VH (SEQ ID NO. X) | V | L | K | R | I | K | A | L | V | K | S | A | S |
|  | | | | | | | H1 | | | | | | |
|  | K | V | R | A | M | R | V | M | R | T | T | V | T |
| H5 (11) | — | — | — | — | — | — | — | — | — | — | — | A | — |
| H6 (12) | — | — | — | — | I | — | A | — | — | — | — | A | — |
| H700 (13) | — | — | — | — | I | — | A | L | V | K | — | A | — |
| H8 | — | — | — | — | I | — | A | L | V | — | — | A | — |
| H9 | — | L | — | — | I | — | A | L | V | K | — | A | — |
| H10 | — | L | K | — | I | — | A | L | V | K | — | A | — |
| H12 | — | — | — | — | I | — | A | L | — | K | — | — | — |
| H13 | — | — | — | — | I | — | A | — | V | — | — | A | — |
| H14 (14) | V | L | K | — | I | — | A | L | — | — | — | A | — |
| H15 (15) | V | L | K | R | I | K | A | L | V | — | S | A | S |
| H16 (16) | — | — | K | R | I | K | A | L | V | K | — | A | — |
| H17 (17) | V | L | K | R | I | K | A | L | V | K | — | A | — |
| H18 (18) | V | L | K | R | I | K | A | L | V | K | S | A | S |
| H19 (85) | — | — | — | R | I | — | A | — | — | — | — | A | — |
| H20 (86) | — | — | — | — | I | K | A | — | — | — | — | A | — |
| H21 (87) | — | — | — | R | I | K | A | — | — | — | — | A | — |
| H22 (88) | — | — | K | R | I | K | A | — | — | — | — | A | — |
| H23 (89) | — | — | K | R | I | K | A | — | V | — | — | A | — |
| H24 (90) | — | — | K | R | I | K | A | L | V | — | — | A | — |
| H25 (91) | — | — | — | R | — | — | — | — | — | — | — | A | — |

Accordingly there is provided a monoclonal antibody comprising the heavy chain variable region having a sequence given in any one of SEQ ID NOs: 11-18 or 85-91. In another embodiment there is provided a monoclonal antibody comprising a heavy chain having a sequence given in any one of SEQ ID NOs: 26-33 or 92-98.

In a particular embodiment the antibody comprises the VH regions provided in SEQ ID NOs 11, 12, 16, 18, 85, 86, 87 or 91 or the heavy chains provided in SEQ ID NOs 26, 27, 31, 33, 92, 93, 94 or 98.

Light Chain Variable Region

In one aspect of the present invention the antibodies comprise a light chain variable region having the amino acid sequence of SEQ ID NO. 20 (L13 variable region) optionally further comprising a number of substitutions at one or more of positions 4, 7, 11, 19, 42, 64 and 70; wherein each substituted amino acid residue is replaced with the amino acid residue at the equivalent position in SEQ ID NO. 8 (the light chain variable region of the donor antibody 2A10) and the number of substitutions is between 0 and 7. In other embodiments the number of substitutions is 1, or 2, or 3, or 4, or 5, or 6, or 7. In other embodiments the number of substitutions is between 2 and 7, or 3 and 7, or 4 and 7, or 5 and 7, or 6 and 7.

The following table (Table 5) illustrates the substitutions/back-mutations of the present invention and gives their numerical positions and the Kabat number for that numerical position:

TABLE 5

| Human framework residue of L13 (SEQ ID NO 20) | Numerical Position | Kabat number | Corresponding residue in murine 2A10 (SEQ ID NO 8) |
|---|---|---|---|
| M | 4 | 4 | I |
| S | 7 | 7 | D |
| L | 11 | 11 | N |
| A | 19 | 19 | V |
| Q | 42 | 37 | L |
| P | 64 | 59 | S |
| G | 70 | 65 | S |

With reference to Table 5, in another embodiment, "Class X", the monoclonal antibodies of the present invention comprise a VL region having the substitution/backmutation at positions 11 and 19. In another embodiment "Class Y" the monoclonal antibodies of "Class X" further comprise the substitution in position 42. In a further embodiment the monoclonal antibodies of "Class X" or "Class Y" further comprise a back mutation in positions 7, 64 or 70 to form "Class Z".

Again with reference to Table 5, in another embodiment the monoclonal antibodies of the present invention comprise a VL region having a substitution at position 4 (corresponding to L11 (SEQ ID NO.78).

The following table (Table 6) includes details of seven different light chain variable (VL) regions which may form part of the antibodies of the present invention. Each of the disclosed VL is, or is based on, the L13 VL (SEQ ID NO. 20) optionally further comprising the substitutions mentioned in the table where the L13 residue at the relevant position is substituted with the 2A10 residue at that position (in the table, "-" means that there is no substitution in that position, and so the residue remains as in the sequence of L13):

TABLE 6

|  | Numerical Residue No. | | | | | | |
|---|---|---|---|---|---|---|---|
|  | 4 | 7 | 11 | 19 | 42 | 64 | 70 |
|  | | | | Kabat No. | | | |
|  | 4 | 7 | 11 | 19 | 37 | 59 | 65 |
|  | | | | 2A10 | | | |
| New VL (SEQ ID NO. X) | I | D | N | V | L | S | S |
|  | | | | L13 | | | |
|  | M | S | L | A | Q | P | G |
| L11 (78) | I | — | — | — | — | — | — |
| L13 (20) | — | — | — | — | — | — | — |
| L14 (21) | — | — | — | — | L | — | — |
| L15 (22) | — | — | — | — | L | S | — |
| L16 (23) | — | — | N | V | L | — | — |
| L17 (24) | — | D | — | — | — | S | S |
| L18 (25) | — | D | N | V | L | S | S |

Accordingly there is provided a monoclonal antibody comprising the light chain variable region having a sequence given in any one of SEQ ID NOs: 20-25 or 78. In another embodiment there is provided a monoclonal antibody comprising a light chain having a sequence given in any one of SEQ ID NOs: 35-40 or 80.

Alternatively there is provided a monoclonal antibody comprising the light chain variable region having the sequence given in SEQ ID NO. 19, or a light chain having the sequence given in SEQ ID NO. 34.

In a particular embodiment the antibody comprises the VL regions provided in SEQ ID NOs 20, 23 and 25 or the light chains provided in SEQ ID NOs 35, 38 and 40.

Specific Combinations of Heavy and Light Chain Variable Regions

The antibodies of the present invention comprise a heavy chain variable region and a light chain variable region.

In one embodiment the antibody comprises:
(a) A heavy chain variable region having the amino acid sequence of SEQ ID NO. 77 (H1 variable region) further comprising a number of substitutions at one or more of positions 12, 20, 38, 40, 48, 67, 68, 70, 72, 74, 76, 79 and 91; wherein each substituted amino acid residue is replaced with the amino acid residue at the equivalent position in SEQ ID NO 7 (the heavy chain variable region of the donor antibody 2A10) and the number of substitutions is between 1 and 13. In other embodiments the number of substitutions is 1, or 2, or 3, or 4, or 5, or 6, or 7, or 8, or 9, or 10, or 11, or 12, or 13; and
(b) a light chain variable region selected from SEQ ID NOs 20-25 or 78.

Particular embodiments are antibodies comprising the following combinations of heavy and light chain variable regions: H1L13 (SEQ ID 77+SEQ ID 20), H5L13 (SEQ ID 11+SEQ ID 20), H6L13 (SEQ ID 12+SEQ ID 20), H14L13 (SEQ ID 14+SEQ ID 20), H15L13 (SEQ ID 15+SEQ ID 20), H16L13 (SEQ ID 16+SEQ ID 20), H17L13 (SEQ ID 17+SEQ ID 20), H18L13 (SEQ ID 18+SEQ ID 20), H19L13 (SEQ ID 85+SEQ ID 20), H20L13 (SEQ ID 86+SEQ ID 20), H21L13 (SEQ ID 87+SEQ ID 20), H22L13 (SEQ ID 88+SEQ ID 20), H23L13 (SEQ ID 89+SEQ ID 20), H24L13 (SEQ ID 90+SEQ ID 20), H25L13 (SEQ ID 91+SEQ ID 20), H700L13 (SEQ ID 13+SEQ ID 20), H1L16 (SEQ ID 77+SEQ ID 23), H5L16 (SEQ ID 11+SEQ ID 23), H6L16 (SEQ ID 12+SEQ ID 23), H14L16 (SEQ ID 14+SEQ ID 23), H15L16 (SEQ ID 15+SEQ ID 23), H16L16 (SEQ ID 16+SEQ ID 23), H17L16 (SEQ ID 17+SEQ ID 23), H18L16 (SEQ ID 18+SEQ ID 23), H19L16 (SEQ ID 85+SEQ ID 23), H20L16 (SEQ ID 86+SEQ ID 23), H21L16 (SEQ ID 87+SEQ ID 23), H22L16 (SEQ ID 88+SEQ ID 23), H23L16 (SEQ ID 89+SEQ ID 23), H24L16 (SEQ ID 90+SEQ ID 23), H25L16 (SEQ ID 91+SEQ ID 23), H700L16 (SEQ ID 13+SEQ ID 23), H1L18 (SEQ ID 77+SEQ ID 25), H5L18 (SEQ ID 11+SEQ ID 25), H6L18 (SEQ ID 12+SEQ ID 25), H14L18 (SEQ ID 14+SEQ ID 25), H15L18 (SEQ ID 15+SEQ ID 25), H16L18 (SEQ ID 16+SEQ ID 25), H17L18 (SEQ ID 17+SEQ ID 25), H18L18 (SEQ ID 18+SEQ ID 25), H19L18 (SEQ ID 85+SEQ ID 25), H20L18 (SEQ ID 86+SEQ ID 25), H21L18 (SEQ ID 87+SEQ ID 25), H22L18 (SEQ ID 88+SEQ ID 25), H23L18 (SEQ ID 89+SEQ ID 25), H24L18 (SEQ ID 90+SEQ ID 25), H25L18 (SEQ ID 91+SEQ ID 25), H700L18 (SEQ ID 13+SEQ ID 25).

Other embodiments are antibodies comprising the following combinations of heavy and light chain variable regions: H1L14 (SEQ ID 77+SEQ ID 21), H5L14 (SEQ ID 11+SEQ ID 21), H6L14 (SEQ ID 12+SEQ ID 21), H14L14 (SEQ ID 14+SEQ ID 21), H15L14 (SEQ ID 15+SEQ ID 21), H16L14 (SEQ ID 16+SEQ ID 21), H17L14 (SEQ ID 17+SEQ ID 21), H18L14 (SEQ ID 18+SEQ ID 21), H19L14 (SEQ ID 85+SEQ ID 21), H20L14 (SEQ ID 86+SEQ ID 21), H21L14 (SEQ ID 87+SEQ ID 21), H22L14 (SEQ ID 88+SEQ ID 21), H23L14 (SEQ ID 89+SEQ ID 21), H24L14 (SEQ ID 90+SEQ ID 21), H25L14 (SEQ ID 91+SEQ ID 21), H700L14 (SEQ ID 13+SEQ ID 21), H1L15 (SEQ ID 77+SEQ ID 22), H5L15 (SEQ ID 11+SEQ ID 22), H6L15 (SEQ ID 12+SEQ ID 22), H14L15 (SEQ ID 14+SEQ ID 22), H15L15 (SEQ ID 15+SEQ ID 22), H16L15 (SEQ ID 16+SEQ ID 22), H17L15 (SEQ ID 17+SEQ ID 22), H18L15 (SEQ ID 18+SEQ ID 22), H19L15 (SEQ ID 85+SEQ ID 22), H20L15 (SEQ ID 86+SEQ ID 22), H21L15 (SEQ ID 87+SEQ ID 22), H22L15 (SEQ ID 88+SEQ ID 22), H23L15 (SEQ ID 89+SEQ ID 22), H24L15 (SEQ ID 90+SEQ ID 22), H25L15 (SEQ ID 91+SEQ ID 22), H700L15 (SEQ ID 13+SEQ ID 22), H1L17 (SEQ ID 77+SEQ ID 24), H5L17 (SEQ ID 11+SEQ ID 24), H6L17 (SEQ ID 12+SEQ ID 24), H14L17 (SEQ ID 14+SEQ ID 24), H15L17 (SEQ ID 15+SEQ ID 24), H16L17 (SEQ ID 16+SEQ ID 24), H17L17 (SEQ ID 17+SEQ ID 24), H18L17 (SEQ ID 18+SEQ ID 24), H19L17 (SEQ ID 85+SEQ ID 24), H20L17 (SEQ ID 86+SEQ ID 24), H21L17 (SEQ ID 87+SEQ ID 24), H22L17 (SEQ ID 88+SEQ ID 24), H23L17 (SEQ ID 89+SEQ ID 24), H24L17 (SEQ ID 90+SEQ ID 24), H25L17 (SEQ ID 91+SEQ ID 24), H700L17 (SEQ ID 13+SEQ ID 24).

Further embodiments are antibodies comprising the following combinations of heavy and light chain variable regions: H1L6 (SEQ ID 77+SEQ ID 19), H5L6 (SEQ ID 11+SEQ ID 19), H6L6 (SEQ ID 12+SEQ ID 19), H14L6 (SEQ ID 14+SEQ ID 19), H15L6 (SEQ ID 15+SEQ ID 19), H16L6 (SEQ ID 16+SEQ ID 19), H17L6 (SEQ ID 17+SEQ ID 19), H18L6 (SEQ ID 18+SEQ ID 19), H19L6 (SEQ ID 85+SEQ ID 19), H20L6 (SEQ ID 86+SEQ ID 19), H21L6 (SEQ ID 87+SEQ ID 19), H22L6 (SEQ ID 88+SEQ ID 19), H23L6 (SEQ ID 89+SEQ ID 19), H24L6 (SEQ ID 90+SEQ ID 19), H25L6 (SEQ ID 91+SEQ ID 19), H700L6 (SEQ ID 13+SEQ ID 19), H5L11 (SEQ ID 11+SEQ ID 78), H6L11 (SEQ ID 12+SEQ ID 78), H14L11 (SEQ ID 14+SEQ ID 78), H15L11 (SEQ ID 15+SEQ ID 78), H16L11 (SEQ ID 16+SEQ ID 78), H17L11 (SEQ ID 17+SEQ ID 78), H18L11 (SEQ ID 18+SEQ ID 78), H19L11 (SEQ ID 85+SEQ ID 78), H20L11 (SEQ ID 86+SEQ ID 78), H21L11 (SEQ ID 87+SEQ ID 78), H22L11 (SEQ ID 88+SEQ ID 78), H23L11 (SEQ ID 89+SEQ ID 78), H24L11 (SEQ ID 90+SEQ ID 78), H25L11 (SEQ ID 91+SEQ ID 78), H700L11 (SEQ ID 13+SEQ ID 78).

Whole Antibodies

Further, the invention also provides a humanised antibody which binds to and neutralises NOGO, preferably human NOGO, more preferably human NOGO-A. More specifically there is provided a humanised antibody comprising a heavy chain variable region as described herein and a light chain variable region as described herein.

The humanised antibodies of the present invention bind to human NOGO with a comparable affinity to that of the murine donor antibody 2A10. In one embodiment the binding of the antibody of the present invention to NOGO has an affinity constant (KD, as measured by BiaCore techniques) within 10 fold of 2A10, and in another embodiment the affinity constant is within three or two fold of 2A10. In another embodiment the affinity constant is within three or two fold of that of 2A10 and the off-rate (kd) is within 10 fold, or three fold, or two fold of 2A10. The method of measuring the affinity constant and the off-rate of the antibody should be clear to the skilled reader, however the kinetic analysis BiaCore method given in Example 5 of this document is illustrative in this regard. For example, the affinity constant and the off-rate of 2A10 as measured by BiaCore kinetic analysis is about commonly in the region of 1 nM and $1.84 \times 10^{-3}$ (kd 1/s) respectively; in the same assay the antibodies of one embodiment of the present invention will have an affinity constant of less than 8-10 nM and $1.84 \times 10^{-2}$.

In typical embodiments, the antibodies of the invention are of the IgG class, more typically human IgG1 or IgG4, with a K type human light chain.

A further aspect of the invention provides a pharmaceutical composition comprising an anti-NOGO antibody of the present invention or functional fragment thereof together with a pharmaceutically acceptable diluent or carrier.

In a further aspect, the present invention provides a method of treatment or prophylaxis of stroke (particularly ischemic stroke) and other neurological diseases, in particular Alzheimer's disease, in a human which comprises administering to said human in need thereof an effective amount of an anti-NOGO antibody of the invention or functional fragments thereof.

In another aspect, the invention provides the use of an anti-NOGO antibody of the invention or a functional fragment thereof in the preparation of a medicament for treatment or prophylaxis of stroke (particularly ischemic stroke) and other neurological diseases, in particular Alzheimer's disease.

In a further aspect, the present invention provides a method of inhibiting neurodegeneration and/or promoting functional recovery in a human patient afflicted with, or at risk of developing, a stroke (particularly ischemic stroke) or other neurological disease, in particular Alzheimer's disease, which comprises administering to said human in need thereof an effective amount of an anti-NOGO antibody of the invention or a functional fragment thereof.

In a yet further aspect, the invention provides the use of an anti-NOGO antibody of the invention or a functional fragment thereof in the preparation of a medicament for inhibiting neurodegeneration and/or promoting functional recovery in a human patient afflicted with, or at risk of developing, a stroke and other neurological disease, in particular Alzheimer's disease.

Other aspects and advantages of the present invention are described further in the detailed description and the preferred embodiments thereof.

In one embodiment the full length antibodies are those comprising the light chains of SEQ ID NOs 34-40 and the heavy chains of SEQ ID NOs 92-98; and in particular the light chains of SEQ ID NOs 35, 38 or 40 and heavy chains of SEQ ID NOs 92, 93, 94 or 98. It will be apparent to those skilled in the art that all of the sequences given for the full length antibody chains in Table 7 and 12 (and appended sequences) represent the heavy chain or light chains prior to any processing (e.g. host cell mediated processing) for removal of a signal sequence. Typically the processed forms of the antibody chains will begin at position 20 (after the removal of the signal sequence (residues 1-19) which corresponds to SEQ ID NO. 75). The present invention provides the antibodies having the polypeptide sequences listed (after removal of the first 19 amino acids of the signal sequence), and also provides the antibodies in the form in which they are produced and purified from host cells expressing the polynucleotides encoding the heavy and light chain.

TABLE 7

Specific full length antibodies include:

| Antibody | Light Chain | Heavy Chain |
| --- | --- | --- |
| H5L13 FL | SEQ ID NO. 35 | SEQ ID NO. 26 |
| H6L13 FL | SEQ ID NO. 35 | SEQ ID NO. 27 |
| H19L13 FL | SEQ ID NO. 35 | SEQ ID NO. 92 |
| H20L13 FL | SEQ ID NO. 35 | SEQ ID NO. 93 |
| H21L13 FL | SEQ ID NO. 35 | SEQ ID NO. 94 |
| H25L13 FL | SEQ ID NO. 35 | SEQ ID NO. 98 |
| H16L16 FL | SEQ ID NO. 38 | SEQ ID NO. 31 |
| H19L16 FL | SEQ ID NO. 38 | SEQ ID NO. 92 |
| H20L16 FL | SEQ ID NO. 38 | SEQ ID NO. 93 |
| H21L16 FL | SEQ ID NO. 38 | SEQ ID NO. 94 |
| H25L16 FL | SEQ ID NO. 38 | SEQ ID NO. 98 |
| H16L18 FL | SEQ ID NO. 40 | SEQ ID NO. 31 |
| H18L16 FL | SEQ ID NO. 38 | SEQ ID NO. 33 |

TABLE 7-continued

Specific full length antibodies include:

| Antibody | Light Chain | Heavy Chain |
| --- | --- | --- |
| H19L18 FL | SEQ ID NO. 40 | SEQ ID NO. 92 |
| H20L18 FL | SEQ ID NO. 40 | SEQ ID NO. 93 |
| H21L18 FL | SEQ ID NO. 40 | SEQ ID NO. 94 |
| H25L18 FL | SEQ ID NO. 40 | SEQ ID NO. 98 |

Alternatively the substitutions mentioned above, being the back mutations to the exact amino residue found in the equivalent position within the donor 2A10 murine sequence, may be any substitution to an amino acid which is a conservative substitution of the exact residue found in the equivalent position within the donor 2A10 murine sequence. The term "conservative substitution" is clear to the skilled reader, and includes for instance a substitution of an amino acid with another amino acid residue having a similar physical, chemical or structural property such as pH, charge, hydrophobicity, aromaticity etc.

DESCRIPTION OF THE FIGURES

FIGS. 1 A and B, ELISA data for monoclonal antibody supernatants binding to recombinant human NOGO.

FIGS. 2 A and B, ELISA data for purified monoclonal antibody binding to recombinant human NOGO.

FIGS. 3 A and B, ELISA data for monoclonal antibody supernatants binding to recombinant human NOGO.

FIGS. 4 A and B, ELISA data for monoclonal antibody supernatants binding to recombinant human NOGO.

FIGS. 5 A and B, ELISA data for monoclonal antibody supernatants binding to recombinant human NOGO.

FIG. 6, A to F, FACS data for purified antibody binding to human NOGO expressed by human neuroblastoma cells.

FIG. 7, Competition ELISA results

DETAILED DESCRIPTION OF THE INVENTION

Antibodies of the invention typically have the structure of a natural antibody or functional fragment thereof. The antibody may therefore comprise a full length antibody, a (Fab)$_2$ fragment, a Fab fragment, a light chain dimer or a heavy chain dimer. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antibody may comprise modifications of all classes eg. IgG dimers, Fc mutants that no longer bind Fc receptors or mediate Clq binding. The antibody may also be a chimeric antibody of the type described in WO86/01533 which comprises an antigen binding region and a non-immunoglobulin region. The antigen binding region is an antibody light chain variable domain or heavy chain variable domain. Typically the antigen binding region comprises both light and heavy chain variable domains. The non-immunoglobulin region is fused at its C terminus to the antigen binding region. The non-immunoglobulin region is typically a non-immunoglobulin protein and may be an enzyme, a toxin or protein having known binding specificity. The two regions of this type of chimeric antibody may be connected via a cleavable linker sequence. Immunoadhesins having the CDRs as hereinbefore described are also contemplated in the present invention.

The constant region is selected according to the functionality required. Normally an IgG1 will demonstrate lytic ability through binding to complement and/or will mediate ADCC (antibody dependent cell cytotoxicity). An IgG4 will be preferred if a non-cytotoxic blocking antibody is required. However, IgG4 antibodies can demonstrate instability in production and therefore it may be more preferable to modify the generally more stable IgG1. Suggested modifications are described in EP0307434 preferred modifications include at positions 235 and 237. The invention therefore provides a lytic or a non-lytic form of an antibody according to the invention.

In one embodiment the antibody of the invention is a full length (i.e. a tetramer comprising two heavy and two light chains) non-lytic IgG1 antibody having the VH or VL sequences described supra. In another embodiment we provide a full length non-lytic IgG1 antibody having the VHs of SEQ ID NOs 11, 12, 16, 18 or 85, 86, 87 or 91; and VLs of SEQ ID NOs 20, 23 or 25.

In a further aspect, the invention provides polynucleotides encoding the disclosed heavy or light chains or variable regions. For example the invention provides polynucleotides encoding VH having the sequence contained in SEQ ID NOs 45-52, 99-105 and VL regions having the sequence contained in SEQ ID NOs 53-59.

"NOGO" refers to any NOGO polypeptide, including variant forms. This includes, but is not limited to, NOGO-A having 1192 amino acid residues (GenBank accession no. AJ251383); NOGO-B, a splice variant which lacks residues 186 to 1004 in the putative extracellular domain (GenBank accession no. AJ251384) and a shorter splice variant, NOGO-C, which also lacks residues 186 to 1004 and also has smaller, alternative amino terminal domain (GenBank accession no. AJ251385) (Prinjha et al (2000) supra). All references to "NOGO" herein is understood to include any and all variant forms of NOGO such as NOGO-A and the splice variants described, unless a specific form is indicated.

"Neutralising" and grammatical variations thereof refers to inhibition, either total or partial, of NOGO function including its binding to neurones and inhibition of neurite growth.

"Altered antibody" refers to a protein encoded by an altered immunoglobulin coding region, which may be obtained by expression in a selected host cell. Such altered antibodies include engineered antibodies (e.g., chimeric, reshaped, humanized or vectored antibodies) or antibody fragments lacking all or part of an immunoglobulin constant region, e.g., Fv, Fab, or F(ab)2 and the like.

"Altered immunoglobulin coding region" refers to a nucleic acid sequence encoding altered antibody. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

As used herein, an "engineered antibody" describes a type of altered antibody, i.e., a full-length synthetic antibody (e.g., a chimeric, reshaped or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

A "functional fragment" is a partial heavy or light chain variable sequence (e.g., minor deletions at the amino or carboxy terminus of the immunoglobulin variable region) which retains the same antigen binding specificity and the same or similar neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence.

Analogs may also arise as allelic variations. An "allelic variation or modification" is an alteration in the nucleic acid sequence. Such variations or modifications may be due to degeneracy in the genetic code or may be deliberately engineered to provide desired characteristics. These variations or modifications may or may not result in alterations in any encoded amino acid sequence.

The present invention also includes the use of Fab fragments or F(ab')$_2$ fragments derived from mAbs of the present invention directed against NOGO. A Fab fragment contains the entire light chain and amino terminal portion of the heavy chain; and an F(ab')$_2$ fragment is the fragment formed by two Fab fragments bound by disulfide bonds. Fab fragments and F(ab')$_2$ fragments can be obtained by conventional means, e.g., cleavage of mAb with the appropriate proteolytic enzymes, papain and/or pepsin, or by recombinant methods. The Fab and F(ab')$_2$ fragments are useful themselves as therapeutic or prophylactic, and as donors of sequences including the variable regions and CDR sequences useful in the formation of recombinant or humanized antibodies as described herein.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an anti-NOGO antibody, preferably a high affinity antibody, inserted into a first immunoglobulin partner (a human framework or human immunoglobulin variable region).

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of NOGO may be designed to elicit enhanced binding.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art. In further aspects of the invention we provide diabodies (bivalent or bispecific), triabodies, tetrabodies and other multivalent scFV protein species having one or more CDRs as described supra that bind to and neutralise NOGO function.

In still a further embodiment, the antibody of the invention may have attached to it an additional agent. For example, the procedure of recombinant DNA technology may be used to produce an engineered antibody of the invention in which the Fc fragment or CH2-CH3 domain of a full length antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having the antigen specificity of anti-NOGO antibody. The resulting protein may exhibit both anti-NOGO antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a full length antibody molecule, having full length heavy and light chains, or any discrete fragment thereof, such as the Fab or F(ab')$_2$ fragments, a heavy chain dimer, or any minimal recombinant fragments thereof such as an Fv or a single-chain antibody (SCA) or any other molecule with the same specificity as the selected donor mAb. Such protein may be used in the form of an altered antibody, or may be used in its unfused form.

Whenever the second immunoglobulin partner is derived from an antibody different from the donor antibody, e.g. any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the anti-NOGO mAb or one or more of the heavy or light chain CDRs. The engineered antibodies may be neutralising, as above defined.

In addition, the constant region may be altered to enhance or decrease selective properties of the molecules of the instant invention. For example, dimerization, binding to Fc receptors, or the ability to bind and activate complement (see, e.g., Angal et al., Mol. Immunol, 30:105-108 (1993), Xu et al., J. Biol. Chem, 269:3469-3474 (1994), Winter et al., EP 307, 434-B).

The antibodies of the present invention may be produced by making a conventional expression vector or recombinant plasmid by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The antibody which includes the association of both the recombinant heavy chain and/or light chain is screened from culture by appropriate assay, such as ELISA or RIA. Similar conventional techniques may be employed to construct other altered antibodies and molecules.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Swedeny. Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the antibodies may be selected by one of skill in the art from any conventional vector. The vectors also contain selected regulatory sequences (such as CMV or RSV promoters) which direct the replication and expression of heterologous DNA sequences in selected host cells. These vectors contain the above described DNA sequences which code for the antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the antibody of the invention are preferably mammalian cells such as NS0, Sp2/0, CHO (e.g. DG44), COS, a fibroblast cell (e.g., 3T3), and myeloma cells, and more preferably a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Pluckthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antibody of the invention from such host cell are all conventional techniques. Typically, the culture method of the present invention is a serum-free culture method, usually by culturing cells serum-free in suspension. Likewise, once produced, the antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of altered antibodies are described in WO 99/58679 and WO 96/16990.

Yet another method of expression of the antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

In a further aspect of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an anti-NOGO antibody which specifically binds to and neutralises the activity of human NOGO-A which method comprises the steps of;

(a) providing a first vector encoding a heavy chain of the antibody;

(b) providing a second vector encoding the light chain of the antibody;

(c) tranforming a mammalian host cell (e.g. CHO) with said first and second vectors;

(d) culturing the host cell of step (c) under conditions conducive to the secretion of the antibody from said host cell into said culture media;

(e) recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to NOGO. Additionally, other in vitro assays may also be used to verify neutralizing efficacy prior to subsequent human clinical studies performed to evaluate the persistence of the antibody in the body despite the usual clearance mechanisms.

The therapeutic agents of this invention may be administered as a prophylactic or following the stroke event/on-set of clinical symptoms, or as otherwise needed. The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) maybe required to achieve maximal therapeutic efficacy.

The mode of administration of the therapeutic agent of the invention may be any suitable route which delivers the agent to the host. The antagonists and antibodies, and pharmaceutical compositions of the invention are particularly useful for parenteral administration, i.e., subcutaneously, intrathecally, intraperitoneally, intramuscularly, intravenously, or intranasally, of which intravenously is particularly preferred.

Therapeutic agents of the invention may be prepared as pharmaceutical compositions containing an effective amount of the antagonist or antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the antagonist or antibody of the invention or a cocktail thereof dissolved in a pharmaceutically acceptable carrier, preferably an aqueous carrier. A variety of aqueous carriers may be employed, e.g., 0.9% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antagonist or antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antagonist or antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antibody formulations of the invention see Lasmar U and Parkins D "The formulation of Biopharmaceutical products", Pharma. Sci. Tech. today, page 129-137, Vol. 3 ($3^{rd}$ Apr. 2000), Wang, W "Instability, stabilisation and formulation of liquid protein pharmaceuticals", Int. J. Pharm 185 (1999) 129-188, Stability of Protein Pharmaceuticals Part A and B ed Ahern T. J., Manning M. C., New York, N.Y.: Plenum Press (1992), Akers, M. J. "Excipient-Drug interactions in Parenteral Formulations", J. Pharm Sci 91 (2002) 2283-2300, Imamura, K et al "Effects of types of sugar on stabilization of Protein in the dried state", J Pharm Sci 92 (2003) 266-274, Izutsu, Kkojima, S. "Excipient crystalinity and its protein-structure-stabilizing effect during freeze-drying", J. Pharm. Pharmacol, 54 (2002) 1033-1039, Johnson, R, "Mannitol-sucrose mixtures-versatile formulations for protein lyophilization", J. Pharm. Sci, 91 (2002) 914-922.

Ha, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

It is preferred that the therapeutic agent of the invention, when in a pharmaceutical preparation, be present in unit dose forms. The appropriate therapeutically effective dose can be determined readily by those of skill in the art. To effectively treat stroke and other neurological diseases in a human, one dose of up to 700 mg per 70 kg body weight of an antagonist or antibody of this invention should be administered parenterally, preferably i.v. or i.m. (intramuscularly). Such dose may, if necessary, be repeated at appropriate time intervals selected as appropriate by a physician. As disclosed in the examples, the present inventors have been able to demonstrate a positive effect on functional recovery in the rat model therein when antibodies of the invention were administered intravenously.

The antibodies described herein can be lyophilized for storage and reconstituted in a suitable carrier prior to use. This technique has been shown to be effective with conventional immunoglobulins and art-known lyophilization and reconstitution techniques can be employed.

Antibodies of the invention may also be used in combination (i.e. simultaneously, sequentially or separately) with a neurotrophic factor such as nerve growth factor (NGF), for example brain derived neurotrophic factor (BDNF), anti-inflammatory agents such as corticosteroids, and/or tPA. Combinations of a NOGO antibody of the invention and e.g. tPA maybe assessed in the MCAO model set forth in the examples below.

In another aspect, the invention provides a pharmaceutical composition comprising anti-NOGO antibody of the present invention or a functional fragment thereof and a pharmaceutically acceptable carrier for treatment or prophylaxis of stroke and other neurological diseases.

In a yet further aspect, the invention provides a pharmaceutical composition comprising the anti-NOGO antibody of the present invention or a functional fragment thereof and a pharmaceutically acceptable carrier for inhibiting neurodegeneration and/or promoting functional recovery in a human patient suffering, or at risk of developing, a stroke or other neurological disease.

The invention further provides a method of treatment or prophylaxis of stroke (particularly ischemic stroke) and other neurological diseases/disorders, in particular Alzheimer's disease, in a human which comprises administering to said human in need thereof an effective amount of an anti-NOGO antibody or a functional fragment thereof. Antibodies of the invention may be used in methods of treatment to slow or halt the progression and/or onset of Alzheimer's disease in addition to (or as an alternative to) treating established disease in a human patient.

Further the invention provides the use of an anti-NOGO antibody, or a functional fragment thereof, in the preparation of a medicament for treatment or prophylaxis of stroke and other neurological diseases/disorders, in particular Alzheimer's disease.

The invention also provides a method of inhibiting neurodegeneration and/or promoting functional recovery in a human patient suffering, or at risk of developing, a stroke or other neurological disease/disorder, in particular Alzheimer's disease, which comprises administering to said human in need thereof an effective amount of an anti-NOGO antibody or a functional fragment thereof.

In addition the invention provides the use of an anti-NOGO antibody or a functional fragment thereof in the preparation of a medicament for inhibiting neurodegeneration and/or promoting functional recovery in a human patient afflicted with, or at risk of developing, a stroke and other neurological disease/disorder, in particular Alzheimer's disease.

The invention further provides a method of treating or prophylaxis of stroke or other neurological disease/disorder, in particular Alzheimer's disease, in a human comprising the step of parenteral administration of a therapeutically effective amount of an anti-NOGO antibody. Preferably the anti-NOGO antibody is administered intravenously.

Neurological diseases or disorders as used hereinabove includes, but is not limited to traumatic brain injury, spinal cord injury, fronto-temporal dementias (tauopathies), peripheral neuropathy, Parkinson's disease, Huntington's disease, multiple sclerosis and in particular Alzheimer's disease.

The invention also provides a method of promoting axonal sprouting comprising the step of contacting a human axon with an anti-NOGO antibody. This method may be performed in-vitro or in-vivo, preferably the method is performed in-vivo.

In a further aspect therefore there is provided the use of an anti-NOGO antibody or functional fragment thereof of the invention comprising CDR's of table 1 and 2; CDR's of Table 3 and 4; or CDR's of table 5 and 6 in intravenously administrable form in the manufacture of a medicament for the treatment of stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient.

In a further aspect therefore there is provided a method of treating stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient which method comprises the intravenous administration of a therapeutically effective amount of an anti-NOGO antibody of the invention.

In a further aspect of the present invention there is provided a method of promoting axon sprouting of neurons within the central nervous system of a human subject (e.g. patient) which method comprises administering (e.g. intravenously administering) a therapeutically effective amount of an anti-NOGO antibody (e.g. an anti-NOGO antibody comprising CDRs as set forth herein).

In a further aspect of the present invention there is provided the use of an anti-NOGO antibody (e.g. an anti-NOGO antibody comprising the CDRs set forth herein) in the manufacture of an intravenously administrable medicament for the treatment of stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient.

In a further aspect of the invention there is provided a method of regenerating axon processes in neurons of the central nervous system in a human patient afflicted with (or susceptible to) stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease which method comprises the step of administering (e.g. intravenously) a therapeutically effective amount of an anti-NOGO antibody (e.g. an anti-NOGO antibody having the CDRs set forth herein).

In a further aspect of the invention there is provided the use of an anti-NOGO antibody (e.g. an anti-NOGO antibody having the CDRs set forth herein) in the manufacture of an intravenously administrable pharmaceutical composition for regenerating axon processes in neurons of the central nervous system in a human patient afflicted with (or susceptible to) stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease.

In a further aspect of the invention there is provided a method of modulating the production of an amyloidogenic peptide comprising contacting a cell which is expressing the precursor from which the amyloidogenic peptide is derived and a NOGO polypeptide (e.g. human NOGO-A) with an anti-NOGO antibody (e.g. an anti-NOGO antibody comprising the CDRs set forth herein, particularly 2A10 and fully human or humanised versions thereof). In typical embodiments, the precursor is APP. In further typical embodiments the amyloidogenic peptide is Aβ, most preferably Aβ40, Aβ42 or a combination of both.

As used herein, the term "functional recovery" refers to a motor and/or sensory and/or behavioural improvement in a subject following e.g. an ischemic event or injury or on-set of clinical symptoms. Functional recovery in humans may be evaluated by instruments designed to measure elemental neurological functions such as motor strength, sensation and coordination, cognitive functions such as memory, language and the ability to follow directions, and functional capacities such as basic activities of daily living or instrumental activities. Recovery of elemental neurological function can be measured with instruments such as the NIH Stroke Scale (NIHSS), recovery of cognitive function can be measured with neuropsychological tests such as Boston Naming Test, Trail-making Tests, and California Verbal Learning Test, and activities of daily living may be measured with instruments such as the ADCS/ADL (Alzheimer's Disease Clinical Studies/Activities of Daily Living) scale or the Bristol Activities of Daily Living Scale, all tests and scales known in the art.

EXAMPLE 1

Construction and Expression of Humanised Anti-NOGO Antibodies

Murine and Humanised $V_H$ and $V_L$ constructs were prepared de novo by build up of overlapping oligonucleotides including restriction sites for cloning into Rld and Rln mammalian expression vectors as well as a human signal sequence. Hind III and Spe I restriction sites were introduced to frame the $V_H$ domain containing the CAMPATH-1H signal sequence for cloning into Rld containing the human γ1 mutated constant region. Hind III and BsiWI restriction sites were introduced to frame the $V_L$ domain containing the CAMPATH-1H signal sequence for cloning into Rln containing the human kappa constant region.

CAMPATH-1H signal sequence: MGWSCIILFLVATAT-GVHS (SEQ.I.D.NO:82)

In parallel a chimeric version of 11C7 was generated (see WO04/052932). The variable heavy domain sequence (derived from WO04/052932 Seq ID 43) and variable light domain sequence (derived from WO04/052932 Seq ID 44) were prepared de novo by build up of overlapping oligonucleotides. Hind III and SpeI restriction sites were introduced to frame the $V_H$ domain for cloning into Rld containing the human γ1 mutated constant region. HindIII and BsiWI restriction sites were introduced to frame the $V_L$ domain for cloning into Rln containing the human kappa constant region.

EXAMPLE 2

Antibody Expression in CHO Cells

Rld and Rln plasmids encoding the heavy and light chains respectively were transiently co-transfected into CHO cells and expressed at small scale or large scale to produce antibody. Alternatively the same plasmids were co-transfected into CHO cells by electroporation and a stable polyclonal population of cells expressing the appropriate antibody were selected using a nucleoside-free media. Recombinant antibody was recovered and purified by affinity chromatography on Protein A sepharose.

EXAMPLE 3

Humanised Anti-NOGO Antibody Binds to NOGO

GST-human NOGO-A56 (SEQ ID: 76) at 1 µg/ml in PBS was coated onto Nunc Immunosorp plates (100 µl per well) at 4° C. overnight. Wells were rinsed once with TBS+0.05% Tween (TBST) then incubated with 2% BSA in TBST to block non-specific binding sites at room temperature for 1 hour. Antibodies were diluted in TBST+2% BSA to 10 µg/ml and 1/2 dilutions made from this. Antibodies were added to wells in duplicate and incubated at room temperature for 1 hour. Wells were washed three times with TBST then incubated with anti-human kappa peroxidase conjugate (1:2000) for 1 hour. The wells were washed three times with TBST and then incubated with 100 µl OPD peroxidase substrate (Sigma) per well for 10 minutes. The colour reaction was stopped by the addition of 25 µl concentrated $H_2SO_4$. Optical density at 490 nm was measured using a plate reader. Background values read from wells with no antibody were subtracted.

FIGS. 1-5 illustrate the dose-dependent binding of humanised antibodies in comparison with the chimera (termed HcLc which is the chimera of 2A10 (comprising the 2A10 murine VH (SEQ ID NO. 7) and VL (SEQ ID NO.8) and human IgG constant regions)) to human NOGO-A56 (see Example 6 for details) in an ELISA assay. The Y-axis shows the measured optical density (OD) at 490 nm, a quantitative measure of antibody captured in the wells. The X-axis shows the concentration of antibody used (mcg/ml) per well at each data point.

The antibody material used in FIGS. 1, 3, 4 and 5 was generated from small scale transient transfections. Human IgG levels in the supernatant are quantified by ELISA (Example 4). For FIG. 2, the material used is purified antibody generated by either the polyclonal expression system or large scale transient transfections. In these cases, IgG levels were quantified by ELISA and optical density.

In another experiment, antibody material was generated from small scale transient transfections (in triplicate) for the following humanised antibodies: H16L16, H17L16, H18L16, H16L18 and the chimeric antibody HcLc. The results from this experiment are consistent with the data presented in FIGS. 1-5 with the exception of H17L16 which performed less well than shown in FIG. 1A and FIG. 2. Whilst this observation cannot be explained it should be noted that the conclusions are contradicted by another experiment with supernatant material (see FIG. 1A) and an experiment using purified H17L16 material (FIG. 2), both experiments indicated that H17L16 shows comparable binding to the other optimised variants.

EXAMPLE 4

Antibody Quantification Protocol

Nunc Immunosorp plates were coated with capture antibody H19 (goat anti-human IgG chain, Sigma #13382) at 2 µg/ml in Bicarbonate buffer (Sigma #C3041) and incubated overnight at 4° C. The plates were washed twice with TBS containing 0.05% Tween20 (TBST) and blocked with 200 µl TBST containing 2% BSA (block buffer) for 1 hr at room temperature. The plates were washed twice with TBST. Tissue culture supernatants containing antibody were titrated across the plate in 2-fold dilution steps into block buffer and incubated at room temperature for 1 hr. The plates were washed three times with TBST. HRP conjugated antibody H23 (goat anti-human kappa chain, Sigma #A7164) was diluted 1:2000 in TBST and 100 µl added to each well. The plates were incubated at room temperature for 1 hr. The plates were washed three times with TBST and developed with 100 µl of Fast-OPD substrate (Sigma #P9187). Colour was allowed to develop for 5-10 mins after which time the ELISA was stopped with 25 µl 3M $H_2SO_4$. The absorbance at 490 nM was read plate and antibody concentration determined by reference to a standard curve.

EXAMPLE 5

Antibody Competition ELISA Protocol

GST-human NOGO-A56 (SEQ ID: 76) at 0.1-1.0 µg/ml in PBS was coated onto Nunc Immunosorp plates (100 µl per well) at 4° C. overnight or at 37° C. for 1 hour. Wells were rinsed three times with PBS then incubated with 1% BSA in PBS (block buffer) to block non-specific binding sites at room temperature for 2 hours. In parallel, a 50:50 mix of antibodies was made. Murine antibody 2A10 was added to a final concentration of either 0.5 or 1.0 mcg/ml in block buffer. Chimeric antibodies (mouse variable regions cloned onto a human IgG1 Fc mutated constant region) were added to a final concentration of 0-25 mcg/ml in block buffer. The block buffer was removed from the plates and 100 µl of the 50:50 mix of antibodies was added for 1 hour at room temperature. Wells were washed three times with PBS then incubated with 100 µl of rabbit polyclonal anti-mouse immunoglobulins peroxidase conjugate (diluted 1:2000 in block buffer, DakoCytomation #P0260) for 1 hour at room temperature. The wells were washed three times with PBS and then incubated with 100 µl OPD peroxidase substrate (Sigma #P9187) or TMB substrate (Sigma #T8665) per well for 10-30 minutes. The colour reaction was stopped by the addition of 25 µl concentrated $H_2SO_4$. Optical density at 490 nm (OPD) or 450 nm (TMB) was measured using a plate reader.

In the first experiment (FIG. 7A), plates were coated with GST-human NOGO-A56 at 0.5 µg/ml in PBS overnight at 4° C. and the plates were developed with TMB substrate. In this experiment, the murine antibody 2A10 was assessed in combination with HcLc (the chimeric form of 2A10), 11C7, an isotype control chimeric antibody and a blank control. In the second experiment (FIG. 7B), plates were coated with GST-human NOGO-A56 at 0.5 µg/ml in PBS at 37° C. for 1 hour and the plates were developed with OPD substrate. In this experiment, the murine antibody 2A10 was assessed in combination with HcLc, 11C7, an isotype control and H16L18.

EXAMPLE 6

Production of NOGO-A Fragment (NOGO-A56, SEQ.I.D.NO:76)

A cDNA sequence encoding amino acids 586-785 (MQESLYPAAQLCPSFEESEATPSPVLPDIVMEAPL-NSAVPSAGASVIQPSSSPLEASSVNYESIKHEPEN-PPPYEEAMSVSLKKVSGIKEEIKEPENINAALQETEA-PYISIACDL IKETKLSAEPAPDFSDYSEMAKVEQPVP-DHSELVEDSSPDSEPVDLEFSDDSIPDVPQK QDETV-MLVKESLTETSFESMIEYENKE—SEQ.I.D.NO:76) of human NOGO-A was cloned into the BamHI-XhoI sites of pGEX-6P1 to generate a GST-tagged fusion protein designated NOGO-A56. Plasmid was expressed in BL21 cells in 2×TY medium with 100 µg/ml ampicillin following induction with IPTG to 0.5 mM at 37 C for 3 hours. Cell pellets were lysed by sonication and the fusion protein purified using Glutathione-sepharose (Amersham Pharmacia) following manufacturers instructions. Purified protein was eluted using reduced glutathione and extensively dialysed against PBS, quantitated using BSA standards and a BioRad coomassie based protein assay and then stored in aliquots at −80 C.

EXAMPLE 7

BiaCore Analysis of Humanised Anti NOGO Monoclonal Antibodies

The binding kinetics of the anti-NOGO monoclonal antibody (mAb) to recombinantly expressed human NOGO-A (GST-human NOGO-A56) was analysed using the Biacore3000 biosensor. The hNOGO-A chip was prepared as follows:

Method hNOGO (GST-human NOGO-A56) was immobilised to a CM5 chip by primary amine coupling using the Biacore Wizard program designed for targeted immobilisation levels. The CM5 sensor surface was activated by passing a solution of 50 mM N-hydroxy-succinimide (NHS) and 200 mM N-ethyl-N'-dimethylaminopropyl carbonide (EDC). Then hNOGO in sodium acetate buffer, pH5.0 or pH 4.5, was passed over the chip and immobilised. After immobilisation was complete any still activated esters were blocked by an injection of 1M ethanolamine hydrochloride, pH8.5.

The anti-NOGO mAbs were diluted down in HBS-EP (10 mM HEPES, pH 7.4, 150 mM NaCl, 3 mM EDTA, and 0.005% P-20 surfactant) and binding studies were carried out at range of defined antibody concentrations. All runs were referenced against a blanked sensor surface (one that had been activated and blocked as described earlier but had no addition of ligand). Analysis of binding was carried out using the BIAevaluation kinetic analysis software version 4.1. Biacore analysis of other antibodies of the invention essentially followed the same protocol as described herein.

TABLE 8

Results
Mean (+/−standard deviation) of four separate experiments

| Antibody | ka (1/Ms) | kd (1/s) | KD (nM) |
|---|---|---|---|
| HcLc | 2.70e6 (2.7e5) | 3.78e-3 (7.0e-4) | 1.41 (0.3) |
| H6L13 | 1.82e6 (3.5e5) | 1.37e-2 (2.0e-3) | 7.68 (1.2) |
| H16L16 | 4.37e6 (4.5e5) | 5.54e-3 (1.4e-3) | 1.26 (0.2) |
| H16L18 | 4.18e6 (4.1e5) | 5.52e-3 (9.0e-4) | 1.33 (0.2) |
| H17L16 | 3.38e6 (1.3e5) | 6.10e-3 (1.3e-3) | 1.82 (0.4) |
| H18L16 | 3.64e6 (3.5e5) | 5.86e-3 (9.0e-4) | 1.62 (0.3) |
| H1L11 | 1.73e6 (1.7e5) | 3.14e-2 (4.2e-3) | 18.6 (3.7) |

TABLE 9

Results
Results shown are from a single experiment with the exception of HcLc and H6Lc where the values shown are the mean (+/−standard deviation) of two separate experiments

| Antibody (number of independent runs) | ka (1/Ms) | kd (1/s) | KD (nM) |
|---|---|---|---|
| HcLc (2) | 3.52e6 (2.8e5) | 3.46e-3 (7.9e-4) | 0.995 (0.3) |
| HcL11 | 3.78e6 | 1.34e-2 | 3.55 |
| H6Lc (2) | 2.17e6 (3.8e5) | 2.84e-3 (1.5e-3) | 2.21 (0.3) |
| HcL13 | 4.8e6 | 9.38e-3 | 1.98 |
| H6L13 | 2.95e6 | 2.33e-2 | 7.9 |
| H6L6 | 1.2e6 | 2.54e-2 | 21.4 |
| H10L13 | 1.64e6 | 2.12e-2 | 12.95 |
| H700L11 | 1.19e6 | 2.33e-2 | 19.45 |
| H5L6 | 1.5e6 | 4.7e-2 | 30.3 |
| 11C7 | 1.44e6 | 8.25e-5 | 0.057 |

TABLE 10

Results
Results shown are from a single experiment

| Antibody | ka (1/Ms) | kd (1/s) | KD (nM) |
|---|---|---|---|
| H6L13 | 1.77e6 | 1.3e-2 | 7.3 |
| H16L16 | 5.47e6 | 5.69e-3 | 1.0 |
| H14L16 | 2.05e6 | 7.39e-3 | 3.6 |
| H14L18 | 2.41e6 | 8.69e-3 | 3.6 |
| H1L11 | 1.33e6 | 2.84e-2 | 21.3 |
| HcLc | 2.62e6 | 4.12e-3 | 1.6 |

EXAMPLE 8

BiaCore Analysis of Humanised Anti NOGO Monoclonal Antibodies Using Off-rate Ranking The hNOGO chip was prepared as for kinetic analysis. Cell supernatants where taken directly from transient transfections of CHO-K1 cells. These were passed directly over the sensor surface and the interaction measured. A mock transfected cell supernatant was used for double referencing to remove any artefacts due to the tissue culture media. All runs were referenced against a blanked sensor surface (one that had been activated and blocked as described earlier but had no addition of ligand). Analysis of binding was carried out using the BIAevaluation kinetic analysis software version 4.1.

TABLE 11

Results
Results shown are from a single experiment with the exception of H6L13, H16L16, H16L18, H1L11, HcLc and H18L16 where the values shown are the mean (+/−standard deviation) of two or three separate experiments

| Antibody (number of independent runs) | kd (1/s) |
|---|---|
| H14L13 | 1.38e-2 |
| H15L13 | 9.65e-3 |
| H16L13 | 9.07e-3 |
| H17L13 | 9.31e-3 |
| H18L13 | 9.07e-3 |
| H6L13 (×3) | 1.73e-2 (4.8e-3) |
| H16L16 (×3) | 6.64e-3 (9.2e-4) |
| H16L18 (×3) | 6.09e-3 (7.4e-4) |
| H1L11 (×3) | 4.03e-2 (1.8e-2) |
| HcLc (×2) | 3.76e-3 (7.1e-4) |
| H15L16 | 6.04e-3 |
| H14L16 | 8.9e-3 |
| H18L16 (×2) | 6.87e-3 (7.5e-4) |
| H14L18 | 8.35e-3 |
| H15L18 | 5.94e-3 |
| H18L18 | 5.8e-3 |
| H6L17 | 1.58e-2 |
| H6L18 | 1.06e-2 |
| H6L14 | 4.57e-2 |
| H6L15 | 2.11e-2 |
| H6L16 | 1.14e-2 |

EXAMPLE 9

FACS Analysis of Humanised Anti NOGO Monoclonal Antibodies

IMR32 human neuroblastoma cells were re-suspended in FACS staining buffer (PBS+4% heat inactivated FCS) at a density of $10^6$ cells per ml. 100 µl of this suspension was transferred to wells of a 96 well round bottomed microplate. 100 µl of "Fix & Perm" Medium A (Caltag Laboratories, GAS001S-100) was added to each well and the plate incubated at room temperature for 15 mins. The cells were pelleted was washed twice in FACS staining buffer. Following washing, the cells were re-suspended in 50 µl of a solution of the anti-NOGO antibodies or an isotype matched control antibody at a concentration of 2× the final concentration (0-200 µg/ml in FACS staining buffer). 50 µl of "Fix & Perm" Medium B (Caltag Laboratories GAS002S-100) was added and the plate incubated on ice for 1 hour. Cells were washed twice in FACS staining buffer before being re-suspended in 100 µl of a solution of a PE conjugated anti human γ1 specific goat F(ab')2 (Sigma P-8047) at a dilution of 1/50. Cells incubated for 1 hour on ice. The cells were pelleted and washed 3 times in FACs staining buffer and cells re-suspended in 100 µl the same buffer. 100 µl of "Fix & Perm" Medium B was added to fix the cells. The degree of staining was determined by flow cytometry using a Becton Dickinson FACScan flow cytometer. The isotype matched controls were used as reference.

Results are shown in FIG. 6 A to F. The totality of the data shown illustrates that the HcLc antibody (of 2A10) gives a strong signal in this FACS assay, which indicates strong binding to human cell expressed NOGO. The data also shows that humanised versions of this chimera can retain this property. The 2A10 chimeric antibody, and the best humanised versions, thereof consistently outperform 11C7 in this assay.

TABLE 12

NOGO antibody sequences Summary

| | Sequence identifier (SEQ.I.D.NO) | |
|---|---|---|
| Description | amino acid sequence | Polynucleotide sequence |
| 2A10, CDR-H1 | 1 | — |
| 2A10, CDR-H2 | 2 | — |
| 2A10, CDR-H3 | 3 | — |
| 2A10, CDR-L1 | 4 | — |
| 2A10, CDR-L2 | 5 | — |
| 2A10, CDR-L3 | 6 | — |
| 2A10, VH (murine) | 7 | 41 |
| 2A10, VL (murine) | 8 | 42 |
| Chimeric heavy chain Hc | 9 | 43 |
| Chimeric light chain Lc | 10 | 44 |
| 2A10 VH humanised construct H5 | 11 | 45 |
| 2A10 VH humanised construct H6 | 12 | 46 |
| 2A10 VH humanised construct H700 | 13 | 47 |
| 2A10 VH humanised construct H14 | 14 | 48 |
| 2A10 VH humanised construct H15 | 15 | 49 |
| 2A10 VH humanised construct H16 | 16 | 50 |
| 2A10 VH humanised construct H17 | 17 | 51 |
| 2A10 VH humanised construct H18 | 18 | 52 |
| 2A10 VL humanised construct L6 | 19 | 53 |
| 2A10 VL humanised construct L13 | 20 | 54 |
| 2A10 VL humanised construct L14 | 21 | 55 |
| 2A10 VL humanised construct L15 | 22 | 56 |
| 2A10 VL humanised construct L16 | 23 | 57 |
| 2A10 VL humanised construct L17 | 24 | 58 |
| 2A10 VL humanised construct L18 | 25 | 59 |
| 2A10 heavy chain humanised construct H5 | 26 | 60 |
| 2A10 heavy chain humanised construct H6 | 27 | 61 |
| 2A10 heavy chain humanised construct H700 | 28 | 62 |
| 2A10 heavy chain humanised construct H14 | 29 | 63 |
| 2A10 heavy chain humanised construct H15 | 30 | 64 |
| 2A10 heavy chain humanised construct H16 | 31 | 65 |
| 2A10 heavy chain humanised construct H17 | 32 | 66 |
| 2A10 heavy chain humanised construct H18 | 33 | 67 |
| 2A10 light chain humanised construct L6 | 34 | 68 |
| 2A10 light chain humanised construct L13 | 35 | 69 |
| 2A10 light chain humanised construct L14 | 36 | 70 |
| 2A10 light chain humanised construct L15 | 37 | 71 |
| 2A10 light chain humanised construct L16 | 38 | 72 |
| 2A10 light chain humanised construct L17 | 39 | 73 |
| 2A10 light chain humanised construct L18 | 40 | 74 |
| Campath leader sequence | 75 | — |
| Amino acids 586–785 of human NOGO A (NOGO-A56) | 76 | — |
| 2A10 VH humanised construct H1 | 77 | 81 |
| 2A10 VL humanised construct L11 | 78 | 82 |
| 2A10 heavy chain humanised construct H1 | 79 | 83 |
| 2A10 light chain humanised construct L11 | 80 | 84 |
| 2A10 VH humanised construct H19 | 85 | 99 |
| 2A10 VH humanised construct H20 | 86 | 100 |
| 2A10 VH humanised construct H21 | 87 | 101 |
| 2A10 VH humanised construct H22 | 88 | 102 |

TABLE 12-continued

NOGO antibody sequences Summary

| Description | Sequence identifier (SEQ.I.D.NO) | |
|---|---|---|
| | amino acid sequence | Polynucleotide sequence |
| 2A10 VH humanised construct H23 | 89 | 103 |
| 2A10 VH humanised construct H24 | 90 | 104 |
| 2A10 VH humanised construct H25 | 91 | 105 |
| 2A10 heavy chain humanised construct H19 | 92 | 106 |
| 2A10 heavy chain humanised construct H20 | 93 | 107 |
| 2A10 heavy chain humanised construct H21 | 94 | 108 |
| 2A10 heavy chain humanised construct H22 | 95 | 109 |
| 2A10 heavy chain humanised construct H23 | 96 | 110 |
| 2A10 heavy chain humanised construct H24 | 97 | 111 |
| 2A10 heavy chain humanised construct H25 | 98 | 112 |

The invention claimed is:

1. A monoclonal antibody, or functional fragment thereof, which binds to human NOGO-A comprising the heavy chain variable region of SEQ ID NO: 77 with the exception that at least one amino acid residue from positions 12, 20, 38, 40, 48, 67, 68, 70, 72, 74, 76, 79 and 91 is substituted with the positionally equivalent amino acid residue from SEQ ID NO: 7.

2. The monoclonal antibody as claimed in claim 1, wherein the antibody comprises an amino acid substitution at position 79.

3. The monoclonal antibody as claimed in claim 2, wherein the antibody sequence further comprises amino acid substitutions at positions 48 and 68.

4. The monoclonal antibody as claimed in claim 2, wherein the antibody sequence further comprises amino acid substitution(s) at positions 40 and/or 67.

5. The monoclonal antibody as claimed in claim 4, wherein the antibody sequence further comprises amino acid substitution(s) at positions 38 and/or 72 and/or 70.

6. The monoclonal antibody as claimed in claim 5, wherein the antibody sequence further comprises amino acid substitution(s) at one or more of positions 12, 20, 74, 76 and 91.

7. The monoclonal antibody as claimed in claim 1 wherein the heavy chain variable region has a sequence selected from SEQ ID NO: 11-18, 29-33 and 85-91.

8. The monoclonal antibody as claimed in claim 7, wherein the antibody comprises the VH region selected from SEQ ID NO: 11, 12, 16, 18, 85, 86, 87 or 91.

9. A composition comprising the anti-NOGO-A antibody or functional fragment thereof according to claim 1 together with a pharmaceutically acceptable diluent or carrier.

10. A monoclonal antibody comprising the heavy chain variable region as claimed in claim 1 in combination with a light chain variable region having the amino acid sequence of SEQ ID NO:20 with the exception that at least one amino acid residue from positions 4, 7, 11, 19, 42, 64 and 70; is substituted with the amino acid residue at the equivalent position in SEQ ID NO: 8.

11. The monoclonal antibody as claimed in claim 10, wherein the light chain variable region comprises amino acid substitution(s) at positions 11 and 19.

12. The monoclonal antibody as claimed in claim 11, wherein the light chain variable region further comprises an amino acid substitution at position 42.

13. The monoclonal antibody as claimed in claim 11, wherein the light chain variable region further comprises an amino acid substitution at positions 7, 64 or 70.

14. The monoclonal antibody as claimed in claim 10, wherein the light chain variable region comprises an amino acid substitution at position 4.

15. The monoclonal antibody as claimed in claim 10, wherein the light chain variable region is SEQ ID NO:20.

16. The monoclonal antibody as claimed in claim 10, wherein the antibody comprises the VL region provided in SEQ ID NO: 23 or 25.

17. A monoclonal antibody comprising VH and VL regions selected from the following list:

| Heavy Chain | Light Chain |
| --- | --- |
| SEQ ID NO: 77 | & SEQ ID NO: 20 |
| SEQ ID NO: 11 | & SEQ ID NO: 20 |
| SEQ ID NO: 12 | & SEQ ID NO: 20 |
| SEQ ID NO: 14 | & SEQ ID NO: 20 |
| SEQ ID NO: 15 | & SEQ ID NO: 20 |
| SEQ ID NO: 16 | & SEQ ID NO: 20 |
| SEQ ID NO: 17 | & SEQ ID NO: 20 |
| SEQ ID NO: 18 | & SEQ ID NO: 20 |
| SEQ ID NO: 85 | & SEQ ID NO: 20 |
| SEQ ID NO: 86 | & SEQ ID NO: 20 |
| SEQ ID NO: 87 | & SEQ ID NO: 20 |
| SEQ ID NO: 88 | & SEQ ID NO: 20 |
| SEQ ID NO: 89 | & SEQ ID NO: 20 |
| SEQ ID NO: 90 | & SEQ ID NO: 20 |
| SEQ ID NO: 91 | & SEQ ID NO: 20 |
| SEQ ID NO: 13 | & SEQ ID NO: 20 |
| SEQ ID NO: 77 | & SEQ ID NO: 23 |
| SEQ ID NO: 11 | & SEQ ID NO: 23 |
| SEQ ID NO: 12 | & SEQ ID NO: 23 |
| SEQ ID NO: 14 | & SEQ ID NO: 23 |
| SEQ ID NO: 15 | & SEQ ID NO: 23 |
| SEQ ID NO: 16 | & SEQ ID NO: 23 |
| SEQ ID NO: 17 | & SEQ ID NO: 23 |
| SEQ ID NO: 18 | & SEQ ID NO: 23 |
| SEQ ID NO: 85 | & SEQ ID NO: 23 |
| SEQ ID NO: 86 | & SEQ ID NO: 23 |
| SEQ ID NO: 87 | & SEQ ID NO: 23 |
| SEQ ID NO: 88 | & SEQ ID NO: 23 |
| SEQ ID NO: 89 | & SEQ ID NO: 23 |
| SEQ ID NO: 90 | & SEQ ID NO: 23 |
| SEQ ID NO: 91 | & SEQ ID NO: 23 |
| SEQ ID NO: 13 | & SEQ ID NO: 23 |
| SEQ ID NO: 77 | & SEQ ID NO: 25 |
| SEQ ID NO: 11 | & SEQ ID NO: 25 |
| SEQ ID NO: 12 | & SEQ ID NO: 25 |
| SEQ ID NO: 14 | & SEQ ID NO: 25 |
| SEQ ID NO: 15 | & SEQ ID NO: 25 |
| SEQ ID NO: 16 | & SEQ ID NO: 25 |
| SEQ ID NO: 17 | & SEQ ID NO: 25 |
| SEQ ID NO: 18 | & SEQ ID NO: 25 |
| SEQ ID NO: 85 | & SEQ ID NO: 25 |
| SEQ ID NO: 86 | & SEQ ID NO: 25 |
| SEQ ID NO: 87 | & SEQ ID NO: 25 |
| SEQ ID NO: 88 | & SEQ ID NO: 25 |
| SEQ ID NO: 89 | & SEQ ID NO: 25 |
| SEQ ID NO: 90 | & SEQ ID NO: 25 |
| SEQ ID NO: 91 | & SEQ ID NO: 25 |
| SEQ ID NO: 13 | & SEQ ID NO: 25. |

18. A monoclonal antibody as claimed in claim 17 selected from the following pairs of the list of full length antibody light and heavy chains:

| Light Chain | Heavy Chain |
| --- | --- |
| SEQ ID NO: 35 | SEQ ID NO: 26 |
| SEQ ID NO: 35 | SEQ ID NO: 27 |

-continued

| Light Chain | Heavy Chain |
|---|---|
| SEQ ID NO: 35 | SEQ ID NO: 92 |
| SEQ ID NO: 35 | SEQ ID NO: 93 |
| SEQ ID NO: 35 | SEQ ID NO: 94 |
| SEQ ID NO: 35 | SEQ ID NO: 98 |
| SEQ ID NO: 38 | SEQ ID NO: 31 |
| SEQ ID NO: 38 | SEQ ID NO: 92 |
| SEQ ID NO: 38 | SEQ ID NO: 93 |
| SEQ ID NO: 38 | SEQ ID NO: 94 |
| SEQ ID NO: 38 | SEQ ID NO: 98 |

-continued

| Light Chain | Heavy Chain |
|---|---|
| SEQ ID NO: 40 | SEQ ID NO: 31 |
| SEQ ID NO: 38 | SEQ ID NO: 33 |
| SEQ ID NO: 40 | SEQ ID NO: 92 |
| SEQ ID NO: 40 | SEQ ID NO: 93 |
| SEQ ID NO: 40 | SEQ ID NO: 94 |
| SEQ ID NO: 40 | SEQ ID NO: 98. |

\* \* \* \* \*

SEQUENCE LISTING

```
<160> NUMBER OF SEQ ID NOS: 113

<210> SEQ ID NO 1
<211> LENGTH: 5
<212> TYPE: PRT
<213> ORGANISM: Homo sapien

<400> SEQUENCE: 1

Ser Tyr Trp Met His
 1               5

<210> SEQ ID NO 2
<211> LENGTH: 17
<212> TYPE: PRT
<213> ORGANISM: Homo sapien

<400> SEQUENCE: 2

Asn Ile Asn Pro Ser Asn Gly Gly Thr Asn Tyr Asn Glu Lys Phe Lys
 1               5                  10                  15

Ser

<210> SEQ ID NO 3
<211> LENGTH: 4
<212> TYPE: PRT
<213> ORGANISM: Homo sapien

<400> SEQUENCE: 3

Gly Gln Gly Tyr
 1

<210> SEQ ID NO 4
<211> LENGTH: 16
<212> TYPE: PRT
<213> ORGANISM: Homo sapien

<400> SEQUENCE: 4

Arg Ser Ser Lys Ser Leu Leu Tyr Lys Asp Gly Lys Thr Tyr Leu Asn
 1               5                  10                  15

<210> SEQ ID NO 5
<211> LENGTH: 7
<212> TYPE: PRT
<213> ORGANISM: Homo sapien
```

```
<400> SEQUENCE: 5

Leu Met Ser Thr Arg Ala Ser
 1               5

<210> SEQ ID NO 6
<211> LENGTH: 9
<212> TYPE: PRT
<213> ORGANISM: Homo sapien

<400> SEQUENCE: 6

Gln Gln Leu Val Glu Tyr Pro Leu Thr
 1               5

<210> SEQ ID NO 7
<211> LENGTH: 113
<212> TYPE: PRT
<213> ORGANISM: Murine

<400> SEQUENCE: 7

Gln Val Gln Leu Gln Gln Pro Gly Thr Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Asn Ile Asn Pro Ser Asn Gly Gly Thr Asn Tyr Asn Glu Lys Phe
     50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Glu Leu Gly Gln Gly Tyr Trp Gly Gln Gly Thr Thr Leu Thr Val Ser
            100                 105                 110

Ser

<210> SEQ ID NO 8
<211> LENGTH: 112
<212> TYPE: PRT
<213> ORGANISM: Murine

<400> SEQUENCE: 8

Asp Ile Val Ile Thr Gln Asp Glu Leu Ser Asn Pro Val Thr Ser Gly
 1               5                  10                  15

Glu Ser Val Ser Ile Ser Cys Arg Ser Ser Lys Ser Leu Leu Tyr Lys
             20                  25                  30

Asp Gly Lys Thr Tyr Leu Asn Trp Phe Leu Gln Arg Pro Gly Gln Ser
         35                  40                  45

Pro Gln Leu Leu Ile Tyr Leu Met Ser Thr Arg Ala Ser Gly Val Ser
     50                  55                  60

Asp Arg Phe Ser Gly Ser Gly Ser Gly Thr Asp Phe Thr Leu Glu Ile
 65                  70                  75                  80

Ser Arg Val Lys Ala Glu Asp Val Gly Val Tyr Tyr Cys Gln Gln Leu
                 85                  90                  95

Val Glu Tyr Pro Leu Thr Phe Gly Ala Gly Thr Lys Leu Glu Leu Lys
            100                 105                 110

<210> SEQ ID NO 9
<211> LENGTH: 462
```

<212> TYPE: PRT
<213> ORGANISM: Homo sapien

<400> SEQUENCE: 9

```
Met Gly Trp Ser Cys Ile Ile Leu Phe Leu Val Ala Ala Ala Thr Gly
  1               5                  10                  15

Val His Ser Gln Val Gln Leu Gln Gln Pro Gly Thr Glu Leu Val Lys
             20                  25                  30

Pro Gly Ala Ser Val Lys Leu Ser Cys Lys Ala Ser Gly Tyr Thr Phe
         35                  40                  45

Thr Ser Tyr Trp Met His Trp Val Lys Gln Arg Pro Gly Gln Gly Leu
 50                  55                  60

Glu Trp Ile Gly Asn Ile Asn Pro Ser Asn Gly Thr Asn Tyr Asn
 65                  70                  75                  80

Glu Lys Phe Lys Ser Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400
```

```
Gln Pro Glu Asn Asn Tyr Lys Thr Thr Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 10
<211> LENGTH: 239
<212> TYPE: PRT
<213> ORGANISM: Homo sapien

<400> SEQUENCE: 10

Met Arg Cys Ser Leu Gln Phe Leu Gly Val Leu Met Phe Trp Ile Ser
1               5                   10                  15

Gly Val Ser Gly Asp Ile Val Ile Thr Gln Asp Glu Leu Ser Asn Pro
            20                  25                  30

Val Thr Ser Gly Glu Ser Val Ser Ile Ser Cys Arg Ser Ser Lys Ser
        35                  40                  45

Leu Leu Tyr Lys Asp Gly Lys Thr Tyr Leu Asn Trp Phe Leu Gln Arg
    50                  55                  60

Pro Gly Gln Ser Pro Gln Leu Leu Ile Tyr Leu Met Ser Thr Arg Ala
65                  70                  75                  80

Ser Gly Val Ser Asp Arg Phe Ser Gly Ser Gly Ser Gly Thr Asp Phe
                85                  90                  95

Thr Leu Glu Ile Ser Arg Val Lys Ala Glu Asp Val Gly Val Tyr Tyr
            100                 105                 110

Cys Gln Gln Leu Val Glu Tyr Pro Leu Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 11
<211> LENGTH: 113
<212> TYPE: PRT
<213> ORGANISM: Artificial Sequence
<220> FEATURE:
<223> OTHER INFORMATION: 2A10 VH humanised construct H5

<400> SEQUENCE: 11

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Asn Ile Asn Pro Ser Asn Gly Gly Thr Asn Tyr Asn Glu Lys Phe
        50                  55                  60

Lys Ser Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser
```

<210> SEQ ID NO 12
<211> LENGTH: 113
<212> TYPE: PRT
<213> ORGANISM: Artificial Sequence
<220> FEATURE:
<223> OTHER INFORMATION: 2A10 VH humanised construct H6

<400> SEQUENCE: 12

```
Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
        50                  55                  60

Lys Ser Arg Ala Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser
```

<210> SEQ ID NO 13
<211> LENGTH: 113
<212> TYPE: PRT
<213> ORGANISM: Artificial Sequence
<220> FEATURE:
<223> OTHER INFORMATION: 2A10 VH humanised construct H700

<400> SEQUENCE: 13

```
Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
        50                  55                  60

Lys Ser Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
```

-continued

```
                85                  90                  95
Glu Leu Gly Gln Gly Tyr Trp Gly Gln Gly Thr Leu Val Thr Val Ser
            100                 105                 110
Ser

<210> SEQ ID NO 14
<211> LENGTH: 113
<212> TYPE: PRT
<213> ORGANISM: Artificial Sequence
<220> FEATURE:
<223> OTHER INFORMATION: 2A10 VH humanised construct H14

<400> SEQUENCE: 14

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
50                  55                  60

Lys Ser Arg Ala Thr Leu Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 15
<211> LENGTH: 113
<212> TYPE: PRT
<213> ORGANISM: 2A10 VH humanised construct H15

<400> SEQUENCE: 15

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
50                  55                  60

Lys Ser Lys Ala Thr Leu Thr Val Asp Thr Ser Ser Ser Thr Ala Tyr
65                  70                  75                  80

Met Glu Leu Ser Ser Leu Arg Ser Glu Asp Ser Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 16
<211> LENGTH: 113
<212> TYPE: PRT
<213> ORGANISM: Artificial Sequence
<220> FEATURE:
<223> OTHER INFORMATION: 2A10 VH humanised construct H16
```

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 17
<211> LENGTH: 113
<212> TYPE: PRT
<213> ORGANISM: Artificial Sequence
<220> FEATURE:
<223> OTHER INFORMATION: 2A10 VH humanised construct H17

<400> SEQUENCE: 17

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 18
<211> LENGTH: 113
<212> TYPE: PRT
<213> ORGANISM: Artificial Sequence
<220> FEATURE:
<223> OTHER INFORMATION: 2A10 VH humanised construct H18

<400> SEQUENCE: 18

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

```
Lys Ser Lys Ala Thr Leu Thr Val Asp Lys Ser Ser Thr Ala Tyr
 65                  70                  75                  80

Met Glu Leu Ser Ser Leu Arg Ser Glu Asp Ser Ala Val Tyr Tyr Cys
                 85                  90                  95

Glu Leu Gly Gln Gly Tyr Trp Gly Gln Gly Thr Leu Val Thr Val Ser
            100                 105                 110

Ser

<210> SEQ ID NO 19
<211> LENGTH: 112
<212> TYPE: PRT
<213> ORGANISM: Artificial Sequence
<220> FEATURE:
<223> OTHER INFORMATION: 2A10 VL humanised construct L6

<400> SEQUENCE: 19

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
         35                  40                  45

Pro Gln Leu Leu Ile Tyr Leu Met Ser Thr Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gly Gly Thr Lys Val Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: 2A10 VL humanised construct L13

<400> SEQUENCE: 20

Asp Ile Val Met Thr Gln Ser Pro Leu Ser Leu Pro Val Thr Leu Gly
 1               5                  10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Gln Gln Arg Pro Gly Gln Ser
         35                  40                  45

Pro Gln Leu Leu Ile Tyr Leu Met Ser Thr Arg Ala Ser Gly Val Pro
 50                  55                  60

Asp Arg Phe Ser Gly Gly Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gln Gly Thr Lys Leu Glu Ile Lys
            100                 105                 110

<210> SEQ ID NO 21
<211> LENGTH: 112
<212> TYPE: PRT
<213> ORGANISM: Artificial Sequence
```

```
<220> FEATURE:
<223> OTHER INFORMATION: 2A10 VL humanised construct L14

<400> SEQUENCE: 21

Asp Ile Val Met Thr Gln Ser Pro Leu Ser Leu Pro Val Thr Leu Gly
 1               5                  10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: 2A10 VL humanised construct L15

<400> SEQUENCE: 22

Asp Ile Val Met Thr Gln Ser Pro Leu Ser Leu Pro Val Thr Leu Gly
 1               5                  10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: 2A10 VL humanised construct L16

<400> SEQUENCE: 23

Asp Ile Val Met Thr Gln Ser Pro Leu Ser Asn Pro Val Thr Leu Gly
 1               5                  10                  15

Gln Pro Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Pro
    50                  55                  60
```

Asp Arg Phe Ser Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: 2A10 VL humanised construct L17

<400> SEQUENCE: 24

Asp Ile Val Met Thr Gln Asp Pro Leu Ser Leu Pro Val Thr Leu Gly
1               5                   10                  15

Gln Pro Ala Ser Ile Ser Cys Arg Ser Ser Lys Ser Leu Leu Tyr Lys
                20                  25                  30

Asp Gly Lys Thr Tyr Leu Asn Trp Phe Gln Gln Arg Pro Gly Gln Ser
            35                  40                  45

Pro Gln Leu Leu Ile Tyr Leu Met Ser Thr Arg Ala Ser Gly Val Ser
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 25
<211> LENGTH: 112
<212> TYPE: PRT
<213> ORGANISM: Artificial Sequence
<220> FEATURE:
<223> OTHER INFORMATION: 2A10 VL humanised construct L18

<400> SEQUENCE: 25

Asp Ile Val Met Thr Gln Asp Pro Leu Ser Asn Pro Val Thr Leu Gly
1               5                   10                  15

Gln Pro Val Ser Ile Ser Cys Arg Ser Ser Lys Ser Leu Leu Tyr Lys
                20                  25                  30

Asp Gly Lys Thr Tyr Leu Asn Trp Phe Leu Gln Arg Pro Gly Gln Ser
            35                  40                  45

Pro Gln Leu Leu Ile Tyr Leu Met Ser Thr Arg Ala Ser Gly Val Ser
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 26
<211> LENGTH: 462
<212> TYPE: PRT
<213> ORGANISM: Artificial Sequence
<220> FEATURE:
<223> OTHER INFORMATION: 2A10 heavy chain humanised construct H5

<400> SEQUENCE: 26

```
Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Arg Gln Ala Pro Gly Gln Gly Leu
     50                  55                  60

Glu Trp Met Gly Asn Ile Asn Pro Ser Asn Gly Gly Thr Asn Tyr Asn
 65                  70                  75                  80

Glu Lys Phe Lys Ser Arg Val Thr Met Thr Arg Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

```
Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 27
<211> LENGTH: 462
<212> TYPE: PRT
<213> ORGANISM: Artificial Sequence
<220> FEATURE:
<223> OTHER INFORMATION: 2A10 heavy chain humanised construct H6

<400> SEQUENCE: 27

Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Arg Gln Ala Pro Gly Gln Gly Leu
     50                  55                  60

Glu Trp Ile Gly Asn Ile Asn Pro Ser Asn Gly Gly Thr Asn Tyr Asn
 65                  70                  75                  80

Glu Lys Phe Lys Ser Arg Ala Thr Met Thr Arg Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320
```

```
Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
                370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
                450                 455                 460

<210> SEQ ID NO 28
<211> LENGTH: 462
<212> TYPE: PRT
<213> ORGANISM: Artificial Sequence
<220> FEATURE:
<223> OTHER INFORMATION: 2A10 heavy chain humanised construct H700

<400> SEQUENCE: 28

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Ser Tyr Trp Met His Trp Val Arg Gln Ala Pro Gly Gln Gly Leu
                50                  55                  60

Glu Trp Ile Gly Asn Ile Asn Pro Ser Asn Gly Gly Thr Asn Tyr Asn
65                  70                  75                  80

Glu Lys Phe Lys Ser Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
                100                 105                 110

Tyr Tyr Cys Glu Leu Gly Gln Gly Tyr Trp Gly Gln Gly Thr Leu Val
                115                 120                 125

Thr Val Ser Ser Ala Ser Thr Lys Gly Pro Ser Val Phe Pro Leu Ala
                130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Gln Thr Tyr Ile Cys Asn Val Asn His Lys Pro Ser Asn Thr
                210                 215                 220
```

```
Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 29
<211> LENGTH: 462
<212> TYPE: PRT
<213> ORGANISM: Artificial Sequence
<220> FEATURE:
<223> OTHER INFORMATION: 2A10 heavy chain humanised construct H14

<400> SEQUENCE: 29

Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Ala Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Arg Ala Thr Leu Thr Arg Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125
```

```
Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 30
<211> LENGTH: 462
<212> TYPE: PRT
<213> ORGANISM: Artificial Sequence
<220> FEATURE:
<223> OTHER INFORMATION: 2A10 heavy chain humanised construct H15

<400> SEQUENCE: 30

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Val Lys
            20                  25                  30
```

```
Pro Gly Ala Ser Val Lys Leu Ser Cys Lys Ala Ser Gly Tyr Thr Phe
            35                  40                  45
Thr Ser Tyr Trp Met His Trp Val Lys Gln Arg Pro Gly Gln Gly Leu
     50                  55                  60
Glu Trp Ile Gly Asn Ile Asn Pro Ser Asn Gly Thr Asn Tyr Asn
 65                  70                  75                  80
Glu Lys Phe Lys Ser Lys Ala Thr Leu Thr Val Asp Thr Ser Ser
                 85                  90                  95
Thr Ala Tyr Met Glu Leu Ser Ser Leu Arg Ser Glu Asp Ser Ala Val
            100                 105                 110
Tyr Tyr Cys Glu Leu Gly Gln Gly Tyr Trp Gly Gln Gly Thr Leu Val
            115                 120                 125
Thr Val Ser Ser Ala Ser Thr Lys Gly Pro Ser Val Phe Pro Leu Ala
        130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
    210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Ala Gly Ala Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
```

```
Asn His Tyr Thr Gln Lys Ser Leu Ser Leu Ser Pro Gly Lys
    450                 455                 460
```

<210> SEQ ID NO 31
<211> LENGTH: 462
<212> TYPE: PRT
<213> ORGANISM: Artificial Sequence
<220> FEATURE:
<223> OTHER INFORMATION: 2A10 heavy chain humanised construct H16

<400> SEQUENCE: 31

```
Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Lys Gln Arg Pro Gly Gln Gly Leu
     50                  55                  60

Glu Trp Ile Gly Asn Ile Asn Pro Ser Asn Gly Gly Thr Asn Tyr Asn
 65                  70                  75                  80

Glu Lys Phe Lys Ser Lys Ala Thr Leu Thr Val Asp Lys Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350
```

```
Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 32
<211> LENGTH: 462
<212> TYPE: PRT
<213> ORGANISM: Artificial Sequence
<220> FEATURE:
<223> OTHER INFORMATION: 2A10 heavy chain humanised construct H17

<400> SEQUENCE: 32

Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255
```

```
Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 33
<211> LENGTH: 462
<212> TYPE: PRT
<213> ORGANISM: Artificial Sequence
<220> FEATURE:
<223> OTHER INFORMATION: 2A10 heavy chain humanised construct H18

<400> SEQUENCE: 33

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Glu Leu Ser Ser Leu Arg Ser Glu Asp Ser Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160
```

-continued

```
Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
        180                 185                 190

Gly Leu Tyr Ser Leu Ser Ser Val Val Thr Val Pro Ser Ser Ser Leu
    195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 34
<211> LENGTH: 238
<212> TYPE: PRT
<213> ORGANISM: Artificial Sequence
<220> FEATURE:
<223> OTHER INFORMATION: 2A10 light chain humanised construct L6

<400> SEQUENCE: 34

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Lys Ser Leu
        35                  40                  45

Leu Tyr Lys Asp Gly Lys Thr Tyr Leu Asn Trp Phe Leu Gln Arg Pro
    50                  55                  60
```

Gly Gln Ser Pro Gln Leu Leu Ile Tyr Leu Met Ser Thr Arg Ala Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 35
<211> LENGTH: 238
<212> TYPE: PRT
<213> ORGANISM: Artificial Sequence
<220> FEATURE:
<223> OTHER INFORMATION: 2A10 light chain humanised construct L13

<400> SEQUENCE: 35

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Leu Gly Gln Pro Ala Ser Ile Ser Cys Arg Ser Ser Lys Ser Leu
        35                  40                  45

Leu Tyr Lys Asp Gly Lys Thr Tyr Leu Asn Trp Phe Gln Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

```
Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 36
<211> LENGTH: 238
<212> TYPE: PRT
<213> ORGANISM: Artificial Sequence
<220> FEATURE:
<223> OTHER INFORMATION: 2A10 light chain humanised construct L14

<400> SEQUENCE: 36

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Leu Gly Gln Pro Ala Ser Ile Ser Cys Arg Ser Ser Lys Ser Leu
        35                  40                  45

Leu Tyr Lys Asp Gly Lys Thr Tyr Leu Asn Trp Phe Leu Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 37
<211> LENGTH: 238
<212> TYPE: PRT
<213> ORGANISM: Artificial Sequence
<220> FEATURE:
<223> OTHER INFORMATION: 2A10 light chain humanised construct L15

<400> SEQUENCE: 37

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30
```

```
Thr Leu Gly Gln Pro Ala Ser Ile Ser Cys Arg Ser Ser Lys Ser Leu
            35                  40                  45

Leu Tyr Lys Asp Gly Lys Thr Tyr Leu Asn Trp Phe Leu Gln Arg Pro
    50                  55                  60

Gly Gln Ser Pro Gln Leu Leu Ile Tyr Leu Met Ser Thr Arg Ala Ser
65                  70                  75                  80

Gly Val Ser Asp Arg Phe Ser Gly Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
            115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 38
<211> LENGTH: 238
<212> TYPE: PRT
<213> ORGANISM: Artificial Sequence
<220> FEATURE:
<223> OTHER INFORMATION: 2A10 light chain humanised construct L16

<400> SEQUENCE: 38

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Asn Pro Val
            20                  25                  30

Thr Leu Gly Gln Pro Val Ser Ile Ser Cys Arg Ser Ser Lys Ser Leu
            35                  40                  45

Leu Tyr Lys Asp Gly Lys Thr Tyr Leu Asn Trp Phe Leu Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
            115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 39
<211> LENGTH: 238
<212> TYPE: PRT
<213> ORGANISM: Artificial Sequence
<220> FEATURE:
<223> OTHER INFORMATION: 2A10 light chain humanised construct L17

<400> SEQUENCE: 39

Met Gly Trp Ser Cys Ile Ile Leu Phe Leu Val Ala Thr Ala Thr Gly
1               5                   10                  15

Val His Ser Asp Ile Val Met Thr Gln Asp Pro Leu Ser Leu Pro Val
            20                  25                  30

Thr Leu Gly Gln Pro Ala Ser Ile Ser Cys Arg Ser Ser Lys Ser Leu
        35                  40                  45

Leu Tyr Lys Asp Gly Lys Thr Tyr Leu Asn Trp Phe Gln Gln Arg Pro
    50                  55                  60

Gly Gln Ser Pro Gln Leu Leu Ile Tyr Leu Met Ser Thr Arg Ala Ser
65                  70                  75                  80

Gly Val Ser Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 40
<211> LENGTH: 238
<212> TYPE: PRT
<213> ORGANISM: Artificial Sequence
<220> FEATURE:
<223> OTHER INFORMATION: 2A10 light chain humanised construct L18
```

<400> SEQUENCE: 40

```
Met Gly Trp Ser Cys Ile Ile Leu Phe Leu Val Ala Thr Ala Thr Gly
 1               5                  10                 15
Val His Ser Asp Ile Val Met Thr Gln Asp Pro Leu Ser Asn Pro Val
            20                  25                  30
Thr Leu Gly Gln Pro Val Ser Ile Ser Cys Arg Ser Ser Lys Ser Leu
        35                  40                  45
Leu Tyr Lys Asp Gly Lys Thr Tyr Leu Asn Trp Phe Leu Gln Arg Pro
    50                  55                  60
Gly Gln Ser Pro Gln Leu Leu Ile Tyr Leu Met Ser Thr Arg Ala Ser
65                  70                  75                  80
Gly Val Ser Asp Arg Phe Ser Gly Ser Gly Ser Gly Thr Asp Phe Thr
                85                  90                  95
Leu Lys Ile Ser Arg Val Glu Ala Glu Asp Val Gly Val Tyr Tyr Cys
            100                 105                 110
Gln Gln Leu Val Glu Tyr Pro Leu Thr Phe Gly Gln Gly Thr Lys Leu
        115                 120                 125
Glu Ile Lys Arg Thr Val Ala Ala Pro Ser Val Phe Ile Phe Pro Pro
    130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235
```

<210> SEQ ID NO 41
<211> LENGTH: 339
<212> TYPE: DNA
<213> ORGANISM: Murine

<400> SEQUENCE: 41

```
caggtccaac tgcagcagcc tgggactgaa ctggtgaagc ctggggcttc agtgaagctg      60
tcctgcaagg cttctggcta caccttcacc agctactgga tgcactgggt gaagcagagg     120
cctggacaag gccttgagtg gattggaaat attaatccta gcaatggtgg tactaactac     180
aatgagaagt tcaagagcaa ggccacactg actgtagaca atcctccag cacagcctac      240
atgcagctca gcagcctgac atctgaggac tctgcggtct attattgtga actgggacag     300
ggctactggg gccaaggcac cactctcaca gtctcctca                            339
```

<210> SEQ ID NO 42
<211> LENGTH: 336
<212> TYPE: DNA
<213> ORGANISM: Murine

<400> SEQUENCE: 42

```
gatattgtga taacccagga tgaactctcc aatcctgtca cttctggaga atcagtttcc      60
atctcctgca ggtctagtaa gagtctccta tataaggatg gaagacata cttgaattgg     120
```

| | |
|---|---:|
| tttctgcaga gaccaggaca atctccctcag ctcctgatct atttgatgtc cacccgtgca | 180 |
| tcaggagtct cagaccggtt tagtggcagt gggtcaggaa cagatttcac cctggaaatc | 240 |
| agtagagtga aggctgagga tgtgggtgtg tattactgtc aacaacttgt agagtatccg | 300 |
| ctcacgttcg gtgctgggac caagctggag ctgaaa | 336 |

<210> SEQ ID NO 43
<211> LENGTH: 1389
<212> TYPE: DNA
<213> ORGANISM: Artificial Sequence
<220> FEATURE:
<223> OTHER INFORMATION: PN encoding Chimeric heavy chain Hc SEQ ID: 9

<400> SEQUENCE: 43

| | |
|---|---:|
| atgggatgga gctgtatcat cctcttttg gtagcagcag ctacaggtgt ccactcccag | 60 |
| gtccaactgc agcagcctgg gactgaactg gtgaagcctg ggcttcagt gaagctgtcc | 120 |
| tgcaaggctt ctggctacac cttcaccagc tactggatgc actgggtgaa gcagaggcct | 180 |
| ggacaaggcc ttgagtggat tggaaatatt aatcctagca tggtggtac taactacaat | 240 |
| gagaagttca gagcaaggc cacactgact gtagacaaat cctccagcac agcctacatg | 300 |
| cagctcagca gcctgacatc tgaggactct gcggtctatt attgtgaact gggacagggc | 360 |
| tactggggcc aaggcacact agtcacagtc tcctcagcct ccaccaaggg cccatcggtc | 420 |
| ttccccctgg caccctcctc aagagcacc tctgggggca gcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg gggcaccgt cagtcttcct cttcccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |
| aatgccaaga caaagccgcg ggaggagcag tacaacagca cgtaccgtgt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaaagggca gccccgagaa | 1080 |
| ccacaggtgt acaccctgcc cccatcccgg gatgagctga ccaagaacca ggtcagcctg | 1140 |
| acctgcctgg tcaaaggctt ctatcccagc gacatcgccg tggagtggga gagcaatggg | 1200 |
| cagccggaga caactacaa gaccacgcct cccgtgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 44
<211> LENGTH: 720
<212> TYPE: DNA
<213> ORGANISM: Artificial Sequence
<220> FEATURE:
<223> OTHER INFORMATION: PN encoding Chimeric light chain Lc SEQ ID: 10

<400> SEQUENCE: 44

| | |
|---|---:|
| atgaggtgct ctcttcagtt tctggggtg cttatgttct ggatctctgg agtcagtggg | 60 |
| gatattgtga taacccagga tgaactctcc aatcctgtca cttctggaga atcagtttcc | 120 |

```
atctcctgca ggtctagtaa gagtctccta tataaggatg ggaagacata cttgaattgg      180
tttctgcaga gaccaggaca atctcctcag ctcctgatct atttgatgtc cacccgtgca      240
tcaggagtct cagaccggtt tagtggcagt gggtcaggaa cagatttcac cctgaaaatc      300
agtagagtga aggctgagga tgtgggtgtg tattactgtc aacaacttgt agagtatccg      360
ctcacgttcg gtgctgggac caagctgag ctgaaacgta cggtggctgc accatctgtc       420
ttcatcttcc cgccatctga tgagcagttg aaatctggaa ctgcctctgt tgtgtgcctg      480
ctgaataact tctatcccag agaggccaaa gtacagtgga aggtggacaa cgccctccaa      540
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct tcaacagggg agagtgttag      720
```

```
<210> SEQ ID NO 45
<211> LENGTH: 339
<212> TYPE: DNA
<213> ORGANISM: Artificial Sequence
<220> FEATURE:
<223> OTHER INFORMATION: PN encoding 2A10 VH humanised construct H5
      SEQ ID: 11

<400> SEQUENCE: 45
caggtgcagc tggtgcagtc tggggctgag gtgaagaagc ctggggcctc agtgaaggtt       60
tcctgcaagg catctggata caccttcacc agctactgga tgcactgggt gcgacaggcc      120
cctggacaag gcttgagtg gatgggaaat attaatccta gcaatggtgg tactaactac       180
aatgagaagt tcaagagcag agtcaccatg accagggaca cgtccacgag cacagcctac      240
atggagctga gcagcctgag atctgaggac acggccgtgt attactgtga actgggacag      300
ggctactggg gccagggaac actagtcaca gtctcctca                             339
```

```
<210> SEQ ID NO 46
<211> LENGTH: 339
<212> TYPE: DNA
<213> ORGANISM: Artificial Sequence
<220> FEATURE:
<223> OTHER INFORMATION: PN encoding 2A10 VH humanised construct H6
      SEQ ID: 12

<400> SEQUENCE: 46
caggtgcagc tggtgcagtc tggggctgag gtgaagaagc ctggggcctc agtgaaggtt       60
tcctgcaagg catctggata caccttcacc agctactgga tgcactgggt gcgacaggcc      120
cctggacaag gcttgagtg gatcggaaat attaatccta gcaatggtgg tactaactac       180
aatgagaagt tcaagagcag agccaccatg accagggaca cgtccacgag cacagcctac      240
atggagctga gcagcctgag atctgaggac acggccgtgt attactgtga actgggacag      300
ggctactggg gccagggaac actagtcaca gtctcctca                             339
```

```
<210> SEQ ID NO 47
<211> LENGTH: 339
<212> TYPE: DNA
<213> ORGANISM: Artificial Sequence
<220> FEATURE:
<223> OTHER INFORMATION: PN encoding 2A10 VH humanised construct H700
      SEQ ID: 13

<400> SEQUENCE: 47
caggtgcagc tggtgcagtc tggggctgag gtgaagaagc ctggggcctc agtgaaggtt       60
```

```
tcctgcaagg catctggata caccttcacc agctactgga tgcactgggt gcgacaggcc    120
cctggacaag ggcttgagtg gatcggaaat attaatccta gcaatggtgg tactaactac    180
aatgagaagt tcaagagcag agccaccctg accgtagaca atccacgag cacagcctac    240 atggagctga gcagcctgag atctgaggac acggccgtgt attactgtga actgggacag    300
ggctactggg gccagggaac actagtcaca gtctcctca                           339
```

```
<210> SEQ ID NO 48
<211> LENGTH: 339
<212> TYPE: DNA
<213> ORGANISM: Artificial Sequence
<220> FEATURE:
<223> OTHER INFORMATION: PN encoding 2A10 VH humanised construct H14 SEQ
      ID: 14

<400> SEQUENCE: 48
caggtgcagc tggtgcagtc tggggctgag gtggtcaagc ctggggcctc agtgaagctc     60
tcctgcaagg catctggata caccttcacc agctactgga tgcactgggt gaaacaggcc    120
cctggacaag ggcttgagtg gatcggaaat attaatccta gcaatggtgg tactaactac    180
aatgagaagt tcaagagcag agccaccctc accagggaca cgtccacgag cacagcctac    240
atggagctga gcagcctgag atctgaggac acggccgtgt attactgtga actgggacag    300
ggctactggg gccagggaac actagtcaca gtctcctca                           339
```

```
<210> SEQ ID NO 49
<211> LENGTH: 339
<212> TYPE: DNA
<213> ORGANISM: Artificial Sequence
<220> FEATURE:
<223> OTHER INFORMATION: PN encoding 2A10 VH humanised construct H15 SEQ
      ID: 15

<400> SEQUENCE: 49
caggtgcagc tggtgcagtc tggggctgag gtggtcaagc ctggggcctc agtgaagctc     60
tcctgcaagg catctggata caccttcacc agctactgga tgcactgggt gaaacagcga    120
cctggacaag ggcttgagtg gatcggaaat attaatccta gcaatggtgg tactaactac    180
aatgagaagt tcaagagcaa agccaccctc accgtcgaca cgtccagcag cacagcctac    240
atggagctga gcagcctgag atctgaggac agcgccgtgt attactgtga actgggacag    300
ggctactggg gccagggaac actagtcaca gtctcctca                           339
```

```
<210> SEQ ID NO 50
<211> LENGTH: 339
<212> TYPE: DNA
<213> ORGANISM: Artificial Sequence
<220> FEATURE:
<223> OTHER INFORMATION: PN encoding 2A10 VH humanised construct H16 SEQ
      ID: 16

<400> SEQUENCE: 50
caggtgcagc tggtgcagtc tggggctgag gtgaagaagc ctggggcctc agtgaaggtt     60
tcctgcaagg catctggata caccttcacc agctactgga tgcactggGt gaaacagcga    120
cctggacaag ggcttgagtg gatcggaaat attaatccta gcaatggtgg tactaactac    180
aatgagaagt tcaagagcaa agccaccctc accgtcgaca atccacgag cacagcctac    240 atggagctga gcagcctgag atctgaggac acggccgtgt attactgtga actgggacag    300
ggctactggg gccagggaac actagtcaca gtctcctca                           339
```

<210> SEQ ID NO 51
<211> LENGTH: 339
<212> TYPE: DNA
<213> ORGANISM: Artificial Sequence
<220> FEATURE:
<223> OTHER INFORMATION: PN encoding 2A10 VH humanised construct H17 SEQ ID: 17

<400> SEQUENCE: 51

```
caggtgcagc tggtgcagtc tggggctgag gtggtcaagc ctggggcctc agtgaagctc      60
tcctgcaagg catctggata caccttcacc agctactgga tgcactgggt gaaacagcga     120
cctggacaag ggcttgagtg gatcggaaat attaatccta gcaatggtgg tactaactac     180
aatgagaagt tcaagagcaa agccaccctc accgtcgaca atccacgag cacagcctac      240
atggagctga gcagcctgag atctgaggac acggccgtgt attactgtga actgggacag     300
ggctactggg gccagggaac actagtcaca gtctcctca                            339
```

<210> SEQ ID NO 52
<211> LENGTH: 339
<212> TYPE: DNA
<213> ORGANISM: Artificial Sequence
<220> FEATURE:
<223> OTHER INFORMATION: PN encoding 2A10 VH humanised construct H18 SEQ ID: 18

<400> SEQUENCE: 52

```
caggtgcagc tggtgcagtc tggggctgag gtggtcaagc ctggggcctc agtgaagctc      60
tcctgcaagg catctggata caccttcacc agctactgga tgcactgggt gaaacagcga     120
cctggacaag ggcttgagtg gatcggaaat attaatccta gcaatggtgg tactaactac     180
aatgagaagt tcaagagcaa agccaccctc accgtcgaca atccagcag cacagcctac      240
atggagctga gcagcctgag atctgaggac agcgccgtgt attactgtga actgggacag     300
ggctactggg gccagggaac actagtcaca gtctcctca                            339
```

<210> SEQ ID NO 53
<211> LENGTH: 336
<212> TYPE: DNA
<213> ORGANISM: Artificial Sequence
<220> FEATURE:
<223> OTHER INFORMATION: PN encoding 2A10 VL humanised construct L6 SEQ ID: 19

<400> SEQUENCE: 53

```
gatattgtga tgactcagtc tccactctcc ctgcccgtca cccctggaga gccggcctcc      60
atctcctgca ggtctagtaa gagtctccta tataaggatg gaagacata cttgaattgg     120
ttcctgcagc gaccagggca gtctccacag ctcctgatct atttgatgtc cacccgtgca     180
tcaggggtcc ctgacaggtt cagtggcagt ggatcaggca cagattttac actgaaaatc     240
agcagagtgg aggctgagga tgttggggtt tattactgcc aacaacttgt agagtatccg     300
ctcacgttcg gcggagggac caaggtggag atcaaa                               336
```

<210> SEQ ID NO 54
<211> LENGTH: 336
<212> TYPE: DNA
<213> ORGANISM: Artificial Sequence
<220> FEATURE:
<223> OTHER INFORMATION: PN encoding 2A10 VL humanised construct L13 SEQ ID: 20

<400> SEQUENCE: 54

```
gatattgtga tgacccagtc tccactctcc ctgcccgtca cccttggaca gccggcctcc    60
atctcctgca ggtctagtaa gagtctccta tataaggatg gaagacata  cttgaattgg   120
tttcagcaga ggccaggcca atctccacag ctcctaattt atttgatgtc cacccgtgca   180
tctggggtcc cagacagatt cagcggcggt gggtcaggca ctgatttcac actgaaaatc   240
agcagggtgg aggctgagga tgttggggtt tattactgcc aacaacttgt agagtatccg   300
ctcacgtttg gccaggggac caagctggag atcaaa                             336
```

<210> SEQ ID NO 55
<211> LENGTH: 336
<212> TYPE: DNA
<213> ORGANISM: Artificial Sequence
<220> FEATURE:
<223> OTHER INFORMATION: PN encoding 2A10 VL humanised construct L14 SEQ ID: 21

<400> SEQUENCE: 55

```
gatattgtga tgacccagtc tccactctcc ctgcccgtca cccttggaca gccggcctcc    60
atctcctgca ggtctagtaa gagtctccta tataaggatg gaagacata  cttgaattgg   120
tttctccaga ggccaggcca atctccacag ctcctaattt atttgatgtc cacccgtgca   180
tctggggtcc cagacagatt cagcggcggt gggtcaggca ctgatttcac actgaaaatc   240
agcagggtgg aggctgagga tgttggggtt tattactgcc aacaacttgt agagtatccg   300
ctcacgtttg gccaggggac caagctggag atcaaa                             336
```

<210> SEQ ID NO 56
<211> LENGTH: 336
<212> TYPE: DNA
<213> ORGANISM: Artificial Sequence
<220> FEATURE:
<223> OTHER INFORMATION: PN encoding 2A10 VL humanised construct L15 SEQ ID: 22

<400> SEQUENCE: 56

```
gatattgtga tgacccagtc tccactctcc ctgcccgtca cccttggaca gccggcctcc    60
atctcctgca ggtctagtaa gagtctccta tataaggatg gaagacata  cttgaattgg   120
tttctccaga ggccaggcca atctccacag ctcctaattt atttgatgtc cacccgtgca   180
tctggggtca cgacagatt  cagcggcggt gggtcaggca ctgatttcac actgaaaatc   240
agcagggtgg aggctgagga tgttggggtt tattactgcc aacaacttgt agagtatccg   300
ctcacgtttg gccaggggac caagctggag atcaaa                             336
```

<210> SEQ ID NO 57
<211> LENGTH: 336
<212> TYPE: DNA
<213> ORGANISM: Artificial Sequence
<220> FEATURE:
<223> OTHER INFORMATION: PN encoding 2A10 VL humanised construct L16 SEQ ID: 23

<400> SEQUENCE: 57

```
gatattgtga tgacccagtc tccactctcc aaccccgtca cccttggaca gccggtctcc    60
atctcctgca ggtctagtaa gagtctccta tataaggatg gaagacata  cttgaattgg   120
tttctccaga ggccaggcca atctccacag ctcctaattt atttgatgtc cacccgtgca   180
tctggggtcc cagacagatt cagcggcggt gggtcaggca ctgatttcac actgaaaatc   240
```

```
agcagggtgg aggctgagga tgttggggtt tattactgcc aacaacttgt agagtatccg    300
ctcacgtttg gccaggggac caagctggag atcaaa                              336

<210> SEQ ID NO 58
<211> LENGTH: 336
<212> TYPE: DNA
<213> ORGANISM: Artificial Sequence
<220> FEATURE:
<223> OTHER INFORMATION: PN encoding 2A10 VL humanised construct L17 SEQ
      ID: 24

<400> SEQUENCE: 58
gatattgtga tgacccagga cccactctcc ctgcccgtca cccttggaca gccggcctcc     60
atctcctgca ggtctagtaa gagtctccta tataaggatg gaagacata cttgaattgg    120 tttcagcaga ggccaggcca atctccacag ctcctaattt atttgatgtc acccgtgca    180 tctggggtca gcgacagatt cagcggcagc gggtcaggca ctgatttcac actgaaaatc    240
agcagggtgg aggctgagga tgttggggtt tattactgcc aacaacttgt agagtatccg    300
ctcacgtttg gccaggggac caagctggag atcaaa                              336

<210> SEQ ID NO 59
<211> LENGTH: 336
<212> TYPE: DNA
<213> ORGANISM: Artificial Sequence
<220> FEATURE:
<223> OTHER INFORMATION: PN encoding 2A10 VL humanised construct L18 SEQ
      ID: 25

<400> SEQUENCE: 59
gatattgtga tgacccagga cccactctcc aacccgtca cccttggaca gccggtctcc      60
atctcctgca ggtctagtaa gagtctccta tataaggatg gaagacata cttgaattgg    120 tttctccaga ggccaggcca atctccacag ctcctaattt atttgatgtc acccgtgca    180 tctggggtca gcgacagatt cagcggcagc gggtcaggca ctgatttcac actgaaaatc    240
agcagggtgg aggctgagga tgttggggtt tattactgcc aacaacttgt agagtatccg    300
ctcacgtttg gccaggggac caagctggag atcaaa                              336

<210> SEQ ID NO 60
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H5 SEQ ID: 26

<400> SEQUENCE: 60
atgggatgga gctgtatcat cctcttcttg gtagcaacag ctacaggtgt ccactcccag     60
gtgcagctgg tgcagtctgg ggctgaggtg aagaagcctg ggcctcagt gaaggtttcc    120 tgcaaggcat ctggatacac cttcaccagc tactggatgc actgggtgcg acaggcccct    180
ggacaagggc ttgagtggat gggaaatatt aatcctagca atggtggtac taactacaat    240
gagaagttca agagcagagt caccatgacc agggacacgt ccacgagcac agcctacatg    300
gagctgagca gcctgagatc tgaggacacg gccgtgtatt actgtgaact gggacagggc    360
tactggggcc aggaacactct agtcacagtc tcctcagcct ccaccaaggg cccatcggtc    420
ttccccctgg cacccctcc caagagcacc tctgggggca cagcggccct gggctgcctg    480
gtcaaggact acttccccga accggtgacg gtgtcgtgga actcaggcgc cctgaccagc    540
```

```
ggcgtgcaca ccttcccggc tgtcctacag tcctcaggac tctactccct cagcagcgtg      600
gtgaccgtgc cctccagcag cttgggcacc cagacctaca tctgcaacgt gaatcacaag      660
cccagcaaca ccaaggtgga caagaaagtt gagcccaaat cttgtgacaa aactcacaca      720
tgcccaccgt gcccagcacc tgaactcgcg ggcaccgt cagtcttcct cttcccccca      780
aaacccaagg acaccctcat gatctcccgg acccctgagg tcacatgcgt ggtggtggac      840
gtgagccacg aagaccctga ggtcaagttc aactggtacg tggacggcgt ggaggtgcat      900
aatgccaaga caaagccgcg ggaggagcag tacaacagca cgtaccgtgt ggtcagcgtc      960
ctcaccgtcc tgcaccagga ctggctgaat ggcaaggagt acaagtgcaa ggtctccaac     1020 aaagcccctcc cagcccccat cgagaaaacc atctccaaag ccaaagggca gccccgagaa     1080
ccacaggtgt acaccctgcc cccatcccgg gatgagctga ccaagaacca ggtcagcctg     1140
acctgcctgg tcaaaggctt ctatcccagc gacatcgccg tggagtggga gagcaatggg     1200
cagccggaga caactacaa gaccacgcct cccgtgctgg actccgacgg ctccttcttc     1260
ctctacagca agctcaccgt ggacaagagc aggtggcagc aggggaacgt cttctcatgc     1320
tccgtgatgc atgaggctct gcacaaccac tacacgcaga gagcctctc cctgtctccg     1380 ggtaaatga                                                              1389

<210> SEQ ID NO 61
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H6 SEQ ID: 27

<400> SEQUENCE: 61
atgggatgga gctgtatcat cctcttcttg gtagcaacag ctacaggtgt ccactcccag      60
gtgcagctgg tgcagtctgg ggctgaggtg aagaagcctg gggcctcagt gaaggtttcc     120
tgcaaggcat ctggatacac cttcaccagc tactggatgc actgggtgcg acaggcccct     180
ggacaagggc ttgagtggat cggaaatatt aatcctagca atggtggtac taactacaat     240
gagaagttca gagcagagc accatgacc agggacacgt ccacgagcac agcctacatg     300
gagctgagca gcctgagatc tgaggacacg gccgtgtatt actgtgaact gggacagggc     360 tactgggggcc agggaacact agtcacagtc tcctcagcct ccaccaaggg cccatcggtc     420
ttccccctgg cacctcctc caagagcacc tctgggggca gcggccct gggctgcctg     480 gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
gtgaccgtgc cctccagcag cttgggcacc cagacctaca tctgcaacgt gaatcacaag     660
cccagcaaca ccaaggtgga caagaaagtt gagcccaaat cttgtgacaa aactcacaca     720
tgcccaccgt gcccagcacc tgaactcgcg ggcaccgt cagtcttcct cttcccccca     780
aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacaacagca cgtaccgtgt ggtcagcgtc     960
ctcaccgtcc tgcaccagga ctggctgaat ggcaaggagt acaagtgcaa ggtctccaac    1020 aaagcccctcc cagcccccat cgagaaaacc atctccaaag ccaaagggca gccccgagaa    1080
ccacaggtgt acaccctgcc cccatcccgg gatgagctga ccaagaacca ggtcagcctg    1140
```

-continued

| | |
|---|---|
| acctgcctgg tcaaaggctt ctatcccagc gacatcgccg tggagtggga gagcaatggg | 1200 |
| cagccggaga acaactacaa gaccacgcct cccgtgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 62
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H700 SEQ ID: 28

<400> SEQUENCE: 62

| | |
|---|---|
| atgggatgga gctgtatcat cctcttcttg gtagcaacag ctacaggtgt ccactcccag | 60 |
| gtgcagctgg tgcagtctgg ggctgaggtg aagaagcctg ggcctcagt gaaggtttcc | 120 |
| tgcaaggcat ctggatacac cttcaccagc tactggatgc actgggtgcg acaggcccct | 180 |
| ggacaagggc ttgagtggat cggaaatatt aatcctagca tggtggtac taactacaat | 240 |
| gagaagttca gagcagagc caccctgacc gtagacaaat ccacgagcac agcctacatg | 300 |
| gagctgagca gcctgagatc tgaggacacg gccgtgtatt actgtgaact gggacagggc | 360 |
| tactggggcc agggaacact agtcacagtc tcctcagcct ccaccaaggg cccatcggtc | 420 |
| ttccccctgg caccctcctc caagagcacc tctggggca gcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg ggggcaccgt cagtcttcct cttcccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |
| aatgccaaga caaagccgcg ggaggagcag tacaacagca cgtaccgtgt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaagggca gccccgagaa | 1080 |
| ccacaggtgt acaccctgcc cccatcccgg gatgagctga ccaagaacca ggtcagcctg | 1140 |
| acctgcctgg tcaaaggctt ctatcccagc gacatcgccg tggagtggga gagcaatggg | 1200 |
| cagccggaga acaactacaa gaccacgcct cccgtgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 63
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H14 SEQ ID: 29

<400> SEQUENCE: 63

```
atgggatgga gctgtatcat cctcttcttg gtagcaacag ctacaggtgt ccactcccag      60
gtgcagctgg tgcagtctgg ggctgaggtg gtcaagcctg gggcctcagt gaagctctcc     120
tgcaaggcat ctggatacac cttcaccagc tactggatgc actgggtgaa acaggcccct     180
ggacaagggc ttgagtggat cggaaatatt aatcctagca atggtggtac taactacaat     240
gagaagttca agagcagagc caccctcacc agggacacgt ccacgagcac agcctacatg     300
gagctgagca gcctgagatc tgaggacacg gccgtgtatt actgtgaact gggacagggc     360
tactggggcc aggaaacact agtcacagtc tcctcagcct ccaccaaggg cccatcggtc     420
ttccccctgg cacctcctc aagagcacc tctggggca cagcggccct gggctgcctg     480
gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
gtgaccgtgc cctccagcag cttgggcacc cagacctaca tctgcaacgt gaatcacaag     660
cccagcaaca ccaaggtgga caagaaagtt gagcccaaat cttgtgacaa aactcacaca     720
tgcccaccgt gcccagcacc tgaactcgcg gggcaccgt cagtcttcct cttccccca     780 aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacaacagca cgtaccgtgt ggtcagcgtc     960
ctcaccgtcc tgcaccagga ctggctgaat ggcaaggagt acaagtgcaa ggtctccaac    1020
aaagccctcc cagcccccat cgagaaaacc atctccaag ccaagggca gccccgagaa    1080 ccacaggtgt acaccctgcc cccatcccgg gatgagctga ccaagaacca ggtcagcctg    1140 acctgcctg tcaaaggctt ctatccagc gacatcgccg tggagtggga gagcaatggg    1200
cagccggaga caactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                            1389
```

<210> SEQ ID NO 64
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H15 SEQ ID: 30

<400> SEQUENCE: 64

```
atgggatgga gctgtatcat cctcttcttg gtagcaacag ctacaggtgt ccactcccag      60
gtgcagctgg tgcagtctgg ggctgaggtg gtcaagcctg gggcctcagt gaagctctcc     120
tgcaaggcat ctggatacac cttcaccagc tactggatgc actgggtgaa acaggcgacct    180 ggacaagggc ttgagtggat cggaaatatt aatcctagca atggtggtac taactacaat     240
gagaagttca agagcaaagc caccctcacc gtcgacacgt ccagcagcac agcctacatg     300
gagctgagca gcctgagatc tgaggacagc gccgtgtatt actgtgaact gggacagggc     360
tactggggcc aggaaacact agtcacagtc tcctcagcct ccaccaaggg cccatcggtc     420
ttccccctgg cacctcctc aagagcacc tctggggca cagcggccct gggctgcctg     480
gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
```

```
gtgaccgtgc cctccagcag cttgggcacc cagacctaca tctgcaacgt gaatcacaag      660
cccagcaaca ccaaggtgga caagaaagtt gagcccaaat cttgtgacaa aactcacaca      720
tgcccaccgt gcccagcacc tgaactcgcg gggcaccgt cagtcttcct cttccccca       780 aaacccaagg acaccctcat gatctcccgg acccctgagg tcacatgcgt ggtggtggac      840
gtgagccacg aagaccctga ggtcaagttc aactggtacg tggacggcgt ggaggtgcat      900
aatgccaaga caaagccgcg ggaggagcag tacaacagca cgtaccgtgt ggtcagcgtc      960
ctcaccgtcc tgcaccagga ctggctgaat ggcaaggagt acaagtgcaa ggtctccaac     1020
aaagccctcc cagcccccat cgagaaaacc atctccaaag ccaaagggca gccccgagaa     1080
ccacaggtgt acaccctgcc cccatcccgg gatgagctga ccaagaacca ggtcagcctg     1140
acctgcctgg tcaaaggctt ctatcccagc gacatcgccg tggagtggga gagcaatggg     1200
cagccggaga caactacaa gaccacgcct cccgtgctgg actccgacgg ctccttcttc      1260
ctctacagca agctcaccgt ggacaagagc aggtggcagc aggggaacgt cttctcatgc     1320
tccgtgatgc atgaggctct gcacaaccac tacacgcaga gagcctctc cctgtctccg      1380 ggtaaatga                                                             1389
```

<210> SEQ ID NO 65
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H16 SEQ ID: 31

<400> SEQUENCE: 65

```
atgggatgga gctgtatcat cctcttcttg gtagcaacag ctacaggtgt ccactcccag       60
gtgcagctgg tgcagtctgg ggctgaggtg aagaagcctg gggcctcagt gaaggttcc       120 tgcaaggcat ctggatacac cttcaccagc tactggatgc actgggtgaa acagcgacct      180
ggacaagggc ttgagtggat cggaaatatt aatcctagca atggtggtac taactacaat      240
gagaagttca gagcaaagc caccctcacc gtcgacaaat ccacgagcac agcctacatg       300
gagctgagca gcctgagatc tgaggacacg gccgtgtatt actgtgaact gggacagggc      360
tactggggcc agggaacact agtcacagtc tcctcagcct ccaccaaggg cccatcggtc      420
ttccccctgg caccctcctc caagagcacc tctgggggca cagcggccct gggctgcctg      480
gtcaaggact acttccccga accggtgacg gtgtcgtgga actcaggcgc cctgaccagc      540
ggcgtgcaca ccttcccggc tgtcctacag tcctcaggac tctactccct cagcagcgtg      600
gtgaccgtgc cctccagcag cttgggcacc cagacctaca tctgcaacgt gaatcacaag      660
cccagcaaca ccaaggtgga caagaaagtt gagcccaaat cttgtgacaa aactcacaca      720
tgcccaccgt gcccagcacc tgaactcgcg gggcaccgt cagtcttcct cttccccca       780 aaacccaagg acaccctcat gatctcccgg acccctgagg tcacatgcgt ggtggtggac      840
gtgagccacg aagaccctga ggtcaagttc aactggtacg tggacggcgt ggaggtgcat      900
aatgccaaga caaagccgcg ggaggagcag tacaacagca cgtaccgtgt ggtcagcgtc      960
ctcaccgtcc tgcaccagga ctggctgaat ggcaaggagt acaagtgcaa ggtctccaac     1020
aaagccctcc cagcccccat cgagaaaacc atctccaaag ccaaagggca gccccgagaa     1080
ccacaggtgt acaccctgcc cccatcccgg gatgagctga ccaagaacca ggtcagcctg     1140
acctgcctgg tcaaaggctt ctatcccagc gacatcgccg tggagtggga gagcaatggg     1200
```

```
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                            1389

<210> SEQ ID NO 66
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H17 SEQ ID: 32

<400> SEQUENCE: 66
atgggatgga gctgtatcat cctcttcttg gtagcaacag ctacaggtgt ccactcccag      60
gtgcagctgg tgcagtctgg ggctgaggtg gtcaagcctg ggcctcagt gaagctctcc     120 tgcaaggcat ctggatacac cttcaccagc tactggatgc actgggtgaa acagcgacct    180
ggacaagggc ttgagtggat cggaaatatt aatcctagca atggtggtac taactacaat    240
gagaagttca agagcaaagc caccctcacc gtcgacaaat ccacgagcac agcctacatg    300
gagctgagca gcctgagatc tgaggacacg gccgtgtatt actgtgaact gggacagggc    360
tactggggcc agggaacact agtcacagtc tcctcagcct ccaccaaggg cccatcggtc    420
ttccccctgg cacctcctc caagagcacc tctggggca gcggccct gggctgcctg       480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg gggcaccgt cagtcttcct cttccccca     780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                            1389

<210> SEQ ID NO 67
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H18 SEQ ID: 33

<400> SEQUENCE: 67
```

```
atgggatgga gctgtatcat cctcttcttg gtagcaacag ctacaggtgt ccactcccag    60
gtgcagctgg tgcagtctgg ggctgaggtg gtcaagcctg gggcctcagt gaagctctcc   120
tgcaaggcat ctggatacac cttcaccagc tactggatgc actgggtgaa acagcgacct   180
ggacaagggc ttgagtggat cggaaatatt aatcctagca atggtggtac taactacaat   240
gagaagttca gagcaaagc caccctcacc gtcgacaaat ccagcagcac agcctacatg   300
```

```
atgggatgga gctgtatcat cctcttcttg gtagcaacag ctacaggtgt ccactcccag    60
gtgcagctgg tgcagtctgg ggctgaggtg gtcaagcctg gggcctcagt gaagctctcc   120
tgcaaggcat ctggatacac cttcaccagc tactggatgc actgggtgaa acagcgacct   180
ggacaagggc ttgagtggat cggaaatatt aatcctagca atggtggtac taactacaat   240
gagaagttca gagcaaagc caccctcacc gtcgacaaat ccagcagcac agcctacatg   300
gagctgagca gcctgagatc tgaggacagc gccgtgtatt actgtgaact gggacagggc   360
tactggggcc agggaacact agtcacagtc tcctcagcct ccaccaaggg cccatcggtc   420
ttccccctgg caccctcctc caagagcacc tctgggggca gcggccct gggctgcctg   480
gtcaaggact acttccccga accggtgacg gtgtcgtgga actcaggcgc cctgaccagc   540
ggcgtgcaca ccttcccggc tgtcctacag tcctcaggac tctactccct cagcagcgtg   600
gtgaccgtgc cctccagcag cttgggcacc cagacctaca tctgcaacgt gaatcacaag   660
cccagcaaca ccaaggtgga caagaaagtt gagcccaaat cttgtgacaa aactcacaca   720
tgcccaccgt gcccagcacc tgaactcgcg ggggcaccgt cagtcttcct cttccccca    780
aaacccaagg acaccctcat gatctcccgg acccctgagg tcacatgcgt ggtggtggac   840
gtgagccacg aagaccctga ggtcaagttc aactggtacg tggacggcgt ggaggtgcat   900
aatgccaaga caaagccgcg ggaggagcag tacaacagca cgtaccgtgt ggtcagcgtc   960
ctcaccgtcc tgcaccagga ctggctgaat ggcaaggagt acaagtgcaa ggtctccaac  1020
aaagccctcc cagcccccat cgagaaaacc atctccaaag ccaagggca gccccgagaa  1080
ccacaggtgt acaccctgcc cccatcccgg gatgagctga ccaagaacca ggtcagcctg  1140
acctgcctgg tcaaaggctt ctatcccagc gacatcgccg tggagtggga gagcaatggg  1200
cagccggaga acaactacaa gaccacgcct cccgtgctgg actccgacgg ctccttcttc  1260
ctctacagca agctcaccgt ggacaagagc aggtggcagc aggggaacgt cttctcatgc  1320
tccgtgatgc atgaggctct gcacaaccac tacacgcaga agagcctctc cctgtctccg  1380
ggtaaatga                                                          1389
```

<210> SEQ ID NO 68
<211> LENGTH: 717
<212> TYPE: DNA
<213> ORGANISM: Artificial Sequence
<220> FEATURE:
<223> OTHER INFORMATION: PN encoding 2A10 light chain humanised
      construct L6 SEQ ID: 34

<400> SEQUENCE: 68

```
atgggatgga gctgtatcat cctcttcttg gtagcaacag ctacaggtgt ccactccgat    60
attgtgatga ctcagtctcc actctccctg cccgtcaccc ctggagagcc ggcctccatc   120
tcctgcaggt ctagtaagag tctcctatat aaggatggga agacatactt gaattggttc   180
ctgcagcgac cagggcagtc tccacagctc ctgatctatt tgatgtccac ccgtgcatca   240
ggggtccctg acaggttcag tggcagtgga tcaggcacag attttacact gaaaatcagc   300
agagtggagg ctgaggatgt tggggtttat tactgccaac aacttgtaga gtatccgctc   360
acgttcggcg agggaccaa ggtggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
```

-continued

```
agcaccctga cgctgagcaa agcagactac gagaaacaca aagtctacgc ctgcgaagtc    660
acccatcagg gcctgagctc gcccgtcaca aagagcttca acaggggaga gtgttag      717
```

<210> SEQ ID NO 69
<211> LENGTH: 717
<212> TYPE: DNA
<213> ORGANISM: Artificial Sequence
<220> FEATURE:
<223> OTHER INFORMATION: PN encoding 2A10 light chain humanised
      construct L13 SEQ ID: 35

<400> SEQUENCE: 69

```
atgggatgga gctgtatcat cctcttcttg gtagcaacag ctacaggtgt ccactccgat    60
attgtgatga cccagtctcc actctccctg cccgtcaccc ttggacagcc ggcctccatc   120
tcctgcaggt ctagtaagag tctcctatat aaggatggga agacatactt gaattggttt   180
cagcagaggc caggccaatc tccacagctc ctaatttatt tgatgtccac ccgtgcatct   240
ggggtcccag acagattcag cggcggtggg tcaggcactg atttcacact gaaaatcagc   300
agggtggagg ctgaggatgt tggggtttat tactgccaac aacttgtaga gtatccgctc   360
acgtttggcc aggggaccaa gctggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
agcaccctga cgctgagcaa agcagactac gagaaacaca aagtctacgc ctgcgaagtc   660
acccatcagg gcctgagctc gcccgtcaca aagagcttca acaggggaga gtgttag      717
```

<210> SEQ ID NO 70
<211> LENGTH: 717
<212> TYPE: DNA
<213> ORGANISM: Artificial Sequence
<220> FEATURE:
<223> OTHER INFORMATION: PN encoding 2A10 light chain humanised
      construct L14 SEQ ID: 36

<400> SEQUENCE: 70

```
atgggatgga gctgtatcat cctcttcttg gtagcaacag ctacaggtgt ccactccgat    60
attgtgatga cccagtctcc actctccctg cccgtcaccc ttggacagcc ggcctccatc   120
tcctgcaggt ctagtaagag tctcctatat aaggatggga agacatactt gaattggttt   180
ctccagaggc caggccaatc tccacagctc ctaatttatt tgatgtccac ccgtgcatct   240
ggggtcccag acagattcag cggcggtggg tcaggcactg atttcacact gaaaatcagc   300
agggtggagg ctgaggatgt tggggtttat tactgccaac aacttgtaga gtatccgctc   360
acgtttggcc aggggaccaa gctggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
agcaccctga cgctgagcaa agcagactac gagaaacaca aagtctacgc ctgcgaagtc   660
acccatcagg gcctgagctc gcccgtcaca aagagcttca acaggggaga gtgttag      717
```

<210> SEQ ID NO 71
<211> LENGTH: 717
<212> TYPE: DNA
<213> ORGANISM: Artificial Sequence

```
<220> FEATURE:
<223> OTHER INFORMATION: PN encoding 2A10 light chain humanised
      construct L15 SEQ ID: 37

<400> SEQUENCE: 71
atgggatgga gctgtatcat cctcttcttg gtagcaacag ctacaggtgt ccactccgat    60
attgtgatga cccagtctcc actctccctg cccgtcaccc ttggacagcc ggcctccatc   120
tcctgcaggt ctagtaagag tctcctatat aaggatggga agacatactt gaattggttt   180
ctccagaggc caggccaatc tccacagctc ctaatttatt tgatgtccac ccgtgcatct   240
ggggtcagcg acagattcag cggcggtggg tcaggcactg atttcacact gaaaatcagc   300
agggtggagg ctgaggatgt tggggtttat tactgccaac aacttgtaga gtatccgctc   360
acgtttggcc aggggaccaa gctggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
agcaccctga cgctgagcaa agcagactac gagaaacaca aagtctacgc ctgcgaagtc   660
acccatcagg gcctgagctc gcccgtcaca aagagcttca acaggggaga gtgttag     717

<210> SEQ ID NO 72
<211> LENGTH: 717
<212> TYPE: DNA
<213> ORGANISM: Artificial Sequence
<220> FEATURE:
<223> OTHER INFORMATION: PN encoding 2A10 light chain humanised
      construct L16 SEQ ID: 38

<400> SEQUENCE: 72
atgggatgga gctgtatcat cctcttcttg gtagcaacag ctacaggtgt ccactccgat    60
attgtgatga cccagtctcc actctccaac cccgtcaccc ttggacagcc ggtctccatc   120
tcctgcaggt ctagtaagag tctcctatat aaggatggga agacatactt gaattggttt   180
ctccagaggc caggccaatc tccacagctc ctaatttatt tgatgtccac ccgtgcatct   240
ggggtcccag acagattcag cggcggtggg tcaggcactg atttcacact gaaaatcagc   300
agggtggagg ctgaggatgt tggggtttat tactgccaac aacttgtaga gtatccgctc   360
acgtttggcc aggggaccaa gctggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc    660 acccatcagg gcctgagctc gcccgtcaca aagagcttca acaggggaga gtgttag     717

<210> SEQ ID NO 73
<211> LENGTH: 717
<212> TYPE: DNA
<213> ORGANISM: Artificial Sequence
<220> FEATURE:
<223> OTHER INFORMATION: PN encoding 2A10 light chain humanised
      construct L17 SEQ ID: 39

<400> SEQUENCE: 73
atgggatgga gctgtatcat cctcttcttg gtagcaacag ctacaggtgt ccactccgat    60
attgtgatga cccaggaccc actctccctg cccgtcaccc ttggacagcc ggcctccatc   120
```

```
tcctgcaggt ctagtaagag tctcctatat aaggatggga agacatactt gaattggttt      180
cagcagaggc caggccaatc tccacagctc ctaatttatt tgatgtccac ccgtgcatct      240
ggggtcagcg acagattcag cggcagcggg tcaggcactg atttcacact gaaaatcagc      300
agggtggagg ctgaggatgt tggggtttat tactgccaac aacttgtaga gtatccgctc      360
acgtttggcc aggggaccaa gctggagatc aaacgtacgg tggctgcacc atctgtcttc      420
atcttcccgc catctgatga gcagttgaaa tctggaactg cctctgttgt gtgcctgctg      480
aataacttct atcccagaga ggccaaagta cagtggaagg tggacaacgc cctccaatcg      540
ggtaactccc aggagagtgt cacagagcag gacagcaagg acagcaccta cagcctcagc      600
agcaccctga cgctgagcaa agcagactac gagaaacaca agtctacgc ctgcgaagtc      660 acccatcagg gcctgagctc gcccgtcaca aagagcttca caggggagag tgttag         717
```

<210> SEQ ID NO 74
<211> LENGTH: 717
<212> TYPE: DNA
<213> ORGANISM: Artificial Sequence
<220> FEATURE:
<223> OTHER INFORMATION: PN encoding 2A10 light chain humanised
      construct L18 SEQ ID: 40

<400> SEQUENCE: 74

```
atgggatgga gctgtatcat cctcttcttg gtagcaacag ctacaggtgt ccactccgat       60
attgtgatga cccaggaccc actctccaac cccgtcaccc ttggacagcc ggtctccatc      120
tcctgcaggt ctagtaagag tctcctatat aaggatggga agacatactt gaattggttt      180
ctccagaggc caggccaatc tccacagctc ctaatttatt tgatgtccac ccgtgcatct      240
ggggtcagcg acagattcag cggcagcggg tcaggcactg atttcacact gaaaatcagc      300
agggtggagg ctgaggatgt tggggtttat tactgccaac aacttgtaga gtatccgctc      360
acgtttggcc aggggaccaa gctggagatc aaacgtacgg tggctgcacc atctgtcttc      420
atcttcccgc catctgatga gcagttgaaa tctggaactg cctctgttgt gtgcctgctg      480
aataacttct atcccagaga ggccaaagta cagtggaagg tggacaacgc cctccaatcg      540
ggtaactccc aggagagtgt cacagagcag gacagcaagg acagcaccta cagcctcagc      600
agcaccctga cgctgagcaa agcagactac gagaaacaca agtctacgc ctgcgaagtc      660 acccatcagg gcctgagctc gcccgtcaca aagagcttca caggggagag tgttag         717
```

<210> SEQ ID NO 75
<211> LENGTH: 19
<212> TYPE: PRT
<213> ORGANISM: Artificial Sequence
<220> FEATURE:
<223> OTHER INFORMATION: Campath leader sequence

<400> SEQUENCE: 75

Met Gly Trp Ser Cys Ile Ile Leu Phe Leu Val Ala Thr Ala Thr Gly
1               5                   10                  15

Val His Ser

<210> SEQ ID NO 76
<211> LENGTH: 201
<212> TYPE: PRT
<213> ORGANISM: Artificial Sequence
<220> FEATURE:
<223> OTHER INFORMATION: Amino acids 586-785 of human NOGO A (NOGO-A56)

<400> SEQUENCE: 76

Met Gln Glu Ser Leu Tyr Pro Ala Ala Gln Leu Cys Pro Ser Phe Glu
1               5                   10                  15

Glu Ser Glu Ala Thr Pro Ser Pro Val Leu Pro Asp Ile Val Met Glu
            20                  25                  30

Ala Pro Leu Asn Ser Ala Val Pro Ser Ala Gly Ala Ser Val Ile Gln
        35                  40                  45

Pro Ser Ser Pro Leu Glu Ala Ser Val Asn Tyr Glu Ser Ile
    50                  55                  60

Lys His Glu Pro Glu Asn Pro Pro Tyr Glu Glu Ala Met Ser Val
65                  70                  75                  80

Ser Leu Lys Lys Val Ser Gly Ile Lys Glu Glu Ile Lys Glu Pro Glu
                85                  90                  95

Asn Ile Asn Ala Ala Leu Gln Glu Thr Glu Ala Pro Tyr Ile Ser Ile
                100                 105                 110

Ala Cys Asp Leu Ile Lys Glu Thr Lys Leu Ser Ala Glu Pro Ala Pro
                115                 120                 125

Asp Phe Ser Asp Tyr Ser Glu Met Ala Lys Val Glu Gln Pro Val Pro
130                 135                 140

Asp His Ser Glu Leu Val Glu Asp Ser Ser Pro Asp Ser Glu Pro Val
145                 150                 155                 160

Asp Leu Phe Ser Asp Asp Ser Ile Pro Asp Val Pro Gln Lys Gln Asp
                165                 170                 175

Glu Thr Val Met Leu Val Lys Ser Leu Thr Glu Thr Ser Phe Glu
                180                 185                 190

Ser Met Ile Glu Tyr Glu Asn Lys Glu
            195                 200

<210> SEQ ID NO 77
<211> LENGTH: 113
<212> TYPE: PRT
<213> ORGANISM: Artificial Sequence
<220> FEATURE:
<223> OTHER INFORMATION: 2A10 VH humanised construct H1

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Asn Pro Ser Asn Gly Gly Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
                100                 105                 110

Ser

<210> SEQ ID NO 78
<211> LENGTH: 112
<212> TYPE: PRT
<213> ORGANISM: Artificial Sequence
<220> FEATURE:
<223> OTHER INFORMATION: 2A10 VL humanised construct L11

<400> SEQUENCE: 78

```
Asp Ile Val Ile Thr Gln Ser Pro Leu Ser Leu Pro Val Thr Leu Gly
 1               5                  10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Gln Gln Arg Pro Gly Gln Ser
        35                  40                  45

Pro Gln Leu Leu Ile Tyr Leu Met Ser Thr Arg Ala Ser Gly Val Pro
    50                  55                  60

Asp Arg Phe Ser Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110
```

<210> SEQ ID NO 79
<211> LENGTH: 462
<212> TYPE: PRT
<213> ORGANISM: Artificial Sequence
<220> FEATURE:
<223> OTHER INFORMATION: 2A10 heavy chain humanised construct H1

<400> SEQUENCE: 79

```
Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Met Gly Asn Ile Asn Pro Ser Asn Gly Gly Thr Asn Tyr Asn
65                  70                  75                  80

Glu Lys Phe Lys Ser Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
            115                 120                 125

Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
```

```
                225                 230                 235                 240
Cys Pro Pro Cys Pro Ala Pro Glu Leu Ala Gly Ala Pro Ser Val Phe
                245                 250                 255
Leu Phe Pro Pro Lys Pro Lys Asp Thr Leu Met Ile Ser Arg Thr Pro
                260                 265                 270
Glu Val Thr Cys Val Val Val Asp Val Ser His Glu Asp Pro Glu Val
                275                 280                 285
Lys Phe Asn Trp Tyr Val Asp Gly Val Glu Val His Asn Ala Lys Thr
                290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
                340                 345                 350
Lys Ala Lys Gly Gln Pro Arg Glu Pro Gln Val Tyr Thr Leu Pro Pro
                355                 360                 365
Ser Arg Asp Glu Leu Thr Lys Asn Gln Val Ser Leu Thr Cys Leu Val
                370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
                420                 425                 430
Gln Gln Gly Asn Val Phe Ser Cys Ser Val Met His Glu Ala Leu His
                435                 440                 445
Asn His Tyr Thr Gln Lys Ser Leu Ser Leu Ser Pro Gly Lys
                450                 455                 460

<210> SEQ ID NO 80
<211> LENGTH: 238
<212> TYPE: PRT
<213> ORGANISM: Artificial Sequence
<220> FEATURE:
<223> OTHER INFORMATION: 2A10 light chain humanised construct L11

<400> SEQUENCE: 80

Met Gly Trp Ser Cys Ile Ile Leu Phe Leu Val Ala Thr Ala Thr Gly
1               5                   10                  15
Val His Ser Asp Ile Val Ile Thr Gln Ser Pro Leu Ser Leu Pro Val
                20                  25                  30
Thr Leu Gly Gln Pro Ala Ser Ile Ser Cys Arg Ser Ser Lys Ser Leu
                35                  40                  45
Leu Tyr Lys Asp Gly Lys Thr Tyr Leu Asn Trp Phe Gln Gln Arg Pro
            50                  55                  60
Gly Gln Ser Pro Gln Leu Leu Ile Tyr Leu Met Ser Thr Arg Ala Ser
65                  70                  75                  80
Gly Val Pro Asp Arg Phe Ser Gly Gly Ser Gly Thr Asp Phe Thr
                85                  90                  95
Leu Lys Ile Ser Arg Val Glu Ala Glu Asp Val Gly Val Tyr Tyr Cys
                100                 105                 110
Gln Gln Leu Val Glu Tyr Pro Leu Thr Phe Gly Gln Gly Thr Lys Leu
                115                 120                 125
Glu Ile Lys Arg Thr Val Ala Ala Pro Ser Val Phe Ile Phe Pro Pro
```

-continued

```
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 81
<211> LENGTH: 339
<212> TYPE: PRT
<213> ORGANISM: Artificial Sequence
<220> FEATURE:
<223> OTHER INFORMATION: PN encoding 2A10 VH humanised construct H1 SEQ
      ID: 77

<400> SEQUENCE: 81

Cys Ala Gly Gly Thr Gly Cys Ala Gly Cys Thr Gly Gly Thr Gly Cys
 1               5                  10                  15

Ala Gly Thr Cys Thr Gly Gly Gly Gly Cys Thr Gly Ala Gly Gly Thr
            20                  25                  30

Gly Ala Ala Gly Ala Ala Gly Cys Cys Thr Gly Gly Gly Gly Cys Cys
        35                  40                  45

Thr Cys Ala Gly Thr Gly Ala Ala Gly Gly Thr Thr Thr Cys Cys Thr
    50                  55                  60

Gly Cys Ala Ala Gly Gly Cys Ala Thr Cys Thr Gly Gly Ala Thr Ala
65                  70                  75                  80

Cys Ala Cys Cys Thr Thr Cys Ala Cys Cys Ala Gly Cys Thr Ala Cys
                85                  90                  95

Thr Gly Gly Ala Thr Gly Cys Ala Cys Thr Gly Gly Gly Thr Gly Cys
            100                 105                 110

Gly Ala Cys Ala Gly Gly Cys Cys Cys Cys Thr Gly Gly Ala Cys Ala
        115                 120                 125

Ala Gly Gly Gly Cys Thr Thr Gly Ala Gly Thr Gly Gly Ala Thr Gly
    130                 135                 140

Gly Gly Ala Ala Ala Thr Ala Thr Thr Ala Ala Thr Cys Cys Thr Ala
145                 150                 155                 160

Gly Cys Ala Ala Thr Gly Gly Thr Gly Gly Thr Ala Cys Thr Ala Ala
                165                 170                 175

Cys Thr Ala Cys Ala Ala Thr Gly Ala Gly Ala Ala Gly Thr Thr Cys
            180                 185                 190

Ala Ala Gly Ala Gly Cys Ala Gly Ala Gly Thr Cys Ala Cys Cys Ala
        195                 200                 205

Thr Gly Ala Cys Cys Ala Gly Gly Gly Ala Cys Ala Cys Gly Thr Cys
    210                 215                 220

Cys Ala Cys Gly Ala Gly Cys Ala Cys Ala Gly Thr Cys Thr Ala Cys
225                 230                 235                 240

Ala Thr Gly Gly Ala Gly Cys Thr Gly Ala Gly Cys Ala Gly Cys Cys
                245                 250                 255
```

```
Thr Gly Ala Gly Ala Thr Cys Thr Gly Ala Gly Gly Ala Cys Ala Cys
            260                 265                 270

Gly Gly Cys Cys Gly Thr Gly Thr Thr Ala Thr Ala Cys Thr Gly Thr
        275                 280                 285

Gly Ala Ala Cys Thr Gly Gly Ala Cys Ala Gly Gly Gly Cys Thr
        290                 295                 300

Ala Cys Thr Gly Gly Gly Cys Cys Ala Gly Gly Ala Ala Cys
305                 310                 315                 320

Ala Cys Thr Ala Gly Thr Cys Ala Cys Ala Gly Thr Cys Thr Cys Cys
                325                 330                 335

Thr Cys Ala

<210> SEQ ID NO 82
<211> LENGTH: 336
<212> TYPE: DNA
<213> ORGANISM: Artificial Sequence
<220> FEATURE:
<223> OTHER INFORMATION: PN encoding 2A10 VL humanised construct L11 SEQ
      ID: 78

<400> SEQUENCE: 82
gatattgtga taacccagtc tccactctcc ctgcccgtca cccttggaca gccggcctcc      60
atctcctgca ggtctagtaa gagtctccta tataaggatg gaagacata cttgaattgg     120 tttcagcaga ggccaggcca atctccacag ctcctaattt atttgatgtc cacccgtgca    180
tctggggtcc cagacagatt cagcggcggt gggtcaggca ctgatttcac actgaaaatc    240
agcagggtgg aggctgagga tgttggggtt tattactgcc aacaacttgt agagtatccg    300
ctcacgtttg gccaggggac caagctggag atcaaa                              336

<210> SEQ ID NO 83
<211> LENGTH: 1389
<212> TYPE: DNA
<213> ORGANISM: Artificial Sequence
<220> FEATURE:
<223> OTHER INFORMATION: PN encoding 2A10 humanised heavy chain H1 SEQ
      ID: 79

<400> SEQUENCE: 83
atgggatgga gctgtatcat cctcttcttg gtagcaacag ctacaggtgt ccactcccag     60
gtgcagctgg tgcagtctgg ggctgaggtg aagaagcctg ggcctcagt gaaggtttcc    120 tgcaaggcat ctggatacac cttcaccagc tactggatgc actgggtgcg acaggccct    180 ggacaaggc ttgagtggat gggaaatatt aatcctagca atggtggtac taactacaat    240
gagaagttca agagcagagt caccatgacc agggacacgt ccacgagcac agtctacatg    300
gagctgagca gcctgagatc tgaggacacg gccgtgtatt actgtgaact gggacagggc    360 tactgggcc agggaacact agtcacagtc tcctcagcct ccaccaaggg cccatcggtc    420
ttccccctgg cacctcctc aagagcacc tctggggca gcggccct gggctgcctg    480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg gggcaccgt cagtcttcct cttcccccca    780
aaacccaagg acaccctcat gatctcccgg acccctgagg tcacatgcgt ggtggtggac    840
```

```
gtgagccacg aagaccctga ggtcaagttc aactggtacg tggacggcgt ggaggtgcat      900
aatgccaaga caaagccgcg ggaggagcag tacaacagca cgtaccgtgt ggtcagcgtc      960
ctcaccgtcc tgcaccagga ctggctgaat ggcaaggagt acaagtgcaa ggtctccaac     1020
aaagccctcc cagcccccat cgagaaaacc atctccaaag ccaaagggca gccccgagaa     1080
ccacaggtgt acaccctgcc cccatcccgg gatgagctga ccaagaacca ggtcagcctg     1140
acctgcctgg tcaaaggctt ctatcccagc gacatcgccg tggagtggga gagcaatggg     1200
cagccggaga caactacaa gaccacgcct cccgtgctgg actccgacgg ctccttcttc      1260
ctctacagca agctcaccgt ggacaagagc aggtggcagc aggggaacgt cttctcatgc     1320
tccgtgatgc atgaggctct gcacaaccac tacacgcaga gagcctctc cctgtctccg      1380 ggtaaatga                                                             1389
```

<210> SEQ ID NO 84
<211> LENGTH: 717
<212> TYPE: DNA
<213> ORGANISM: Artificial Sequence
<220> FEATURE:
<223> OTHER INFORMATION: PN encoding 2A10 humanised light chain
      construct L11 SEQ ID: 90

<400> SEQUENCE: 84

```
atgggatgga gctgtatcat cctcttcttg gtagcaacag ctacaggtgt ccactccgat       60
attgtgataa cccagtctcc actctccctg cccgtcaccc ttggacagcc ggcctccatc      120
tcctgcaggt ctagtaagag tctcctatat aaggatggga agacatactt gaattggttt      180
cagcagaggc caggccaatc tccacagctc ctaatttatt tgatgtccac ccgtgcatct      240
ggggtcccag acagattcag cggcggtggg tcaggcactg atttcacact gaaaatcagc      300
agggtggagg ctgaggatgt tggggtttat tactgccaac aacttgtaga gtatccgctc      360
acgtttggcc aggggaccaa gctggagatc aaacgtacgg tggctgcacc atctgtcttc      420
atcttcccgc catctgatga gcagttgaaa tctggaactg cctctgttgt gtgcctgctg      480
aataacttct atcccagaga ggccaaagta cagtggaagg tggacaacgc cctccaatcg      540
ggtaactccc aggagagtgt cacagagcag gacagcaagg acagcaccta cagcctcagc      600
agcaccctga cgctgagcaa agcagactac gagaaacaca aagtctacgc ctgcgaagtc      660
acccatcagg gcctgagctc gcccgtcaca aagagcttca caggggaga gtgttag         717
```

<210> SEQ ID NO 85
<211> LENGTH: 113
<212> TYPE: PRT
<213> ORGANISM: Artificial Sequence
<220> FEATURE:
<223> OTHER INFORMATION: 2A10 VH humanised construct H19

<400> SEQUENCE: 85

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Trp Met His Trp Val Arg Gln Arg Pro Gly Gln Gly Leu Glu Trp Ile
         35                  40                  45

Gly Asn Ile Asn Pro Ser Asn Gly Gly Thr Asn Tyr Asn Glu Lys Phe
     50                  55                  60

Lys Ser Arg Ala Thr Met Thr Arg Asp Thr Ser Thr Ser Thr Ala Tyr
 65                  70                  75                  80
```

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 86
<211> LENGTH: 113
<212> TYPE: PRT
<213> ORGANISM: Artificial Sequence
<220> FEATURE:
<223> OTHER INFORMATION: 2A10 VH humanised construct H20

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
    50                  55                  60

Lys Ser Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 87
<211> LENGTH: 113
<212> TYPE: PRT
<213> ORGANISM: Artificial Sequence
<220> FEATURE:
<223> OTHER INFORMATION: 2A10 VH humanised construct H21

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
    50                  55                  60

Lys Ser Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 88
<211> LENGTH: 113
<212> TYPE: PRT

<213> ORGANISM: Artificial Sequence
<220> FEATURE:
<223> OTHER INFORMATION: 2A10 VH humanised construct H22

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 89
<211> LENGTH: 113
<212> TYPE: PRT
<213> ORGANISM: Artificial Sequence
<220> FEATURE:
<223> OTHER INFORMATION: 2A10 VH humanised construct H23

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 90
<211> LENGTH: 113
<212> TYPE: PRT
<213> ORGANISM: Artificial Sequence
<220> FEATURE:
<223> OTHER INFORMATION: 2A10 VH humanised construct H24

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile

-continued

```
                35                  40                  45
Gly Asn Ile Asn Pro Ser Asn Gly Gly Thr Asn Tyr Asn Glu Lys Phe
         50                  55                  60

Lys Ser Lys Ala Thr Leu Thr Val Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Glu Leu Gly Gln Gly Tyr Trp Gly Gln Gly Thr Leu Val Thr Val Ser
                100                 105                 110

Ser

<210> SEQ ID NO 91
<211> LENGTH: 113
<212> TYPE: PRT
<213> ORGANISM: Artificial Sequence
<220> FEATURE:
<223> OTHER INFORMATION: 2A10 VH humanised construct H25

<400> SEQUENCE: 91

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Met
             35                  40                  45

Gly Asn Ile Asn Pro Ser Asn Gly Gly Thr Asn Tyr Asn Glu Lys Phe
         50                  55                  60

Lys Ser Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Glu Leu Gly Gln Gly Tyr Trp Gly Gln Gly Thr Leu Val Thr Val Ser
                100                 105                 110

Ser

<210> SEQ ID NO 92
<211> LENGTH: 462
<212> TYPE: PRT
<213> ORGANISM: Artificial Sequence
<220> FEATURE:
<223> OTHER INFORMATION: 2A10 heavy chain humanised construct H19

<400> SEQUENCE: 92

Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
             35                  40                  45

Thr Ser Tyr Trp Met His Trp Val Arg Gln Arg Pro Gly Gln Gly Leu
         50                  55                  60

Glu Trp Ile Gly Asn Ile Asn Pro Ser Asn Gly Gly Thr Asn Tyr Asn
 65                  70                  75                  80

Glu Lys Phe Lys Ser Arg Ala Thr Met Thr Arg Asp Thr Ser Thr Ser
                 85                  90                  95

Thr Ala Tyr Met Glu Leu Ser Ser Leu Arg Ser Glu Asp Thr Ala Val
                100                 105                 110
```

```
Tyr Tyr Cys Glu Leu Gly Gln Gly Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 93
<211> LENGTH: 462
<212> TYPE: PRT
<213> ORGANISM: Artificial Sequence
<220> FEATURE:
<223> OTHER INFORMATION: 2A10 heavy chain humanised construct H20

<400> SEQUENCE: 93

Met Gly Trp Ser Cys Ile Ile Leu Phe Leu Val Ala Thr Ala Thr Gly
1               5                   10                  15
```

-continued

```
Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
             35                  40                  45

Thr Ser Tyr Trp Met His Trp Val Arg Gln Ala Pro Gly Gln Gly Leu
 50                  55                  60

Glu Trp Ile Gly Asn Ile Asn Pro Ser Asn Gly Gly Thr Asn Tyr Asn
 65                  70                  75                  80

Glu Lys Phe Lys Ser Lys Ala Thr Met Thr Arg Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430
```

```
Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 94
<211> LENGTH: 462
<212> TYPE: PRT
<213> ORGANISM: Artificial Sequence
<220> FEATURE:
<223> OTHER INFORMATION: 2A10 heavy chain humanised construct H21

<400> SEQUENCE: 94

Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Arg Gln Arg Pro Gly Gln Gly Leu
     50                  55                  60

Glu Trp Ile Gly Asn Ile Asn Pro Ser Asn Gly Gly Thr Asn Tyr Asn
 65                  70                  75                  80

Glu Lys Phe Lys Ser Lys Ala Thr Met Thr Arg Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335
```

```
Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                    405                 410                 415

Gly Ser Phe Phe Leu Tyr Ser Lys Leu Thr Val Asp Lys Ser Arg Trp
                    420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 95
<211> LENGTH: 462
<212> TYPE: PRT
<213> ORGANISM: Artificial Sequence
<220> FEATURE:
<223> OTHER INFORMATION: 2A10 heavy chain humanised construct H22

<400> SEQUENCE: 95

Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Lys Gln Arg Pro Gly Gln Gly Leu
     50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Met Thr Arg Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240
```

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 96
<211> LENGTH: 462
<212> TYPE: PRT
<213> ORGANISM: Artificial Sequence
<220> FEATURE:
<223> OTHER INFORMATION: 2A10 heavy chain humanised construct H23

<400> SEQUENCE: 96

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Met Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

```
Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460

<210> SEQ ID NO 97
<211> LENGTH: 462
<212> TYPE: PRT
<213> ORGANISM: Artificial Sequence
<220> FEATURE:
<223> OTHER INFORMATION: 2A10 heavy chain humanised construct H24

<400> SEQUENCE: 97

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45
```

-continued

```
Thr Ser Tyr Trp Met His Trp Val Lys Gln Arg Pro Gly Gln Gly Leu
 50              55                  60

Glu Trp Ile Gly Asn Ile Asn Pro Ser Asn Gly Gly Thr Asn Tyr Asn
 65              70                  75                  80

Glu Lys Phe Lys Ser Lys Ala Thr Leu Thr Val Asp Thr Ser Thr Ser
                 85                  90                  95

Thr Ala Tyr Met Glu Leu Ser Ser Leu Arg Ser Glu Asp Thr Ala Val
             100                 105                 110

Tyr Tyr Cys Glu Leu Gly Gln Gly Tyr Trp Gly Gln Gly Thr Leu Val
         115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460
```

```
<210> SEQ ID NO 98
<211> LENGTH: 462
<212> TYPE: PRT
<213> ORGANISM: Artificial Sequence
<220> FEATURE:
<223> OTHER INFORMATION: 2A10 heavy chain humanised construct H25

<400> SEQUENCE: 98
```

| | | | | | | | | | | | | | | |
|---|---|---|---|---|---|---|---|---|---|---|---|---|---|---|
| Met | Gly | Trp | Ser | Cys | Ile | Ile | Leu | Phe | Leu | Val | Ala | Thr | Ala | Gly |
| 1 | | | | 5 | | | | | 10 | | | | | 15 |
| Val | His | Ser | Gln | Val | Gln | Leu | Val | Gln | Ser | Gly | Ala | Glu | Val | Lys | Lys |
| | | | 20 | | | | | 25 | | | | | 30 | |
| Pro | Gly | Ala | Ser | Val | Lys | Val | Ser | Cys | Lys | Ala | Ser | Gly | Tyr | Thr | Phe |
| | | 35 | | | | | 40 | | | | | 45 | | |
| Thr | Ser | Tyr | Trp | Met | His | Trp | Val | Arg | Gln | Arg | Pro | Gly | Gln | Gly | Leu |
| | 50 | | | | | 55 | | | | | 60 | | | | |
| Glu | Trp | Met | Gly | Asn | Ile | Asn | Pro | Ser | Asn | Gly | Gly | Thr | Asn | Tyr | Asn |
| 65 | | | | | 70 | | | | | 75 | | | | | 80 |
| Glu | Lys | Phe | Lys | Ser | Arg | Val | Thr | Met | Thr | Arg | Asp | Thr | Ser | Thr | Ser |
| | | | | 85 | | | | | 90 | | | | | 95 | |
| Thr | Ala | Tyr | Met | Glu | Leu | Ser | Ser | Leu | Arg | Ser | Glu | Asp | Thr | Ala | Val |
| | | | 100 | | | | | 105 | | | | | 110 | | |
| Tyr | Tyr | Cys | Glu | Leu | Gly | Gln | Gly | Tyr | Trp | Gly | Gln | Gly | Thr | Leu | Val |
| | | 115 | | | | | 120 | | | | | 125 | | | |
| Thr | Val | Ser | Ser | Ala | Ser | Thr | Lys | Gly | Pro | Ser | Val | Phe | Pro | Leu | Ala |
| | 130 | | | | | 135 | | | | | 140 | | | | |
| Pro | Ser | Ser | Lys | Ser | Thr | Ser | Gly | Gly | Thr | Ala | Ala | Leu | Gly | Cys | Leu |
| 145 | | | | | 150 | | | | | 155 | | | | | 160 |
| Val | Lys | Asp | Tyr | Phe | Pro | Glu | Pro | Val | Thr | Val | Ser | Trp | Asn | Ser | Gly |
| | | | | 165 | | | | | 170 | | | | | 175 | |
| Ala | Leu | Thr | Ser | Gly | Val | His | Thr | Phe | Pro | Ala | Val | Leu | Gln | Ser | Ser |
| | | | 180 | | | | | 185 | | | | | 190 | | |
| Gly | Leu | Tyr | Ser | Leu | Ser | Ser | Val | Val | Thr | Val | Pro | Ser | Ser | Ser | Leu |
| | | 195 | | | | | 200 | | | | | 205 | | | |
| Gly | Thr | Gln | Thr | Tyr | Ile | Cys | Asn | Val | Asn | His | Lys | Pro | Ser | Asn | Thr |
| | 210 | | | | | 215 | | | | | 220 | | | | |
| Lys | Val | Asp | Lys | Lys | Val | Glu | Pro | Lys | Ser | Cys | Asp | Lys | Thr | His | Thr |
| 225 | | | | | 230 | | | | | 235 | | | | | 240 |
| Cys | Pro | Pro | Cys | Pro | Ala | Pro | Glu | Leu | Ala | Gly | Ala | Pro | Ser | Val | Phe |
| | | | | 245 | | | | | 250 | | | | | 255 | |
| Leu | Phe | Pro | Pro | Lys | Pro | Lys | Asp | Thr | Leu | Met | Ile | Ser | Arg | Thr | Pro |
| | | | 260 | | | | | 265 | | | | | 270 | | |
| Glu | Val | Thr | Cys | Val | Val | Val | Asp | Val | Ser | His | Glu | Asp | Pro | Glu | Val |
| | | 275 | | | | | 280 | | | | | 285 | | | |
| Lys | Phe | Asn | Trp | Tyr | Val | Asp | Gly | Val | Glu | Val | His | Asn | Ala | Lys | Thr |
| | 290 | | | | | 295 | | | | | 300 | | | | |
| Lys | Pro | Arg | Glu | Glu | Gln | Tyr | Asn | Ser | Thr | Tyr | Arg | Val | Val | Ser | Val |
| 305 | | | | | 310 | | | | | 315 | | | | | 320 |
| Leu | Thr | Val | Leu | His | Gln | Asp | Trp | Leu | Asn | Gly | Lys | Glu | Tyr | Lys | Cys |
| | | | | 325 | | | | | 330 | | | | | 335 | |
| Lys | Val | Ser | Asn | Lys | Ala | Leu | Pro | Ala | Pro | Ile | Glu | Lys | Thr | Ile | Ser |
| | | | 340 | | | | | 345 | | | | | 350 | | |
| Lys | Ala | Lys | Gly | Gln | Pro | Arg | Glu | Pro | Gln | Val | Tyr | Thr | Leu | Pro | Pro |
| | | 355 | | | | | 360 | | | | | 365 | | | |
| Ser | Arg | Asp | Glu | Leu | Thr | Lys | Asn | Gln | Val | Ser | Leu | Thr | Cys | Leu | Val |

|     | 370 |     |     | 375 |     |     | 380 |     |     |
|---|---|---|---|---|---|---|---|---|---|
| Lys | Gly | Phe | Tyr | Pro | Ser | Asp | Ile | Ala | Val | Glu | Trp | Glu | Ser | Asn | Gly |
| 385 |     |     |     | 390 |     |     |     | 395 |     |     |     |     |     | 400 |     |

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 99
<211> LENGTH: 339
<212> TYPE: DNA
<213> ORGANISM: Artificial Sequence
<220> FEATURE:
<223> OTHER INFORMATION: PN encoding 2A10 VH humanised construct H19 SEQ
      ID: 85

<400> SEQUENCE: 99
caggtgcagc tggtgcagtc tggggctgag gtgaagaagc ctggggcctc agtgaaggtt     60
tcctgcaagg catctggata caccttcacc agctactgga tgcactgggt gcgacagagg    120
cctggacaag ggcttgagtg gatcggaaat attaatccta gcaatggtgg tactaactac    180
aatgagaagt tcaagagcag agccaccatg accagggaca cgtccacgag cacagcctac    240
atggagctga gcagcctgag atctgaggac acggccgtgt attactgtga actgggacag    300
ggctactggg gccagggaac actagtcaca gtctcctca                           339

<210> SEQ ID NO 100
<211> LENGTH: 339
<212> TYPE: DNA
<213> ORGANISM: Artificial Sequence
<220> FEATURE:
<223> OTHER INFORMATION: PN encoding 2A10 VH humanised construct H20 SEQ
      ID: 86

<400> SEQUENCE: 100
caggtgcagc tggtgcagtc tggggctgag gtgaagaagc ctggggcctc agtgaaggtt     60
tcctgcaagg catctggata caccttcacc agctactgga tgcactgggt gcgacaggcc    120
cctggacaag ggcttgagtg gatcggaaat attaatccta gcaatggtgg tactaactac    180
aatgagaagt tcaagagcaa ggccaccatg accagggaca cgtccacgag cacagcctac    240
atggagctga gcagcctgag atctgaggac acggccgtgt attactgtga actgggacag    300
ggctactggg gccagggaac actagtcaca gtctcctca                           339

<210> SEQ ID NO 101
<211> LENGTH: 339
<212> TYPE: DNA
<213> ORGANISM: Artificial Sequence
<220> FEATURE:
<223> OTHER INFORMATION: PN encoding 2A10 VH humanised construct H21 SEQ
      ID: 87

<400> SEQUENCE: 101
caggtgcagc tggtgcagtc tggggctgag gtgaagaagc ctggggcctc agtgaaggtt     60
tcctgcaagg catctggata caccttcacc agctactgga tgcactgggt gcgacagagg    120
cctggacaag ggcttgagtg gatcggaaat attaatccta gcaatggtgg tactaactac    180

```
aatgagaagt tcaagagcaa ggccaccatg accagggaca cgtccacgag cacagcctac    240
atggagctga gcagcctgag atctgaggac acggccgtgt attactgtga actgggacag    300
ggctactggg gccagggaac actagtcaca gtctcctca                           339

<210> SEQ ID NO 102
<211> LENGTH: 339
<212> TYPE: DNA
<213> ORGANISM: Artificial Sequence
<220> FEATURE:
<223> OTHER INFORMATION: PN encoding 2A10 VH humanised construct H22 SEQ
      ID: 88

<400> SEQUENCE: 102
caggtgcagc tggtgcagtc tggggctgag gtgaagaagc ctggggcctc agtgaaggtt    60
tcctgcaagg catctggata caccttcacc agctactgga tgcactgggt gaagcagagg    120
cctggacaag gcttgagtg gatcggaaat attaatccta gcaatggtgg tactaactac     180
aatgagaagt tcaagagcaa ggccaccatg accagggaca cgtccacgag cacagcctac    240
atggagctga gcagcctgag atctgaggac acggccgtgt attactgtga actgggacag    300
ggctactggg gccagggaac actagtcaca gtctcctca                           339

<210> SEQ ID NO 103
<211> LENGTH: 339
<212> TYPE: DNA
<213> ORGANISM: Artificial Sequence
<220> FEATURE:
<223> OTHER INFORMATION: PN encoding 2A10 VH humanised construct H23 SEQ
      ID: 89

<400> SEQUENCE: 103
caggtgcagc tggtgcagtc tggggctgag gtgaagaagc ctggggcctc agtgaaggtt    60
tcctgcaagg catctggata caccttcacc agctactgga tgcactgggt gaagcagagg    120
cctggacaag gcttgagtg gatcggaaat attaatccta gcaatggtgg tactaactac     180
aatgagaagt tcaagagcaa ggccaccatg accgtagaca cgtccacgag cacagcctac    240
atggagctga gcagcctgag atctgaggac acggccgtgt attactgtga actgggacag    300
ggctactggg gccagggaac actagtcaca gtctcctca                           339

<210> SEQ ID NO 104
<211> LENGTH: 339
<212> TYPE: DNA
<213> ORGANISM: Artificial Sequence
<220> FEATURE:
<223> OTHER INFORMATION: PN encoding 2A10 VH humanised construct H24 SEQ
      ID: 90

<400> SEQUENCE: 104
caggtgcagc tggtgcagtc tggggctgag gtgaagaagc ctggggcctc agtgaaggtt    60
tcctgcaagg catctggata caccttcacc agctactgga tgcactgggt gaagcagagg    120
cctggacaag gcttgagtg gatcggaaat attaatccta gcaatggtgg tactaactac     180
aatgagaagt tcaagagcaa ggccaccctg accgtagaca cgtccacgag cacagcctac    240
atggagctga gcagcctgag atctgaggac acggccgtgt attactgtga actgggacag    300
ggctactggg gccagggaac actagtcaca gtctcctca                           339

<210> SEQ ID NO 105
<211> LENGTH: 339
```

```
<212> TYPE: DNA
<213> ORGANISM: Artificial Sequence
<220> FEATURE:
<223> OTHER INFORMATION: PN encoding 2A10 VH humanised construct H25 SEQ
      ID: 91

<400> SEQUENCE: 105
caggtgcagc tggtgcagtc tggggctgag gtgaagaagc ctggggcctc agtgaaggtt      60
tcctgcaagg catctggata caccttcacc agctactgga tgcactgggt gcgacagagg     120
cctggacaag gcttgagtg atgggaaat attaatccta gcaatggtgg tactaactac       180
aatgagaagt tcaagagcag agtcaccatg accaggaca cgtccacgag cacagcctac      240
atggagctga gcagcctgag atctgaggac acggccgtgt attactgtga actgggacag     300
ggctactggg gccagggaac actagtcaca gtctcctca                            339

<210> SEQ ID NO 106
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H19 SEQ ID: 92

<400> SEQUENCE: 106
atgggatgga gctgtatcat cctcttcttg gtagcaacag ctacaggtgt ccactcccag      60
gtgcagctgg tgcagtctgg ggctgaggtg aagaagcctg ggcctcagt gaaggtttcc     120 tgcaaggcat ctggatacac cttcaccagc tactggatgc actgggtgcg acagaggcct    180 ggacaaggc ttgagtggat cggaaatatt aatcctagca atggtggtac taactacaat     240
gagaagttca agagcagagc caccatgacc agggacacg ccacgagcac agcctacatg      300
gagctgagca gcctgagatc tgaggacacg gccgtgtatt actgtgaact gggacagggc    360
tactggggcc agggaacact agtcacagtc tcctcagcct ccaccaaggg cccatcggtc    420
ttccccctgg caccctcctc aagagcacc tctgggggca gcggccct gggctgcctg       480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg gggcaccgt cagtcttcct cttccccca     780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagccccat cgagaaaacc atctccaaag ccaaggcca gccccgagaa     1080 ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                           1389
```

<210> SEQ ID NO 107
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H20 SEQ ID: 93

<400> SEQUENCE: 107

| | |
|---|---|
| atgggatgga gctgtatcat cctcttcttg gtagcaacag ctacaggtgt ccactcccag | 60 |
| gtgcagctgg tgcagtctgg ggctgaggtg aagaagcctg ggcctcagt gaaggtttcc | 120 |
| tgcaaggcat ctggatacac cttcaccagc tactggatgc actgggtgcg acaggcccct | 180 |
| ggacaagggc ttgagtggat cggaaatatt aatcctagca atggtggtac taactacaat | 240 |
| gagaagttca gagcaaggc caccatgacc agggacacgt ccacgagcac agcctacatg | 300 |
| gagctgagca gcctgagatc tgaggacacg gccgtgtatt actgtgaact gggacagggc | 360 |
| tactggggcc agggaacact agtcacagtc tcctcagcct ccaccaaggg cccatcggtc | 420 |
| ttccccctgg caccctcctc caagagcacc tctgggggca cagcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg ggggcaccgt cagtcttcct cttcccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |
| aatgccaaga caaagccgcg ggaggagcag tacaacagca cgtaccgtgt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaaagggca gccccgagaa | 1080 |
| ccacaggtgt acaccctgcc cccatcccgg gatgagctga ccaagaacca ggtcagcctg | 1140 |
| acctgcctgg tcaaaggctt ctatcccagc gacatcgccg tggagtggga gagcaatggg | 1200 |
| cagccggaga caactacaa gaccacgcct cccgtgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 108
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H21 SEQ ID: 94

<400> SEQUENCE: 108

| | |
|---|---|
| atgggatgga gctgtatcat cctcttcttg gtagcaacag ctacaggtgt ccactcccag | 60 |
| gtgcagctgg tgcagtctgg ggctgaggtg aagaagcctg ggcctcagt gaaggtttcc | 120 |
| tgcaaggcat ctggatacac cttcaccagc tactggatgc actgggtgcg acagaggcct | 180 |
| ggacaagggc ttgagtggat cggaaatatt aatcctagca atggtggtac taactacaat | 240 |
| gagaagttca gagcaaggc caccatgacc agggacacgt ccacgagcac agcctacatg | 300 |

-continued

| | |
|---|---|
| gagctgagca gcctgagatc tgaggacacg gccgtgtatt actgtgaact gggacagggc | 360 |
| tactggggcc agggaacact agtcacagtc tcctcagcct ccaccaaggg cccatcggtc | 420 |
| ttccccctgg caccctcctc caagagcacc tctgggggca gcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg gggcaccgt cagtcttcct cttcccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |
| aatgccaaga caaagccgcg ggaggagcag tacaacagca cgtaccgtgt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaaagggca gccccgagaa | 1080 |
| ccacaggtgt acaccctgcc cccatcccgg gatgagctga ccaagaacca ggtcagcctg | 1140 |
| acctgcctgg tcaaaggctt ctatcccagc gacatcgccg tggagtggga gagcaatggg | 1200 |
| cagccggaga caactacaa gaccacgcct cccgtgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 109
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H22 SEQ ID: 95

<400> SEQUENCE: 109

| | |
|---|---|
| atgggatgga gctgtatcat cctcttcttg gtagcaacag ctacaggtgt ccactcccag | 60 |
| gtgcagctgg tgcagtctgg ggctgaggtg aagaagcctg ggcctcagt gaaggtttcc | 120 |
| tgcaaggcat ctggatacac cttcaccagc tactggatgc actgggtgaa gcagaggcct | 180 |
| ggacaagggc ttgagtggat cggaaatatt aatcctagca tggtggtac taactacaat | 240 |
| gagaagttca gagcaaggc caccatgacc agggacacgt ccacgagcac agcctacatg | 300 |
| gagctgagca gcctgagatc tgaggacacg gccgtgtatt actgtgaact gggacagggc | 360 |
| tactggggcc agggaacact agtcacagtc tcctcagcct ccaccaaggg cccatcggtc | 420 |
| ttccccctgg caccctcctc caagagcacc tctgggggca gcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg gggcaccgt cagtcttcct cttcccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |

```
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaagggca gccccgagaa    1080 ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc    1260
ctctacagca agctcaccgt ggacaagagc aggtggcagc aggggaacgt cttctcatgc   1320
tccgtgatgc atgaggctct gcacaaccac tacacgcaga agagcctctc cctgtctccg   1380
ggtaaatga                                                           1389
```

<210> SEQ ID NO 110
<211> LENGTH: 1389
<212> TYPE: DNA
<213> ORGANISM: Artificial Sequence
<220> FEATURE:
<223> OTHER INFORMATION: PN encoding 2A10 heavy chain humanised
      construct H23 SEQ ID: 96

<400> SEQUENCE: 110

```
atgggatgga gctgtatcat cctcttcttg gtagcaacag ctacaggtgt ccactcccag     60
gtgcagctgg tgcagtctgg ggctgaggtg aagaagcctg ggcctcagt gaaggtttcc    120 tgcaaggcat ctggatacac cttcaccagc tactggatgc actgggtgaa gcagaggcct    180 ggacaaggc ttgagtggat cggaaatatt aatcctagca atggtggtac taactacaat    240
gagaagttca gagcaaggc caccatgacc gtagacacgt ccacgagcac agcctacatg    300
gagctgagca gcctgagatc tgaggacacg gccgtgtatt actgtgaact gggacagggc   360
tactggggcc agggaacact agtcacagtc tcctcagcct ccaccaaggg cccatcggtc    420
ttccccctgg caccctcctc aagagcacc tctgggggca gcggccct gggctgcctg      480 gtcaaggact acttccccga accggtgacg gtgtcgtgga actcaggcgc cctgaccagc   540
ggcgtgcaca ccttcccggc tgtcctacag tcctcaggac tctactccct cagcagcgtg   600
gtgaccgtgc cctccagcag cttgggcacc cagacctaca tctgcaacgt gaatcacaag   660
cccagcaaca ccaaggtgga caagaaagtt gagcccaaat cttgtgacaa aactcacaca   720
tgcccaccgt gccagcacc tgaactcgcg gggcaccgt cagtcttcct cttccccca    780 aaacccaagg acaccctcat gatctcccgg acccctgagg tcacatgcgt ggtggtggac   840
gtgagccacg aagaccctga ggtcaagttc aactggtacg tggacggcgt ggaggtgcat   900
aatgccaaga caaagccgcg ggaggagcag tacaacagca cgtaccgtgt ggtcagcgtc   960
ctcaccgtcc tgcaccagga ctggctgaat ggcaaggagt acaagtgcaa ggtctccaac  1020
aaagccctcc cagcccccat cgagaaaacc atctccaaag ccaagggca gccccgagaa   1080 ccacaggtgt acaccctgcc cccatcccgg gatgagctga ccaagaacca ggtcagcctg  1140
acctgcctgg tcaaaggctt ctatcccagc gacatcgccg tggagtggga gagcaatggg  1200
cagccggaga caactacaa gaccacgcct cccgtgctgg actccgacgg ctccttcttc   1260
ctctacagca agctcaccgt ggacaagagc aggtggcagc aggggaacgt cttctcatgc  1320
tccgtgatgc atgaggctct gcacaaccac tacacgcaga agagcctctc cctgtctccg  1380
ggtaaatga                                                          1389
```

<210> SEQ ID NO 111
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H24 SEQ ID: 97

<400> SEQUENCE: 111

| | | | | | |
|---|---|---|---|---|---|
| atgggatgga | gctgtatcat | cctcttcttg | gtagcaacag | ctacaggtgt | ccactcccag | 60 |
| gtgcagctgg | tgcagtctgg | ggctgaggtg | aagaagcctg | gggcctcagt | gaaggtttcc | 120 |
| tgcaaggcat | ctggatacac | cttcaccagc | tactggatgc | actgggtgaa | gcagaggcct | 180 |
| ggacaagggc | ttgagtggat | cggaaatatt | aatcctagca | atggtggtac | taactacaat | 240 |
| gagaagttca | gagcaaggc | caccctgacc | gtagacacgt | ccacgagcac | agcctacatg | 300 |
| gagctgagca | gcctgagatc | tgaggacacg | gccgtgtatt | actgtgaact | gggacagggc | 360 |
| tactggggcc | aggaacact | agtcacagtc | tcctcagcct | ccaccaaggg | cccatcggtc | 420 |
| ttccccctgg | caccctcctc | aagagcacc | tctgggggca | cagcggccct | gggctgcctg | 480 |
| gtcaaggact | acttccccga | accggtgacg | gtgtcgtgga | actcaggcgc | cctgaccagc | 540 |
| ggcgtgcaca | ccttcccggc | tgtcctacag | tcctcaggac | tctactccct | cagcagcgtg | 600 |
| gtgaccgtgc | cctccagcag | cttgggcacc | cagacctaca | tctgcaacgt | gaatcacaag | 660 |
| cccagcaaca | ccaaggtgga | caagaaagtt | gagcccaaat | cttgtgacaa | aactcacaca | 720 |
| tgcccaccgt | gcccagcacc | tgaactcgcg | gggcaccgt | cagtcttcct | cttccccca | 780 |
| aaacccaagg | acaccctcat | gatctcccgg | acccctgagg | tcacatgcgt | ggtggtggac | 840 |
| gtgagccacg | aagaccctga | ggtcaagttc | aactggtacg | tggacggcgt | ggaggtgcat | 900 |
| aatgccaaga | caaagccgcg | ggaggagcag | tacaacagca | cgtaccgtgt | ggtcagcgtc | 960 |
| ctcaccgtcc | tgcaccagga | ctggctgaat | ggcaaggagt | acaagtgcaa | ggtctccaac | 1020 |
| aaagccctcc | cagccccat | cgagaaaacc | atctccaaag | ccaaagggca | gccccgagaa | 1080 |
| ccacaggtgt | acaccctgcc | cccatcccgg | gatgagctga | ccaagaacca | ggtcagcctg | 1140 |
| acctgcctgg | tcaaaggctt | ctatcccagc | gacatcgccg | tggagtggga | gagcaatggg | 1200 |
| cagccggaga | acaactacaa | gaccacgcct | cccgtgctgg | actccgacgg | ctccttcttc | 1260 |
| ctctacagca | agctcaccgt | ggacaagagc | aggtggcagc | aggggaacgt | cttctcatgc | 1320 |
| tccgtgatgc | atgaggctct | gcacaaccac | tacacgcaga | agagcctctc | cctgtctccg | 1380 |
| ggtaaatga | | | | | | 1389 |

<210> SEQ ID NO 112
<211> LENGTH: 1389
<212> TYPE: DNA
<213> ORGANISM: Artificial Sequence
<220> FEATURE:
<223> OTHER INFORMATION: PN encoding 2A10 heavy chain humanised construct H25 SEQ ID: 98

<400> SEQUENCE: 112

| | | | | | |
|---|---|---|---|---|---|
| atgggatgga | gctgtatcat | cctcttcttg | gtagcaacag | ctacaggtgt | ccactcccag | 60 |
| gtgcagctgg | tgcagtctgg | ggctgaggtg | aagaagcctg | gggcctcagt | gaaggtttcc | 120 |
| tgcaaggcat | ctggatacac | cttcaccagc | tactggatgc | actgggtgcg | acagaggcct | 180 |
| ggacaagggc | ttgagtggat | gggaaatatt | aatcctagca | atggtggtac | taactacaat | 240 |
| gagaagttca | gagcagagt | caccatgacc | agggacacgt | ccacgagcac | agcctacatg | 300 |

-continued

```
gagctgagca gcctgagatc tgaggacacg gccgtgtatt actgtgaact gggacagggc    360
tactggggcc agggaacact agtcacagtc tcctcagcct ccaccaaggg cccatcggtc    420
ttccccctgg cacccctcctc aagagcacc tctgggggca cagcggccct gggctgcctg    480
gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg gggcaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc   1260
ctctacagca agctcaccgt ggacaagagc aggtggcagc aggggaacgt cttctcatgc   1320
tccgtgatgc atgaggctct gcacaaccac tacacgcaga gagcctctc cctgtctccg   1380 ggtaaatga                                                            1389
```

<210> SEQ ID NO 113
<211> LENGTH: 200
<212> TYPE: PRT
<213> ORGANISM: Artificial Sequence
<220> FEATURE:
<223> OTHER INFORMATION: Amino acid sequence of Marmoset NOGO-A fragment

<400> SEQUENCE: 113

```
Val Gln Asp Ser Leu Cys Pro Val Ala Gln Leu Cys Pro Ser Phe Glu
  1               5                  10                  15

Glu Ser Glu Ala Thr Pro Ser Pro Val Leu Pro Asp Ile Val Met Glu
             20                  25                  30

Ala Pro Leu Asn Ser Ala Val Pro Ser Ala Gly Ala Ser Ala Val Gln
         35                  40                  45

Pro Ser Ser Ser Pro Leu Glu Ala Ser Ser Val Asn Phe Glu Ser Val
     50                  55                  60

Lys His Glu Pro Glu Asn Pro Pro Tyr Glu Ala Met Asn Val
 65                  70                  75                  80

Ser Arg Lys Lys Val Ser Gly Ile Lys Glu Glu Ile Lys Glu Pro Glu
                 85                  90                  95

Ser Ile Asn Ala Ala Val Gln Glu Thr Glu Ala Pro Tyr Ile Ser Ile
            100                 105                 110

Ala Cys Asp Leu Ile Lys Glu Thr Lys Leu Ser Ala Glu Pro Thr Pro
        115                 120                 125

Asp Phe Ser Ser Tyr Ser Glu Met Ala Lys Val Glu Gln Pro Leu Pro
    130                 135                 140

Asp His Ser Glu Leu Val Glu Asp Ser Pro Asp Ser Glu Pro Val
145                 150                 155                 160

Asp Leu Phe Ser Asp Asp Ser Ile Pro Asp Val Pro Gln Lys Gln Asp
```

-continued

```
              165                 170                 175
Glu Ala Val Ile Leu Val Lys Glu Thr Leu Thr Glu Thr Ser Phe Glu
            180                 185                 190
Ser Met Ile Glu His Glu Asn Lys
        195                 200
```